(12) United States Patent
Janssen et al.

(10) Patent No.: US 11,813,070 B2
(45) Date of Patent: Nov. 14, 2023

(54) APPARATUS FOR MEASURING PRESSURE CHANGES IN STOMACH

(71) Applicant: VIPUN Medical NV, Boortmeerbeek (BE)

(72) Inventors: Pieter Janssen, Boortmeerbeek (BE); Nathalie Rommel, Bertem (BE); Jan Tack, Huldenberg (BE)

(73) Assignee: VIPUN Medical NV, Boortmeerbeek (BE)

( * ) Notice: Subject to any disclaimer, the term of this patent is extended or adjusted under 35 U.S.C. 154(b) by 473 days.

(21) Appl. No.: 16/637,337

(22) PCT Filed: Aug. 9, 2018

(86) PCT No.: PCT/EP2018/071587
§ 371 (c)(1),
(2) Date: Feb. 7, 2020

(87) PCT Pub. No.: WO2019/030312
PCT Pub. Date: Feb. 14, 2019

(65) Prior Publication Data
US 2021/0369185 A1     Dec. 2, 2021

(30) Foreign Application Priority Data

Aug. 10, 2017  (GB) ..................................... 1712812
Sep. 22, 2017  (EP) ..................................... 17192538
May 15, 2018  (EP) ..................................... 18172298

(51) Int. Cl.
*A61B 5/00*        (2006.01)
*A61J 15/00*       (2006.01)

(52) U.S. Cl.
CPC .......... *A61B 5/4238* (2013.01); *A61B 5/6853* (2013.01); *A61J 15/0003* (2013.01); *A61J 15/0084* (2015.05); *A61B 2562/0247* (2013.01)

(58) Field of Classification Search
CPC ...... A61M 25/1002; A61M 2025/1015; A61M 2025/0003; A61M 25/10;
(Continued)

(56) References Cited

U.S. PATENT DOCUMENTS 4,367,740 A * 1/1983 Evanoski, III ......... A61B 5/205
                                                       604/920
5,370,618 A * 12/1994 Leonhardt ............... B29C 49/48
                                                       604/103
(Continued)

FOREIGN PATENT DOCUMENTS

CN      103747753 B  *  4/2017  ............. A61B 18/04
WO           9428792 A1      12/1994
(Continued)

OTHER PUBLICATIONS

Bhowmick et al. "Handbook of Elastomers, Second Edition", CRC Press, Nov. 2, 2000 at p. 367 (Year: 2000).*
(Continued)

*Primary Examiner* — Devin B Henson
(74) *Attorney, Agent, or Firm* — DINSMORE & SHOHL LLP

(57) ABSTRACT

A balloon catheter (100), suitable for delivery of a balloon to the stomach via application by the nose, the balloon catheter comprising a catheter (2) and one or more inflatable balloons (1) fixedly attached to the catheter. The balloons have an outer diameter from 4 to 7 cm, are made of a relatively hard material (e.g. durometer 70 to 100 shore A), and have an effective length of 7 to 18 cm or a total inner volume of 90 to 330 ml, when inflated by 0.2 psi. A system comprising the balloon catheter, and a pressure sensor for measuring a pressure of a fluid inside the balloon, and optionally a fluid pump for inflating and/or deflating the
(Continued)

balloon, and a control unit for reading the pressure sensor and optionally for controlling the fluid pump.

20 Claims, 27 Drawing Sheets

(58) Field of Classification Search
CPC ... A61M 2025/1059; A61B 2562/0247; A61B 5/6852; A61B 5/6853; A61B 5/42; A61B 5/4205; A61B 5/4211; A61B 5/4222; A61B 5/4238; A61J 15/0049; A61J 15/0042; A61J 15/0026; A61J 15/0015; A61J 15/0011; A61J 15/0003; A61J 15/0076; A61J 15/008; A61J 15/0084
See application file for complete search history.

(56) References Cited

U.S. PATENT DOCUMENTS

| | | | |
|---|---|---|---|
| 5,433,216 A * | 7/1995 | Sugrue | A61B 5/036 600/593 |
| 2005/0015048 A1 * | 1/2005 | Chiu | A61M 25/10 604/101.04 |
| 2008/0167607 A1 | 7/2008 | Pfeiffer et al. | |
| 2010/0217185 A1 * | 8/2010 | Terliuc | A61B 1/018 600/153 |
| 2013/0184612 A1 | 7/2013 | Quackenbush et al. | |
| 2016/0029998 A1 * | 2/2016 | Brister | A61B 5/6861 600/424 |
| 2017/0136209 A1 | 5/2017 | Burnett et al. | |
| 2017/0172778 A1 | 6/2017 | Brister et al. | |
| 2018/0008156 A1 * | 1/2018 | Pandolfino | A61B 1/273 |
| 2018/0015264 A1 * | 1/2018 | Wang | A61M 5/172 |
| 2019/0083501 A1 * | 3/2019 | Lee | A61K 9/00 |
| 2019/0117519 A1 * | 4/2019 | Schmid-Schonbein | A61J 15/0084 |

FOREIGN PATENT DOCUMENTS

| | | |
|---|---|---|
| WO | 2008066943 A2 | 4/2007 |
| WO | 2008154450 A1 | 12/2008 |
| WO | 2012006625 A2 | 7/2011 |

OTHER PUBLICATIONS

English translation of CN 103747753B (Year: 2017).*
Crighton, et al., "A Comparison of the Effects of Intravenous Tramadol, Codeine, and Morphine on Gastric Emptying in Human Volunteers", Anesth Analg., pp. 445-449, 1998.
Deloose, et al., "The migrating motor complex: control mechanisms and its role in health and disease", Nature Reviews, Gastroenterology & Hepatology, vol. 9, pp. 271-285, May 2012.
Gonenne, et al. Effect of alvimopan and codeine on gastrointestinal transit: a randomized controlled study. Clinical gastroenterology and hepatology : the official clinical practice journal of the American Gastroenterological Association. 2005; 3(8): 784-91.
Hawkes, et al., "Effect of an enteric-release formulation of naloxone on intestinal transit in volunteers taking codeine", Aliment Pharmacol Ther., pp. 625-630, 2001.
Hurt, et al., "Gastric Residual Volumes in Critical Illness: What Do They Really Mean?", Hurt & McClave, pp. 481-490, 2010.
Jahnberg, et al., "Dynamic Gastric Response to Expansion before and after Vagotomy", pp. 593-598, 1975.
Maes, et al. "Combined carbon-13-glycine/carbon-14-octanoic acid breath test to monitor gastric emptying rates of liquids and solids", Journal of Nuclear Medicine, vol. 35, No. 5, pp. 824-832, May 1994.
Malagelada, et al., "Gastric motor abnormalities in diabetic and postvagotomy gastroparesis: Effect of metoclopramide and Bethanechol", Manometric Abnormalities in Gastropareses, pp. 286-293, Feb. 1980.
Mikus, et al., "Effect of codeine on gastrointestinal motility in relation to CYP2D6 phenotype", Clinical Pharmacology and Therapeutics, pp. 459-546, Apr. 1997.
Schoonjans, et al., "The 13C-octanoic acid breath test: validation of a new noninvasive method of measuring gastric emptying in rats", Neurogastroenterol & Motility, vol. 14, pp. 287-293, 2002.
Schwartz, et al., "Vagovagal Stimulation of Pancreatic-Polypeptide Secretion by Graded Distention of the Gastric Fundus and Antrum in Man", Digestion, vol. 19, pp. 307-314, 1979.
Stanghellini, et al., "Gastroparesis: separate entity or just a part of dyspepsia", CrossMark, BMJ, vol. 63, pp. 1972-1978, 2014.
Szarka, et al., "Methods for measurement of gastric motility", Am. J. Physiol Gastrointest Liver Physiol, pp. G461-G475, Jan. 15, 2009.
Takita, et al., "Gastric motility after selective proximal vagotomy", Gastroenterologia Japonica, vol. 13, No. 5, pp. 345-352, 1978.
Takita, et al., "Gastric motor function after selective proximal vagotomy and pyloroplasty for peptic ulcer", Chir. Gastroent. (Gastroent Surg.), vol. 9, No. 2, pp. 195-203, 1975.
Talley, et al., "Functional Dyspepsia", The New England Journal of Medicine, pp. 1853-1863, Nov. 5, 2015.
International European Search Report dated Nov. 16, 2018, in reference to co-pending European Patent Application No. PCT/EP2018/071587 filed Aug. 9, 2018.

* cited by examiner

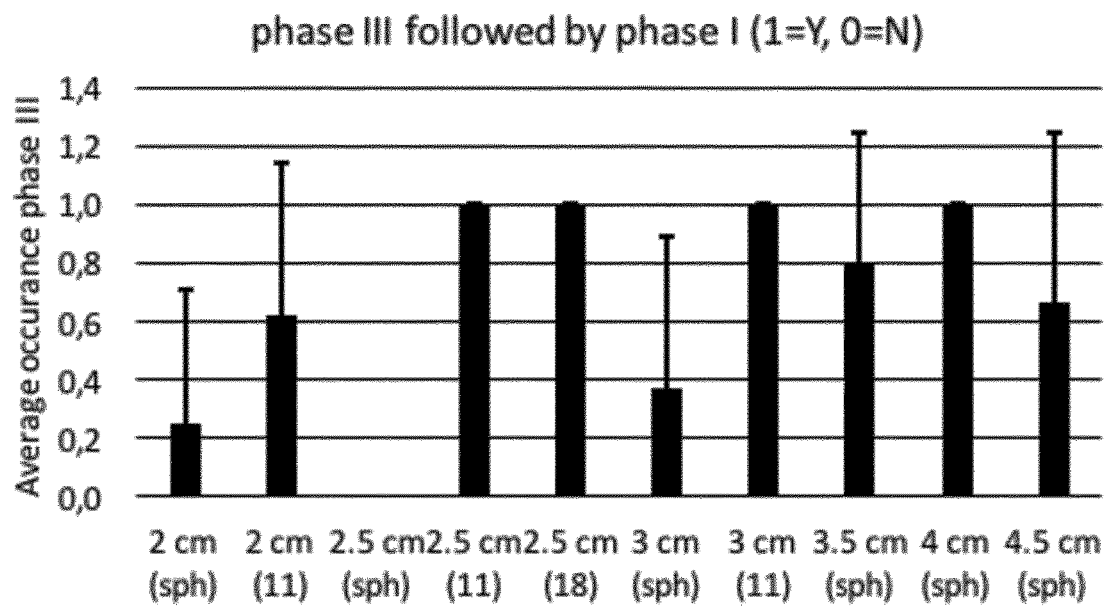
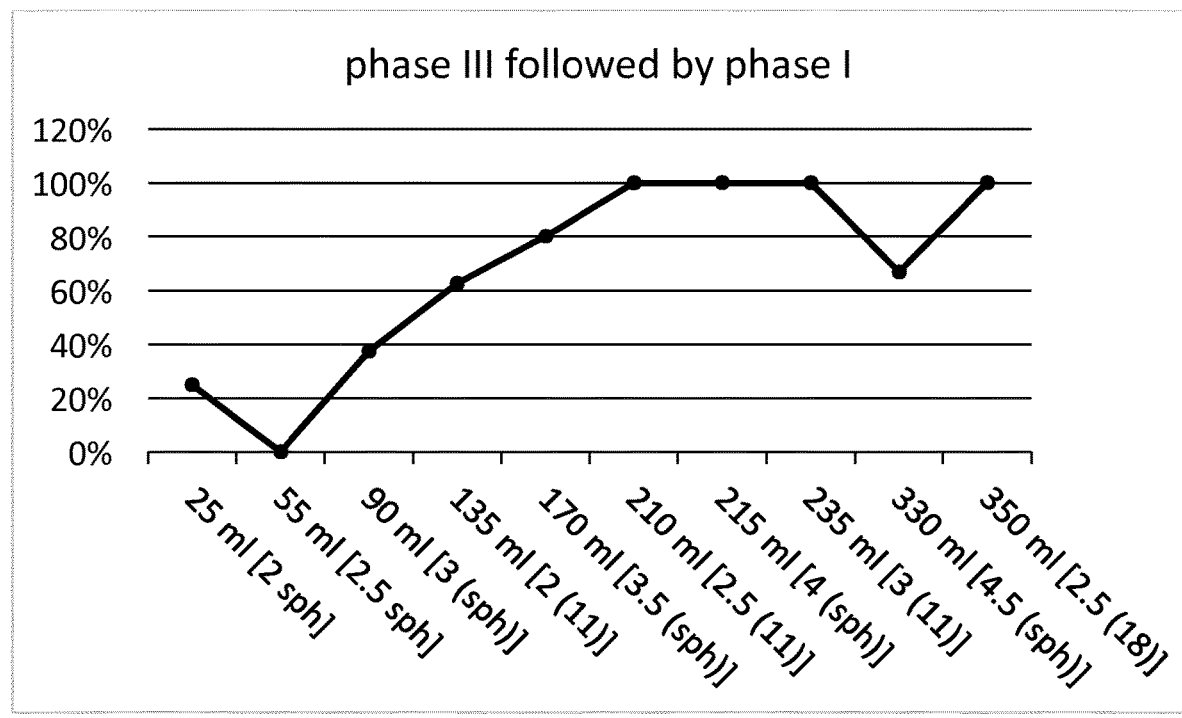
Figure 9

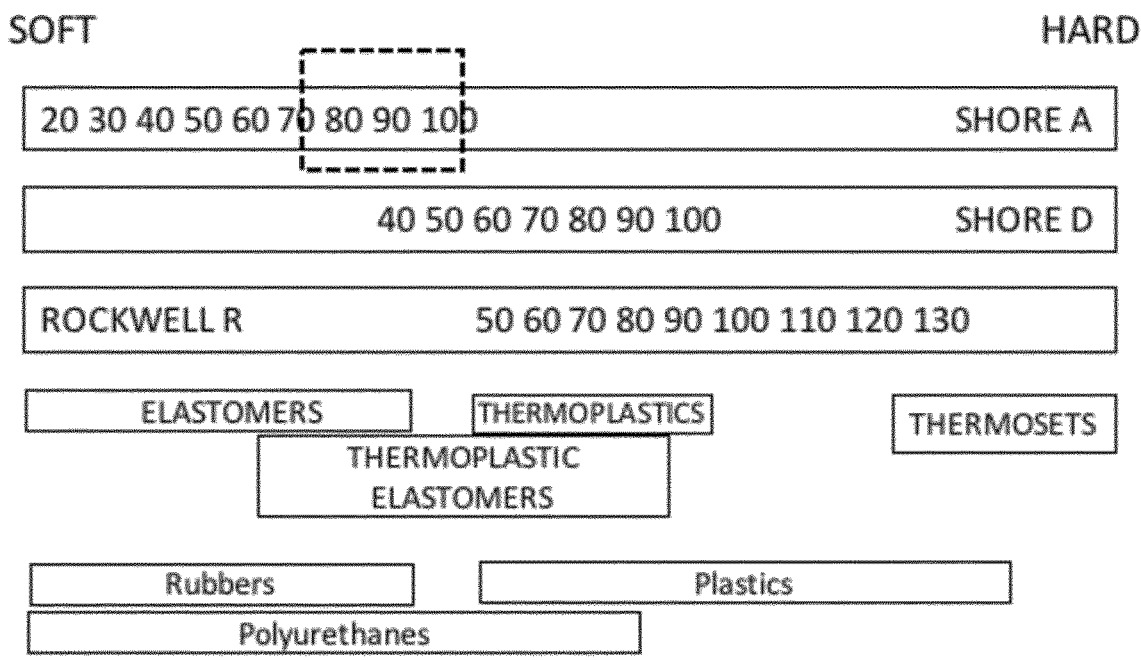
Figure 21
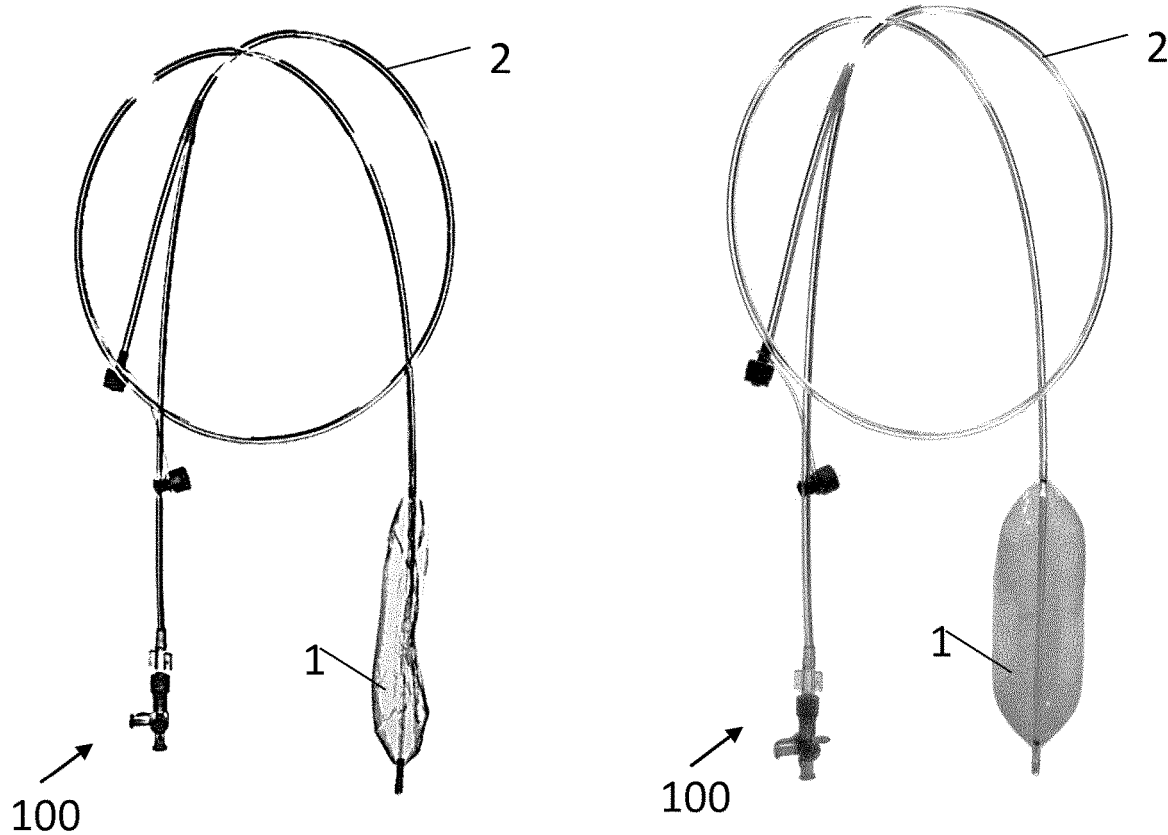
Figure 22
Figure 23

Target volume = 150 ml

APPARATUS FOR MEASURING PRESSURE CHANGES IN STOMACH

FIELD OF THE INVENTION

The present invention relates to devices for measuring gastric motility, and more in particular, to a balloon catheter comprising a catheter and at least one inflatable balloon for inserting into the stomach, and to a kit of parts containing such balloon catheter, and to a system for obtaining, recording and/or visualizing gastric motility information.

BACKGROUND OF THE INVENTION

The stomach is a central organ in gastrointestinal system and a major player in the food processing chain. Impaired motility and emptying are important pathophysiological factors involved in the intolerance of enteral feeding in critically ill patients but also in different gastrointestinal diseases and disorders such as Gastroparesis, Functional dyspepsia (FD)

Several methods are described in the prior art which can be used for measuring gastric motility. These are reviewed for example in Szarka & Camilleri Am. J. Physiol —Gastrointestinal & Liver Physiol 2009; 296(3): G461-G475 (1).

The proximal stomach is able to accommodate large volume changes while maintaining a relatively low intragastric pressure. Tonic contractions or relaxations are best measured using a balloon. The gold standard for the measurement of muscle tone in hollow organs is the barostat, which estimates changes in tone by the change of volume of air in an oversized balloon, having a volume typically larger than 1 liter, (connected to a double lumen catheter), maintained at a constant pressure. A variant is the tensostat, which corrects, in real time, for the changes in volume or diameter of the balloon to estimate luminal wall tension based on the Laplace law. Both balloon techniques require a large intragastric non-elastic balloon that has to be introduced via the mouth. These invasive tests cannot be used in daily clinical practice, and are often unacceptable to patients who are stressed and uncomfortable during these tests, restricting these techniques to a research setting.

In literature, gastric motility-induced phasic pressure changes have been described being measured using an inflated gastric balloon connected via a single lumen to an external pressure transducer (2-4). For this latter technique, a balloon connected to a catheter is passed into the stomach through the mouth (or nose). To date there is no standard method, catheter or balloon available and many balloon shapes, volumes and materials have been used and were always custom-made. To our knowledge, the balloons used in these studies were always highly elastic of nature (e.g. rubber or latex) and positioned on a single lumen catheter, moreover were they often over-dimensioned. In the prior art, 2 studies were found using a custom-made elastic balloon (rubber) on a single lumen vinyl tube that was positioned through the nostrils (5, 6). These techniques were never applied in daily routine practice since they were not optimized for comfortable passage through the throat/nostrils.

The distal stomach, pylorus, and duodenum, with their relatively small diameters and ability to generate high-amplitude pressure activity, are suitable for manometric recordings using a thin (e.g. 18 French) tube without balloon. This 'ordinary' manometry can be used to monitor gastric motility by measuring gastric pressure using a single water-perfused lumen inserted into the stomach of a subject and connected to an external pressure transducer (water-perfused manometry). Alternatively, and more recently, a relative thin (max 18 French), pressure-sensitive tube is used with pressure transducers positioned on the tube itself (e.g. every centimetre) that can be passed through the nose, down the oesophagus, and into the stomach of a subject (solid-state manometry). Muscle contractions are detected and can be visualized on a computer screen. Both water- and solid-state manometry have advantages and disadvantages. Antroduodenal manometry is available mainly at tertiary referral centres; however, the test is invasive and time consuming and requires skilled technical support. This technique uses a solid-state probe with multiple pressure sensitive channels. Ordinary manometry tubes are positioned transnasally and allow detailed assessment of changes in intragastric pressure over time. However, the technique is designed to measure lumen-obliterating contractions, is expensive, not widely available and therefore only used in the stomach in research settings (1).

To date there is no technique that allows to comprehensively measure the multiple aspects of gastric motility in a standardized fashion that can readily be applied in daily clinical practice. A standard balloon catheter with balloon dimensions optimized for optimal measurement of all aspects of gastric motility while allowing readily passage through the nose would provide a relative comfortable and readily applicable readout of stomach motility.

A variety of balloon catheters have been described that comprise features that may allow pressure measurements in the stomach of a patient (pressure measurement systems). Examples are:

WO2012006625 discloses compliant catheters for abdominal pressure measurement in body cavities. From the details in the patent, it appears that the balloon has a maximum length of 8 cm and a diameter of 3 cm.

WO2008066943 describes an apparatus for light treatment with a plurality of light-emitting optical fibres. The apparatus comprises a catheter with a balloon which can be pressurised. The treatment of stomach conditions is envisaged. Balloons are described that can be inflated in the stomach with the size of the inner stomach (diameter between 2 and 5 cm and length of between 10 and 30 cm).

US2008167607 discloses an enteral feeding catheter for delivering nutrient into a patient's stomach, which may be advanced with its distal tip ahead through the nose or mouth of a patient into the oesophagus and stomach of the patient. The catheter has several lumen that can also be used to inflate several balloons attached to the catheter.

WO2008/154450 describes a device for attaching or maintaining the position of a therapeutic or diagnostic device in a body lumen. The device contains a distal support element for moving an element in the stomach. This device may have a pressure sensor.

WO94/28792 describes an intra-abdominal pressure measurement apparatus. This document is related to measuring pH indirectly by measuring partial pressure of carbon dioxide $pCO_2$, which is not the same as measuring gastric motility. US2013184612 describes a motility manometer system, using motility measurement balloons.

US2017/172778 describes an intragastric device with expandable portions.

None of the above described documents provides devices intended for or even suitable for insertion through the nose. This requirement poses specific challenges, especially for obtaining accurate motility information.

The so-called Blakemore/Sengstaken tubes comprise a first balloon for application in the oesophagus and a second balloon for application in the stomach. The Blakemore/

Sengstaken Tube is described to be designed for emergency control of bleeding esophageal varices and as a diagnostic aid in determining the source and/or extent of hemorrhage into the stomach. They can be introduced orally or through nasal passage.

The Goremedical Q50 Stent Graft balloon catheter is used for temporary occlusion of a large vessel.

Foley (Rusch) catheters are placed through the urethra into the bladder. Once in the bladder a spherical balloon can be inflated to anchor the catheter in place. The largest balloon available has a volume of 50 ml. These balloons are spherical and made of elastic or compliant material such as latex or silicone.

The Mcompass balloon catheter is used for anorectal manometry measurements. This 5 channel disposable catheter is relatively short and has a spherical balloon that can be inflated to 50 ml or maximally 250 ml. The pressure needed to inflate the balloon to more than 100 ml is above 1 psi (6.9 kPa).

The Bakri Balloon Tamponade catheter is used to control and diminish uterus bleeding after delivery.

The prior art devices are not very well suited for passage through the nose and for accurately assessing gastric motility.

SUMMARY OF THE INVENTION

It is an aim of the present invention to provide a balloon catheter that can be introduced via the nose of a person, and that allows measurements of pressure changes related to gastric motility.

With "gastric motility" is meant both tonic and phasic contractions in the proximal and/or distal stomach, or only tonic contractions, or phasic contractions.

It is also an aim of the present invention to provide a kit of parts containing such balloon catheter.

It is also an aim of the present invention to provide a system for obtaining and/or recording and/or visualizing pressure changes and/or gastric motility information.

It is a specific aim of embodiments of the present invention to provide such a balloon catheter, which does not create great discomfort or bloating or nausea or pain to the person.

It is a specific aim of embodiments of the present invention to provide such a balloon catheter, which allows to accurately measure stomach-induced pressure changes of the balloon.

It is an aim of preferred embodiments of the present invention to provide such a balloon catheter that allows detection of a relatively strong pressure exerted upon the balloon, e.g. a pressure in the order of about 100 mm Hg (about 13.3 kPa, about 1.93 psi).

It is an aim of preferred embodiments of the present invention to provide a balloon catheter that allows detection of relatively weak pressure changes exerted upon the balloon, e.g. with a resolution in the order of about +/−1 mm Hg (about 0.13 kPa, about 0.02 psi) or better.

It is an aim of particular embodiments of the present invention to provide such a balloon catheter, which has a reduced risk for causing injuries during insertion (e.g. cuts) and after insertion (e.g. squeezing blood vessels).

It is an aim of particular embodiments of the present invention to provide such a balloon catheter, which provides a reduced discomfort or bloating or nausea or pain (e.g. as compared to a balloon having a target volume larger than 300 ml), without substantially negatively influencing the accuracy.

It is an aim of particular embodiments of the present invention to provide such a balloon catheter which also allows to provide and/or collect substances in the stomach, duodenum or small intestine via the catheter and/or stimulate contractions.

According to a first aspect, the present invention provides a balloon catheter for obtaining pressure values related to gastric motility, the balloon catheter suitable for delivery of one or more inflatable balloons to a stomach of a person via a nose of said person; the balloon catheter comprising: a catheter, a first inflatable balloon and optionally a second inflatable balloon, fixedly attached to said catheter; wherein an external diameter of the balloon catheter, when each of said balloons is deflated, is such that the balloon catheter can pass through a hole having a diameter of about 7.7 mm (23 French), said catheter containing at least a first lumen which is fluidly coupled to the inside of the first balloon via at least one first opening in the surface of the catheter; wherein the one or more balloons are adapted to have an overall non-spherical shape, and for having an outer diameter in the range from 4.0 to 7.0 cm, and for having an effective length from 7.0 cm to 18.0 cm or for having a total inner volume in the range from 90 ml to 330 ml, when each of said balloons is inflated by a pressure of 0.20 psi (or 1.379 kPa) in an environment of 20° C. and 1013 mbar absent a counter-pressure; and wherein each of said balloons is made of a polyurethane material having a durometer in the range from 70 to 100 shore A, or a plastic material having a durometer in the range from 25 to 100 shore D, or a plastic material having a durometer in the range from 50 to 120 rockwell R.

The expression "overall non-spherical shape" means to the total shape of all balloons. In case the balloon catheter has a single balloon, this simply means the shape of that single balloon when inflated with 0.2 psi as specified. In case the balloon catheter has two or more balloons, the expression refers to the combination of the two balloon shapes, when both balloons are inflated with 0.2 psi as specified.

In case the balloon catheter has a single balloon, the expression "total inner volume" means the volume inside said single balloon when inflated with 0.2 psi as specified. In case the balloon catheter has two balloons, the expression "total inner volume" means the sum of the volume of the first balloon and the second balloon when each balloon is inflated with 0.2 psi as specified, thus excluding the space between them.

The following advantages are described for the case of a single balloon, but the skilled person can readily translate them to a multi-balloon situation, for example a balloon catheter with two balloons.

The inventors of the present invention were confronted with the problem of providing a device for accurately measuring gastric motility, which device can be applied via the nose, and which does not create great discomfort or bloating or nausea or pain to the person.

In summary, the proposed solution is based on a balloon catheter having a unique and non-trivial combination of characteristics, which provides a technical solution to a technical problem. It is pointed out that 4 parameters are specified: (1) the balloon diameter (in inflated state), (2) the effective balloon length or total inner volume (in inflated state), (3) the maximum diameter of the catheter plus balloon in deflated state (formulated indirectly via a hole diameter), the (4) hardness of the balloon material.

The "multiple-list" principle is applicable. Moreover, the effects are synergistic because if one of these features is omitted, the resulting balloon catheter is not suitable for the same application, in particular: cannot be introduced via the nose or is unsuitable for accurate gastric pressure measurements, hence cannot be used for the envisioned intensive care applications.

It is an advantage that the balloon catheter can be inserted via the nose of the person, because via the nose is more comfortable for the person than via the mouth, and because such a balloon catheter can be inserted even if the person already has several other devices in his or her mouth (e.g. for breathing devices). This is made possible inter alia by using an inflatable and deflatable balloon, and by choosing suitable dimensions and materials.

It is an advantage that the balloon is deflatable, because this allows that the balloon can be retracted again through the nose, after use.

It is an advantage that the balloon is fixedly attached to the catheter, so that the risk of the balloon disengaging from the catheter can be minimized. The balloon is not intended to be separated from the catheter.

It is major advantage of the combination of the dimensional features and the material hardness features, in other words of the wall properties which are chosen such that the balloon can be inflated to its "target dimensions" using a relatively low pressure of at most 1 psi (about 6.9 kPa), for example lower than 0.75 psi (5.2 kPa), or even lower than 0.5 psi (3.4 kPa), or even lower than 0.4 psi (2.7 kPa), or even lower than 0.3 psi (2.1 kPa), or even lower than 0.25 psi (1.7 kPa). This makes it possible to measure even very weak gastric contractions.

It is another major advantage that the risk of squeezing blood vessels using a balloon which can be inflated to its "target volume" with such a low inflation pressure, is minimal or non-existing. It is noted in this respect that a pressure of about 20 to about 30 cm $H_2O$, or about 2.0 to about 3.0 kPa, or about 14 to about 22 mm Hg or about 0.3 to about 0.4 psi, corresponding to the "endotracheal cuff pressure", is widely accepted to be "safe".

It is an advantage of using a non-spherical balloon, in particular an elongated balloon having a diameter smaller than the effective length, because (for a given balloon volume) such a balloon can be passed easier through the nose.

It is an advantage of using a balloon having a target volume in the specified range, because the surface of such a balloon will be slightly tensioned. This, together with the hardness of the material, will prevent that a compression of the balloon at one location of the balloon, would cause an expansion of the balloon at another location of the balloon (as would be the case for an oversized balloon or a highly flexible balloon) rather than increasing the internal pressure.

Without limiting the invention thereto, this balloon catheter is especially useful for determining if and when and to what degree the stomach of a patient lying in intensive care is active. This knowledge can help to decide if, when and at what speed enteral feeding can be applied to this patient.

The term "plastic material" is used in its normal meaning, referring primarily to synthetic or semi-synthetic organic compounds which are malleable, including primarily organic polymers, but including also variants made of renewable materials such as polylactic acid from corn or cellulosics from cotton linters.

The balloon preferably has an elongated shape with a substantially circular cross section. Preferably the diameter of the balloon is in the range from 4.1 to 6.9 cm and the effective length of the one or more balloons is in the range from 7.1 to 17.9 cm.

The balloon, when in its inflated condition, preferably has an elongated shape, preferably a circular symmetrical shape with a substantially circular cross-section. The 3D shape can be substantially ellipsoid, or can be substantially cylindrical near the middle of the balloon and substantially conical or paraboloid or semi-spherical at opposite ends of the balloon, where the balloon is fixedly attached to the catheter.

The wording that "the balloon catheter can pass through a hole of a certain diameter" is chosen because the balloon is typically crumpled or wrinkled when in its deflated state.

In an embodiment, the at least one first opening comprises at least two or at least three first openings.

It is an advantage of providing multiple openings, because a single opening might be obstructed. By providing multiple openings, the risk of all openings being blocked is reduced, and thus the residual amount of fluid inside the balloon may be further reduced. Or stated in other words: this offers the advantage that the first balloon can be substantially completely deflated before retracting the balloon catheter, after use.

In an embodiment, the balloon is made of a thermoplastic elastomer.

In an embodiment, the balloon is made of a polyurethane (PU).

In an embodiment, the balloon is made of a thermoplastic polyurethane (PUR).

In an embodiment, the balloon is made of an aromatic thermoplastic polyurethane.

In an embodiment, the balloon is made of a thermoplastic elastomer.

In an embodiment, the balloon is made of a polyether block amides (PEBA).

In an embodiment, the balloon is made of nylon (PA).

In an embodiment, the balloon is made of polyethylene (PE).

In an embodiment, the balloon is made of polyethylene terephthalates (PET).

In an embodiment, the balloon is made of a polyvinyl chloride (PVC).

In an embodiment, the balloon is made of polytetramethylene glycol-based aromatic thermoplastic polyurethane.

In an embodiment, the balloon is made of polycarbonate-based aromatic thermoplastic polyurethane.

In an embodiment, the balloon is made of a polyamide, e.g. nylon.

In an embodiment, the balloon is made of Pebax®, a block copolymer variation of PEBA (polyether block amide). (Pebax® is a registered trademark of Arkema, Inc.)

In an embodiment, each of said balloons is made of a polyurethane material having a durometer in the range from 70 to 100 shore A, or from 70 to 90 shore A, or from 80 to 100 shore A, or from 80 to 90 shore A.

The main advantage of using polyurethane with a durometer of at least 70 shore A as compared to softer materials (such as e.g. latex) is that this balloon is less elastic and thus can be used for obtaining more accurate pressure measurements than is possible with e.g. a latex balloon.

It is a further advantage of using a slightly more elastic material (as compared to for example nylon) that the risk of creating cracks or tears due to compression by inserting and crumpling due to insertion through the nose is drastically reduced.

Since these crack or tears might have sharp edges, it is a major advantage that this balloon has a reduced risk of causing tiny wounds, e.g. scratches or scrapes or even cuts during insertion or retraction of the balloon catheter through the nose.

It is a particular advantage of polyurethane balloons having a hardness in the range from about 80 to about 100 shore A that they also allow to accurately measure balloon compressions related to breathing. Tests have shown that, although not absolutely required, the contractions related to breathing can advantageously be used as a reference signal for interpreting the contractions related to the stomach. This may help in the interpretation of the pressure signal to take into account differences between individuals (e.g. light-weight versus heavy weighted, small versus tall, etc.) without performing additional tests or measurements (such as weighting a person). In other words, this may further increase the usefulness of the measurements, by allowing to increase the accuracy of the signal interpretation, although the signal interpretation itself falls outside the scope of the present invention. The interested reader is referred to the co-pending patent application with title "SYSTEM FOR DETERMINING GASTRIC MOTILITY AND FOR FEEDING A PATIENT", filed by the same applicant as the present application, around May 15, 2018, referred to herein as the "co-pending system application".

In an embodiment, each of said balloons is made of a plastic material having a durometer in the range from 25 to 100 shore D, or from 35 to 90 shore D.

It is an advantage of using a slightly harder material because a balloon made of this material is slightly less elastic, and thus has a reduced tendency to absorb a local pressure increase by slightly expanding at another location. Such a balloon catheter may provide slightly more accurate pressure measurements.

In an embodiment, each of said balloons is made of a plastic material having a durometer in the range from 50 to 120 rockwell R, or from 50 to 115 rockwell R, or from 80 to 115 Rockwell R.

It is an advantage of using a slightly harder material because a balloon made of this material is slightly less elastic, and thus has a reduced tendency to absorb a local pressure increase by slightly expanding at another location. Such a balloon catheter may provide slightly more accurate pressure measurements.

In an embodiment, the one or more balloons are adapted for having a total inner volume in the range from 110 ml to 330 ml, or from 135 ml to 330 ml, when inflated by a pressure of 0.20 psi (or 1.379 kPa) in an environment of 20° C. and 1013 mbar absent a counter-pressure.

It is an advantage of a balloon having a target volume of at least 110 ml, because such balloons are very much suited for evoking phase III contractions. Tests have demonstrated that such contractions could consistently be invoked in 50% of the cases.

It is an advantage of a balloon having a target volume of at least 135 ml, because such balloons are even better suited for evoking phase III contractions. Tests have demonstrated that such contractions could consistently be invoked in 60% of the cases.

In an embodiment, the one or more balloons are adapted for having a total inner volume of 160 ml to 290 ml, when inflated by a pressure of 0.20 psi (or 1.379 kPa) in an environment of 20° C. and 1013 mbar absent a counter-pressure.

It is an advantage that a balloon having a target volume of at most 290 ml typically causes less undesirable effects such as discomfort, bloating, nausea or even pain as compared to a balloon of e.g. 330 ml, made of the same material, as can be appreciated from FIG. 10.

In an embodiment, the one or more balloons are adapted for having a total inner volume in the range from 160 ml to 235 ml, or from 160 ml to 210 ml, or from 170 ml to 190 ml, when inflated by a pressure of 0.20 psi (or 1.379 kPa) in an environment of 20° C. and 1013 mbar absent a counter-pressure.

These preferred ranges provide a very high accuracy (e.g. typically less than 5% of HRM contraction time not detected by the balloon), as can be appreciated from FIG. 8 and FIG. 9, while at the same time causing very low undesirable effects such as discomfort, bloating, nausea or pain. It was unexpected that such a high accuracy could be achieved with a balloon catheter according to the present invention.

The range from 160 ml to 190 ml may be a preferred range for people with a relatively small stomach size, e.g. children in the age from about 12 to about 18. The range from 170 ml to 210 ml may be a preferred range for people with a relatively large stomach size, e.g. adults.

In preferred embodiments, the balloon has a target volume in the range from 170 to 190 ml, for example about 170 ml, or about 175 ml or about 180 ml, or about 185 ml or about 190 ml. Such embodiments are believed to be ideally suited for a majority of people, both children and adults.

In an embodiment, the one or more balloons are adapted for having an outer diameter of between 4.3 and 5.5 cm, when inflated by a pressure of 0.20 psi (or 1.379 kPa) in an environment of 20° C. and 1013 mbar absent a counter-pressure.

As can be appreciated from FIG. 8 and FIG. 9, a larger diameter typically offers a higher accuracy, but as can be appreciated from FIG. 10, a larger diameter also typically creates a higher feeling of bloating or nausea. An optimal comprise (for adults) can be reached for diameters in the specified range.

In an embodiment, the one or more balloons are adapted for having an overall shape with an effective length from 7.0 cm to 16.0 cm, or from 9.0 cm to 16.0 cm, or from 11.0 cm to 14.0 cm, or from 7.0 cm to 12.0 cm, or from 9.0 cm to 12.0 cm, or from 7.0 to 14.0 cm, or from 9.0 to 14.0 cm, or from 10.0 to 13.0 cm, when inflated by a pressure of 0.20 psi (or 1.379 kPa) in an environment of 20° C. and 1013 mbar absent a counter-pressure.

In an embodiment, the catheter and the one or more balloons mounted thereto have an external diameter such that, when each of the balloons is deflated, can pass through a hole having a diameter of about 6.3 mm (19 French) or a hole having a diameter of about 5.3 mm (16 French).

The smaller the external diameter (when compressed), and the more flexible the catheter and the more flexible the balloon, the easier the balloon catheter can be inserted via the nose. It is noted in this respect that flexibility of the balloon not only depends on the material being used, but also on for example the wall thickness.

In an embodiment, the catheter per se has an outer diameter in the range from 2.66 mm (8 French) to 7.0 mm (21 French), for example a diameter of about 3.0 mm (9 French) or about 3.3 mm (10 French) or about 3.7 mm (11 French) or about 4.0 mm (12 French), or about 4.3 mm (13 French) or about 4.7 mm (14 French) or about 5.0 mm (15 French), or about 5.3 mm (16 French) or about 5.7 mm (17 French) or about 6.0 mm (18 French) or about 6.3 mm (19 French) or about 6.7 mm (20 French) or about 7.0 mm (21 French).

The smaller the diameter of the catheter per se, the less air volume in the lumen, the easier the balloon catheter may be insertable via the nose.

The larger the diameter of the catheter per se, the more air volume in the lumen, the more difficult the balloon catheter may be insertable via the nose.

The person skilled in the art, having the benefit of the present invention, can find a suitable compromise.

In an embodiment, said catheter extends through a distal end of each of said one or more balloons; and said catheter further contains a second lumen that is fluidly coupled with at least one second opening arranged in the surface of the catheter outside of the balloons, for delivery of a substance or collection of a substance.

This balloon catheter is not only suitable for pressure measurements, but also for providing food and/or collecting substances to/from the stomach or the duodenum or small intestine. This offers the huge advantage that "gastric motility" can be monitored while providing food to a patient, without having to retract and reinsert the balloon catheter.

Preferably the at least one second opening is located between a distal end of the catheter and a distal end of the distal balloon.

Depending on the position of the second opening, the substance can be delivered to, or collected from the stomach, duodenum or small intestine.

In a catheter with multiple lumen, and with openings at different positions, the option can be given (after positioning of the balloon catheter) to either deliver nutrients to the stomach or the duodenum, depending on the "gastric motility" measurement, or to gradually switch over by gradually decreasing the flow rate in one and increasing the flow rate in the other.

In an embodiment, the at least one second opening is located at a distance smaller than 10 cm from a distal end of the one or more balloons for delivery of said substance into the stomach of the person, or for collection of a substance from the stomach of the person.

The expression "distal end of the one or more balloons" refers to "the distal end of the balloon" in case of a single balloon, or to "the distal end of the distal balloon" in case of two or more balloons.

In an embodiment, the at least one second opening is located at a distance larger than 10 cm from a distal end of the one or more balloons, for delivery of said substance into the duodenum or small intestine of the person, or for collection of a substance from the duodenum or small intestine of the person.

The one or more second openings would typically be located about 10 to 50 cm further than the distal end of the balloon (if there is only one balloon) or the distal end of the distal balloon (in case there is more than one balloon).

In an embodiment, the balloon catheter has only a single balloon fluidly connected to said first lumen.

A system using such balloon catheter would measure a single pressure signal, namely the pressure inside the single balloon (also referred to herein as the "first" balloon). An example of such a balloon is shown in FIG. 1 and FIG. 30, and exemplary readout systems are shown in FIG. 32 and FIG. 35.

In an embodiment, the balloon catheter has a first balloon and a separate second balloon; the first balloon being fluidly connected to said first lumen; the balloon catheter further comprising a third lumen comprising at least one third opening fluidly connected with the second balloon; the first balloon and the second balloon being substantially fluidly isolated.

A system using such balloon catheter can measure two pressure signals, namely a first pressure inside the first (proximal) balloon, and a second pressure inside the second (distal) balloon.

It is noted however that absolute hermetic sealing is not required, some leakage (for example a leakage in the order of 1 ml per minute at a pressure difference of about 1.0 psi between the two compartments is acceptable). Such a balloon catheter has the advantage of allowing to measure a pressure at a proximal end, and another pressure at the distal end of the stomach. This allows not only to determine two pressure values, which can be used to detect faults or defects, but also allows to determine the direction in which the stomach contracts.

An example of such a balloon is shown in FIG. 31, and exemplary readout systems are shown in FIG. 33 and FIG. 34.

In an embodiment, none of the first and second balloon (considered alone) is spherical.

According to a second aspect, the present invention also provides a kit of parts comprising: a balloon catheter according to the first aspect, and a first pressure sensor for attachment to a proximal end of the first lumen of the catheter; optionally a second pressure sensor for attachment to a proximal end of the third lumen if present.

The pressure sensor preferably has a resolution better than 10 mm Hg (about 1.3 kPa, about 0.20 psi), or even better than 5 mm Hg (about 0.66 kPa), or better than 2 mm Hg (about 0.27 kPa), or better than 1 mm Hg (about 0.13 kPa).

In an embodiment, the kit of parts further comprises: a control unit operatively connectable to the first and optionally second pressure sensor, and adapted for obtaining pressure information from the first and optionally second pressure sensor.

The control unit may comprise a programmable device, e.g. a processor or a microcontroller device or the like, provided with a computer program for repeatedly obtaining pressure information from the pressure sensor.

According to a third aspect, the present invention also provides a system for obtaining pressure values related to gastric motility, the system comprising: a balloon catheter according to the first aspect; a first pressure sensor fluidly connected to the first lumen for measuring a pressure of the fluid in the first balloon; optionally a second pressure sensor fluidly connected to the third lumen, if present; a control unit operatively connected to the first and optionally second pressure sensor for obtaining pressure information indicative of gastric motility.

When the balloon catheter is inserted in the stomach of a person, and when the balloon is inflated to its target volume, pressure exerted by surrounding organs such as e.g. the stomach and/or the lungs on the balloon results in pressure changes of the fluid, which can be measured by the pressure sensor which is connected to the control unit. These pressure measurements contain gastric motility information.

In an embodiment, the system further comprises a first fluid pump fluidly connected to the first lumen; and optionally further comprises a second fluid pump fluidly connected to the third lumen, if present; the control unit being operatively connected to the first fluid pump for inflating and/or deflating the first balloon; optionally the control unit being operatively connected to the second fluid pump for inflating and/or deflating the second balloon, if present.

The balloon may be inflated by introducing a predefined amount of air volume, or by operating the fluid pump until a target pressure is reached.

The balloon is preferably inflated with a predefined amount of fluid, or with a predefined volume of fluid. The predefined volume which is applied to the balloon may correspond to the above mentioned "target volume" within a tolerance margin of 20%.

After being inflated, the first lumen of the catheter is preferably hermetically closed, so that the amount of fluid in the balloon is substantially constant (the amount of fluid in the catheter itself can typically be ignored).

According to a fourth aspect, the present invention also provides a system for recording gastric motility information, comprising: a system according to the third aspect; a memory and/or a storage device operatively connected to the control unit, the control unit being further adapted for storing the obtained pressure values and/or one or more values derived therefrom, in said memory and/or in said storage device.

According to a fifth aspect, the present invention also provides a system for visualizing gastric motility information, comprising: a system according to the third aspect or the fourth aspect; the system being further provided with an algorithm for analyzing the pressure information, and for extracting gastric motility information; a display device operatively connected to the control unit, the control unit being further adapted for visualizing the obtained pressure values and/or gastric motility information derived therefrom, on said display device.

In an embodiment, the system further comprising at least one food pump fluidly connected to the second lumen, and optionally connected to the fourth lumen, if present; the control unit being operatively connected to the at least one food pump for providing a substance to the person via the second lumen and via the at least one second opening into the stomach, and optionally for providing a substance to the person via the fourth lumen and via the at least one fourth opening into the duodenum or small intestine of the person.

DETAILED DESCRIPTION OF THE INVENTION

Legends to Figures

FIG. (schematic) 1 is a schematic representation of the balloon catheter of the present invention. 1 depicts the inflatable balloon; 2 depicts the catheter; 3 depicts the first (small) lumen fluidly coupled to the first opening inside the balloon which is used amongst others for balloon inflation and pressure measurement; 4 depicts an opening in the surface of the catheter (also referred to as "first opening"); 5 depicts the distal end of the inflatable balloon; 6 depicts the proximal end of the inflatable balloon; 7 depicts the second (large) lumen that can be used for amongst others nutrient infusion and guidewire and that is fluidly coupled with at least one opening 8 (also referred to as "second opening") near the distal end of the catheter, outside of the balloon; 9 depicts the distal end of the catheter; 10 depicts the diameter of the catheter plus the balloon in deflated state; 11 depicts the diameter of the catheter plus the balloon in inflated state; 12 depicts the effective length of the inflatable balloon. The numbers of the elements of the catheter are indicated in the claims. The terms "small" and "large" are used to indicate that the first lumen has a smaller diameter than the second lumen.

FIG. (schematic) 2 is a schematic representation of the position of the balloon catheter (through the mouth—black-line) and the high-resolution manometer (HRM—dark grey line) through the nose during the experiments. But this is not how the balloon catheter of the present invention is to be used. Instead, the balloon catheter of the present invention is inserted via the nose, and the HRM can be omitted.

FIG. (schematic) 3 is a schematic representation of the balloon catheter assembly derived from a sump double lumen catheter using during the experiments. The original sump catheters were manually modified to block the distal end opening of the small diameter lumen by injecting silicone in the distal tip. An opening of the small diameter lumen at the location of the balloon was created by piecing a hole. The polyethylene balloon was mounted on the modified double-lumen catheter so that the small diameter lumen of the catheter has connection to the inner balloon via the pierced hole but not to the inner stomach while the large diameter lumen has connection to the inner stomach but not to the inner balloon. The large diameter lumen has its connections to the inner stomach only at the distal end site of the balloon. The balloon was pasted on the modified catheter using cyanoacrylate glue, furthermore was a silk threat bound around the endings of the balloon around the catheter to ensure the air-tight sealing.

FIG. (schematic) 4 is a schematic representation of the balloon catheter assembly based on a Levin catheter. No modifications of the Levin catheter were made. A second thin single lumen rigid polyethylene (PE) tube was used to inflate or deflate the balloon and to measure intraballoon pressure. The thin PE tube was inserted in the proximal balloon end while attaching the balloon to the catheter using cyanoacrylate glue and a silk threat bound around the endings of the balloon around the catheters to ensure the air-tight sealing FIG. (schematic) 5 is a schematic representation of several balloons that were tested: balloons with different radius (2, 2.5, 3, 3.5, 4 and 4.5 cm) and with different effective length (11 cm and 18 cm), both spherical and non-spherical were tested. Approximate "target volumes" (see definition further) of the inflated balloons are mentioned in the respective cell.

FIG. (schematic) 6 is a schematic representation of PE balloons used in the experiments, which were assembled out of 4 identically cut PE sheets heat-sealed together into 1 sphere/cylinder form. Assembled a cut-through of the balloon is represented on the right.

FIG. (schematic) 7 shows the data analysis for the experiments. From the original pressure (sampled at 1 Hz) a moving minimum over 5 minutes was calculated from a moving median over 30 seconds (not shown). The moving average (over 5 minutes) of this moving minimum was defined as the baseline (grey line). A moving average was calculated over 60 seconds from the original data. The difference between the moving average (60 s) and the moving minimum (5 min) is represented as the delta line (dotted line). Per second a delta value exceeded 30% of the maximum delta value it was flagged as contraction (indicated with an asterix).

FIG. (schematic) 8 shows example 1. Top Figure: Indication of the contractions measured by the HRM in the distal stomach that were not measured by the balloon.

Represented is the number of distal HRM contraction flags (as defined see schematic 6) that were not at the same time met by a corresponding balloon HRM contraction flags divided by the total number HRM contraction flags. Results represented as mean±STDEV (n=3-8). *: significantly different from 0. The legend under the bars represent the radius of the balloon followed by its length between brackets e.g. 2 (sph) is a balloon of 2 cm radius in a sphere form, 2 (11) represents a balloon of 2 cm radius 11 cm long.

Bottom figure: the same data as in the top figure, rearranged by balloon volume. The interrupted line represents an exponential trendline as estimated by Excel for Windows.

FIG. (schematic) 9 shows example 1. Top figure: Occurrence of phase III followed by phase I in a 2-hour measurement (after inflation of the balloon, before start nutrient drink infusion). A score of 1 was given to an experiment in which a phase III and I occurred, a score of 0 when this was not the case. The results are represented as mean±STDEV (n=3-8). Phase III and I always occurred in the balloons with a radius of 2.5 cm and 11 or 18 cm long, when the balloon had a radius of 3 cm and was 11 cm long or had a radius of 4 cm. The legend under the bars represent the radius of the balloon followed by its length between brackets e.g. 2 (sph) is a balloon of 2 cm radius in a sphere form, 2 (11) represents a balloon of 2 cm radius 11 cm long.

Bottom figure: the same data as in the top figure (expressed as %), rearranged by balloon volume.

FIG. (schematic) 10 shows example 1: 4 symptoms (bloating, discomfort, nausea and pain) upon balloon inflation. Symptoms were scored using a Visual Analogue Scale (VAS) of 100 mm. The bars represent the average score (n=3-8) per balloon type. The legend represents the radius of the balloon followed by its length between brackets e.g. 2 (sph) is a balloon of 2 cm radius in a sphere form, 2 (11) represents a non-spherical balloon having a 2 cm radius and being 11 cm long.

FIG. (schematic) 11 shows example 1: satiation scored on a graded scale 0-5 whereby 0 represents no feeling of satiation, 5 represents "the most satiated I have ever felt". Satiation scores were collected at several timepoints during and after nutrient drink infusion. The balloon was deflated 24 minutes after nutrient drink infusion stopped (30 minutes after the start of the nutrient drink infusion). Average of 3-8 scores per balloon type. The legend represents the radius of the balloon followed by its length between brackets e.g. 2 (sph) is a balloon of 2 cm radius in a sphere form, 2 (11) represents a balloon of 2 cm radius 11 cm long.

FIG. (schematic) 12a shows example 2: the volume versus pressure profile in 3 balloons with similar inflated dimensions: about 11 cm long and 5 cm diameter but made of different material: non-compliant polyethylene (black line, open circles), very compliant soft latex (black line with filled black circles) and semi-compliant hard latex (dashed grey line with filled circles). The balloons were inflated 'on the bench' without any external resistance (other than atmospheric pressure).

FIG. (schematic) 12b shows example 2: the effect of externally-applied mechanical pressure on the fluid pressure inside the balloon. 3 balloons with similar inflated dimensions: about 11 cm long and 5 cm diameter but made of different material: non-compliant polyethylene (black line with open circles), very compliant soft latex (black line with filled circles) and semi-compliant hard latex (dashed grey line with filled circles) were inflated to 200 ml for this experiment.

FIG. (schematic) 13 shows the custom setup to measure balloon sensitivity (example 2). An inflated balloon was positioned in the setup that mildy restricted the movement of the balloon. The inflated balloon was connected to a pressure sensor.

On one end of the balloon a construction allowed to push on the balloon with various weights while the other end of the balloon was left free.

FIG. (schematic) 14 shows a schematic representation of the protocol (examples 3). Small black arrows indicate the timepoints at which a breath samples and a Visual Analogue Scale was taken (every 15 minutes after start of the nutridrink infusion).

FIG. (schematic) 15 shows the motility data analysis via example 3. From the original pressure (sampled at 1 Hz) a moving median over 30 seconds was calculated. From this moving median a moving minimum over 10 minutes was calculated (not shown). The Baseline was calculated as the moving average (over 10 minutes from the moving minimum.

From the original data, a moving average over 30 seconds was calculated (not shown). The delta value is the result from subtraction of the baseline from this moving average. The area under the delta value was considered a measure for contraction.

FIG. (schematic) 16 shows the method for the determination of gastric half emptying time (GET½), as described in example 3. Original recovery data is plotted per sample every 15 minutes in FIG. 16a (left figure: black filled circles). An exponential decay curve was fitted through this data from the point at which the data always decreased. From this fit complimentary data was simulated until t=480 minutes. GET½ was calculated from a hyperbolic fit through the cumulative recovery rate data complemented with simulated data (FIG. 16b; figure on the right).

FIG. (schematic) 17—EXAMPLE 3 shows gastric contractility as measured with an inflated balloon (200 ml) and deflated balloon (20 ml) both after treatment with placebo or 60 mg codeine. Contractility was expressed as motility index (MI). The figures represent the average MI data (n=6). Average and standard deviation (stdev) per condition is represented in the table data. Within the inflated condition, treatment (placebo or codeine) had a significant effect on MI (P<0.01). Within the deflated condition, treatment did not significantly affect MI. Both within the inflated and deflated condition time was a significant effect (P<0.001).

FIG. (schematic) 18—EXAMPLE 3 shows the gastric half emptying time (GET½) in 4 different conditions (with an inflated balloon (200 ml) or deflated balloon (20 ml) both after treatment with placebo or 60 mg codeine). The figures represent the average GET½+Standard deviation (n=6). All comparisons between either condition was significant (P<0.05).

FIG. (schematic) 19—EXAMPLE 3 shows the correlation between changes in MI and GET½. When comparing the effect of codeine vs. placebo in the inflated balloon condition it was noted that motility was always decreased while GET½ increased.

FIG. (schematic) 20 shows a schematic of a measurement system comprising the balloon catheter, control unit and readout/user interface (e.g. including a display). The control unit comprises a pressure sensor and a processor. However, the control unit may further comprise an air pump to infuse air in the balloon of the balloon catheter and/or one or more switches or valves, e.g. a three-way-valve to disconnect the air pump and/or the pressure sensor from the first lumen. Furthermore, the control unit may further comprise a food pump to infuse food through the larger lumen of the balloon catheter (as depicted in the figure). Optionally, a computer with software to provide a readout may be coupled to the processor. The computer with software may be used as the only user interface.

FIG. 21 is a schematic representation of several material hardness scales relevant for the present invention. Such scales are known per se in the art, and are provided herein only as an easy reference for the reader.

FIG. 22 and FIG. 23 show pictures of a balloon catheter according to an embodiment of the present invention. In FIG. 22 the balloon is deflated and flattened. In FIG. 23 the balloon is inflated to its "target volume".

Figure 30:
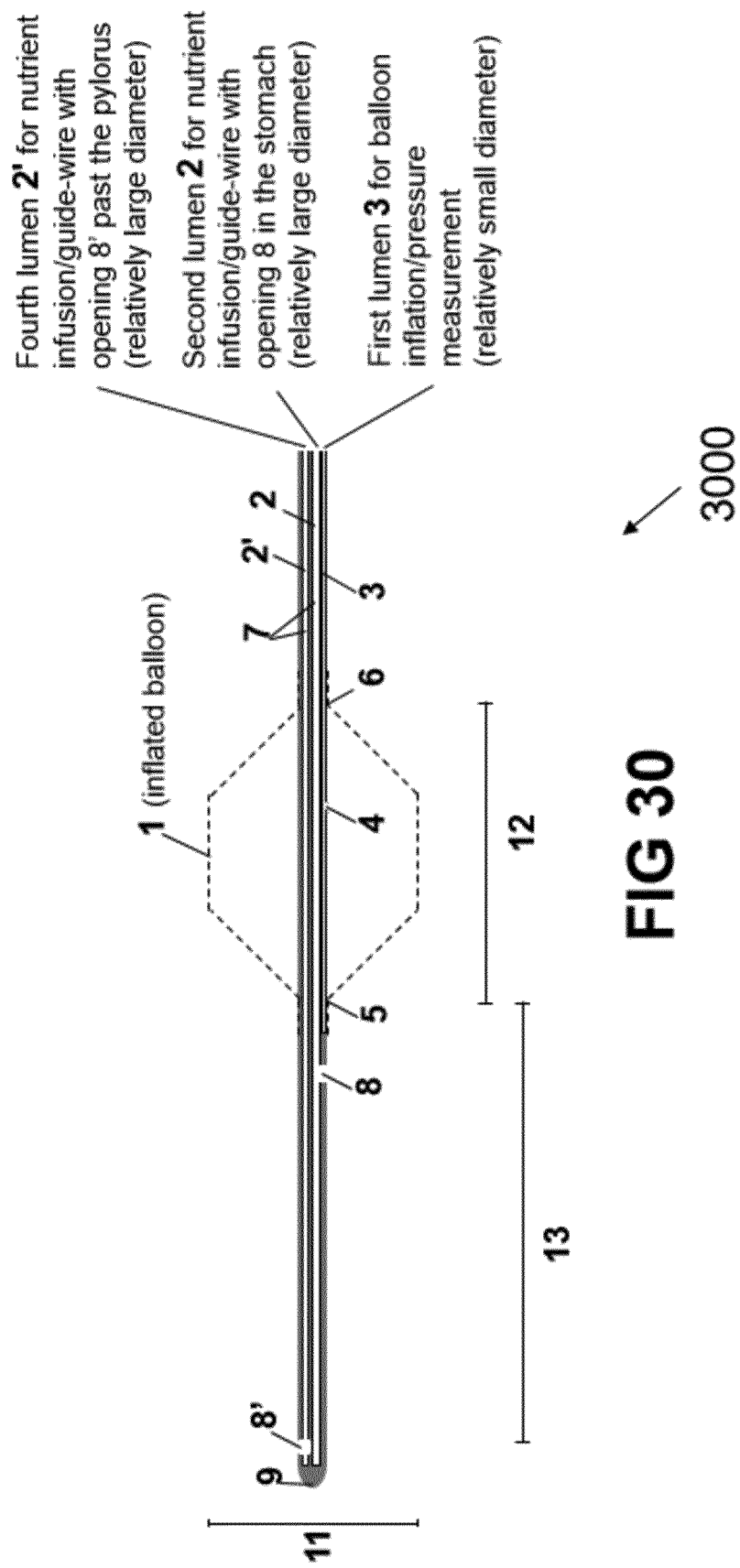

FIG. 30 shows a balloon catheter according to an embodiment of the present invention, having a single balloon and three lumen (referred to as first, second and fourth lumen for consistency of the description and claims): the first lumen for inflating the balloon and for measuring pressure inside the balloon, the second lumen for providing a substance into the stomach, the fourth lumen for providing a substance directly into the duodenum or small intestine.

Figure 31:
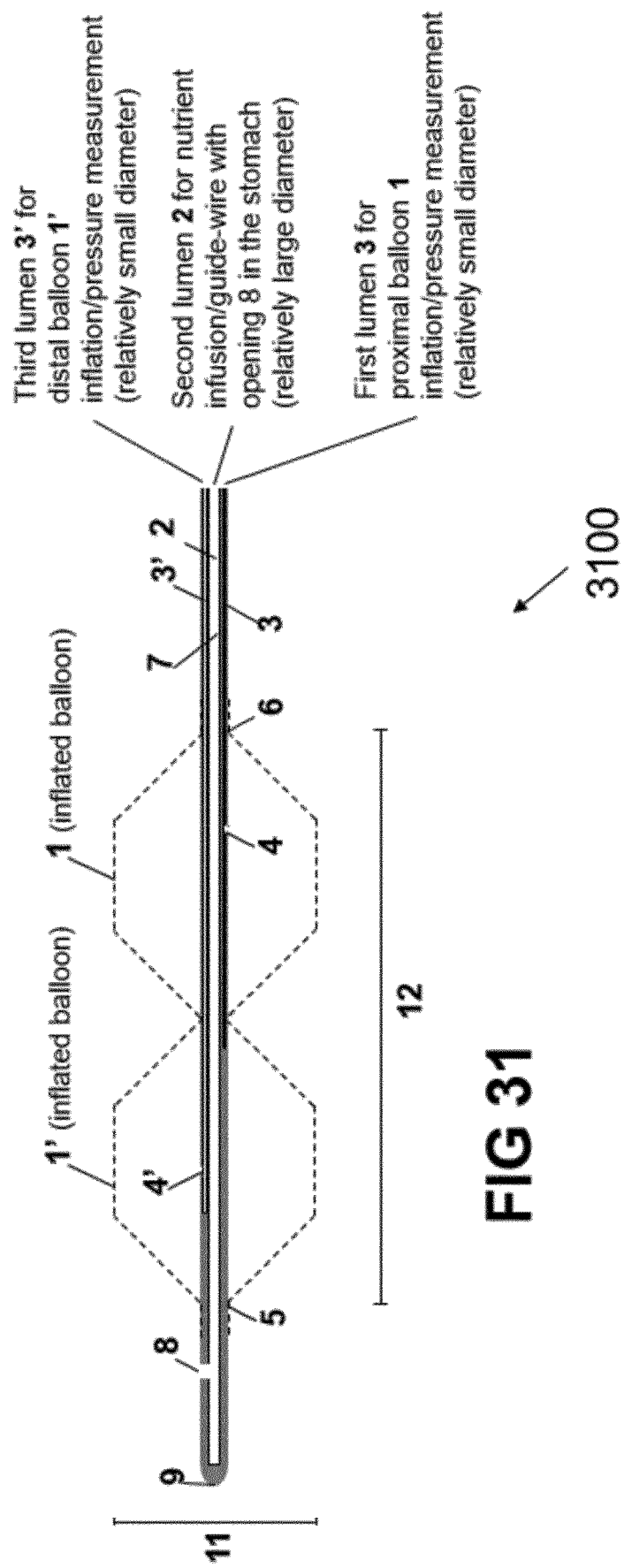

FIG. 31 shows a balloon catheter according to an embodiment of the present invention, having two balloons and three lumen (referred to as first, second and third lumen for consistency of the description and claims): the first lumen for inflating the first balloon and for measuring pressure inside the first balloon, the second lumen for providing a substance into the stomach, the third lumen for inflating the second balloon and for measuring pressure inside the second balloon.

Figure 32:
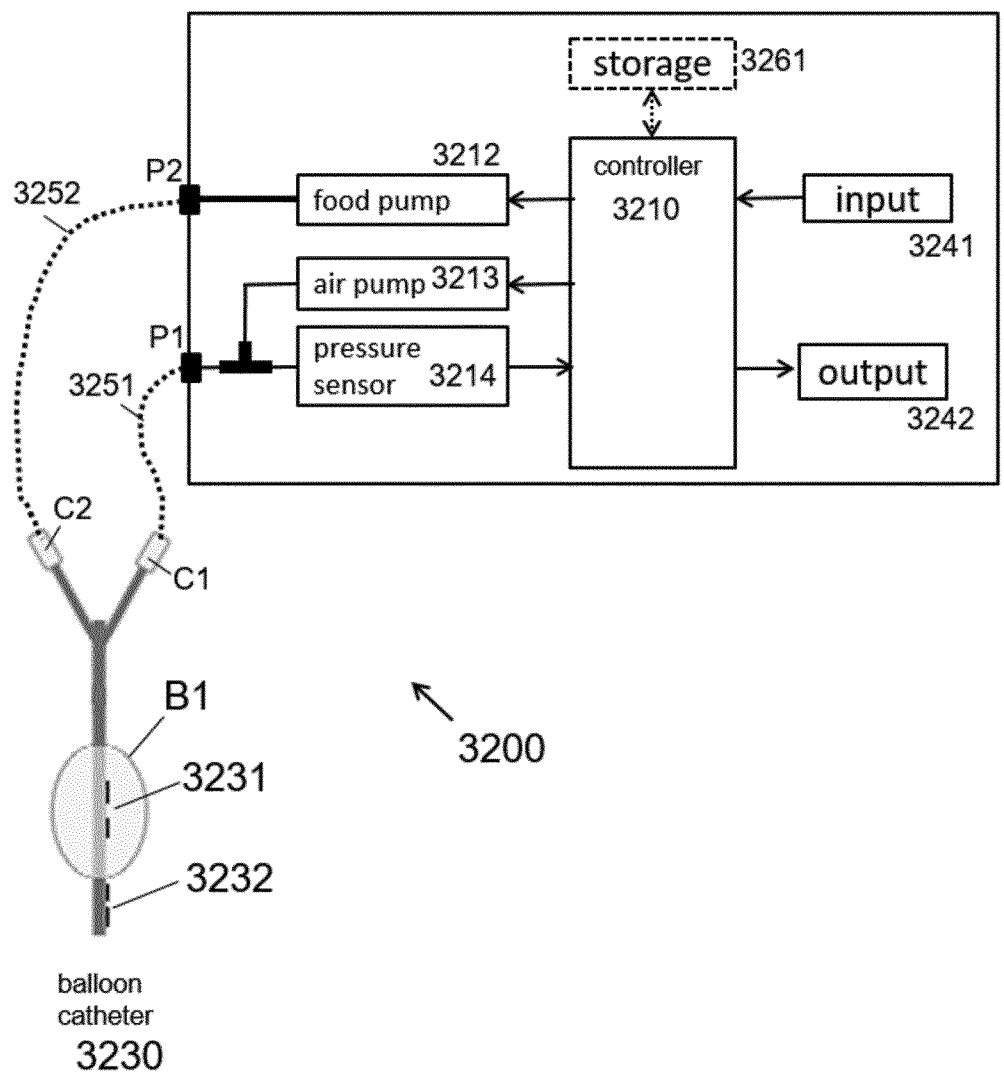

FIG. 32 shows a schematic block diagram of a system according to an embodiment of the present invention. The system comprises a balloon catheter with one balloon and having two lumen: a first lumen connected to the balloon, a second lumen for feeding.

Figure 33:
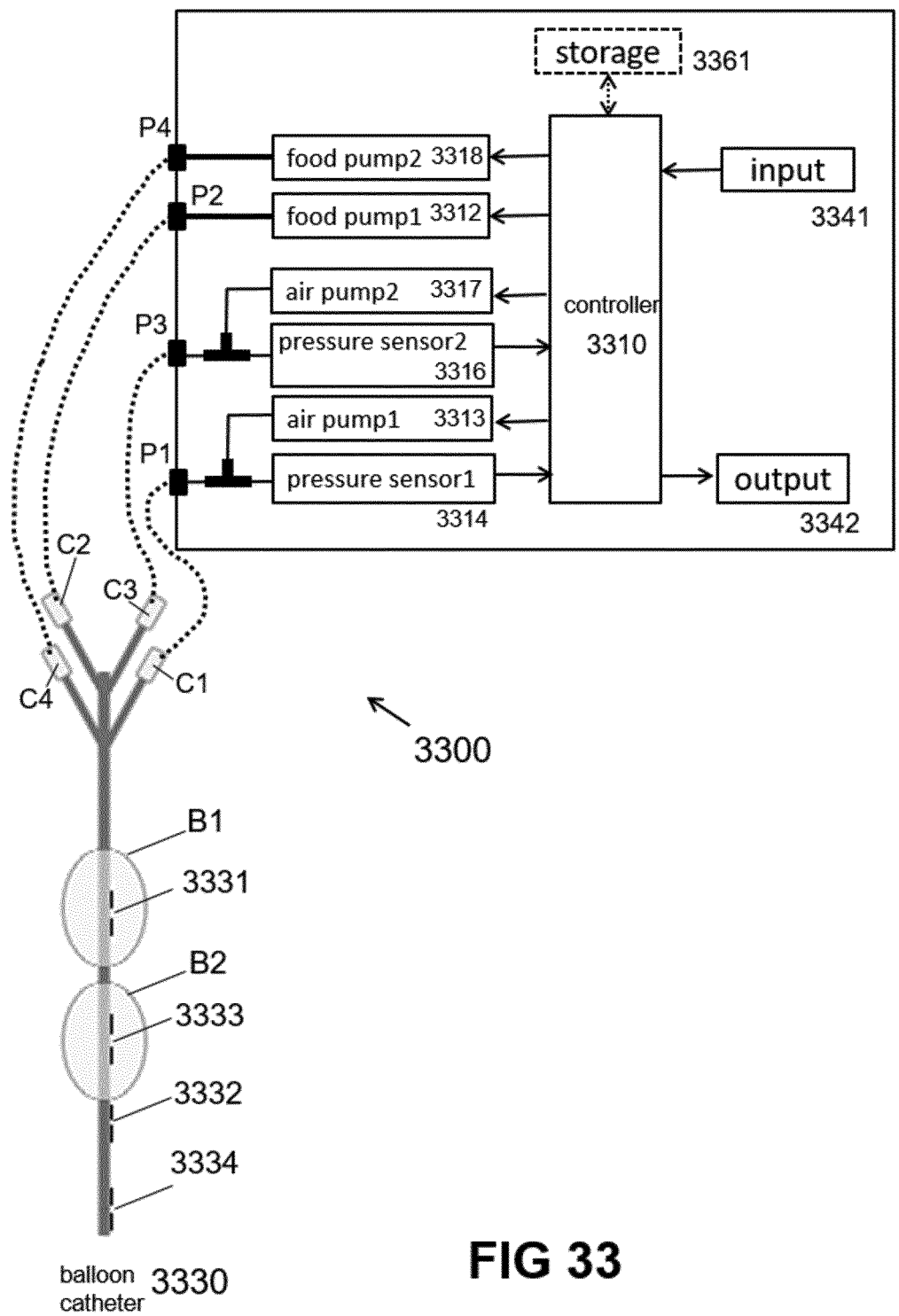

FIG. 33 shows a schematic block diagram of a system according to an embodiment of the present invention. The system comprises a balloon catheter with two balloons and four lumen: a first lumen connected to the first balloon, a second lumen for feeding into the stomach, a third lumen connected to the second balloon, a fourth lumen for feeding into the duodenum or small intestine.

Figure 34:
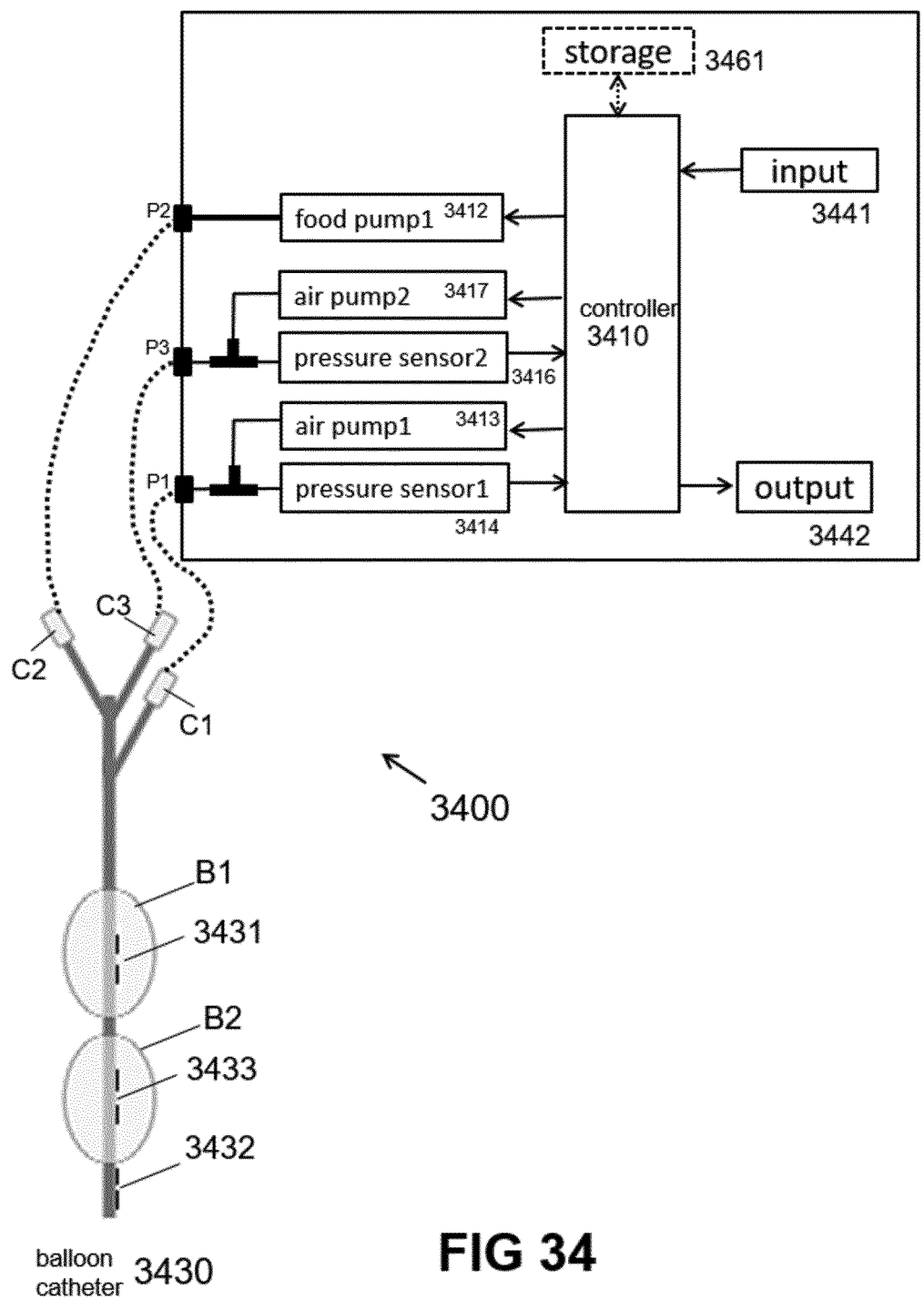

FIG. 34 shows a schematic block diagram of a system according to an embodiment of the present invention. The system comprises a balloon catheter with two balloons and having three lumen: a first lumen connected to the first balloon, a second lumen for feeding into the stomach, a third lumen connected to the second balloon.

Figure 35:
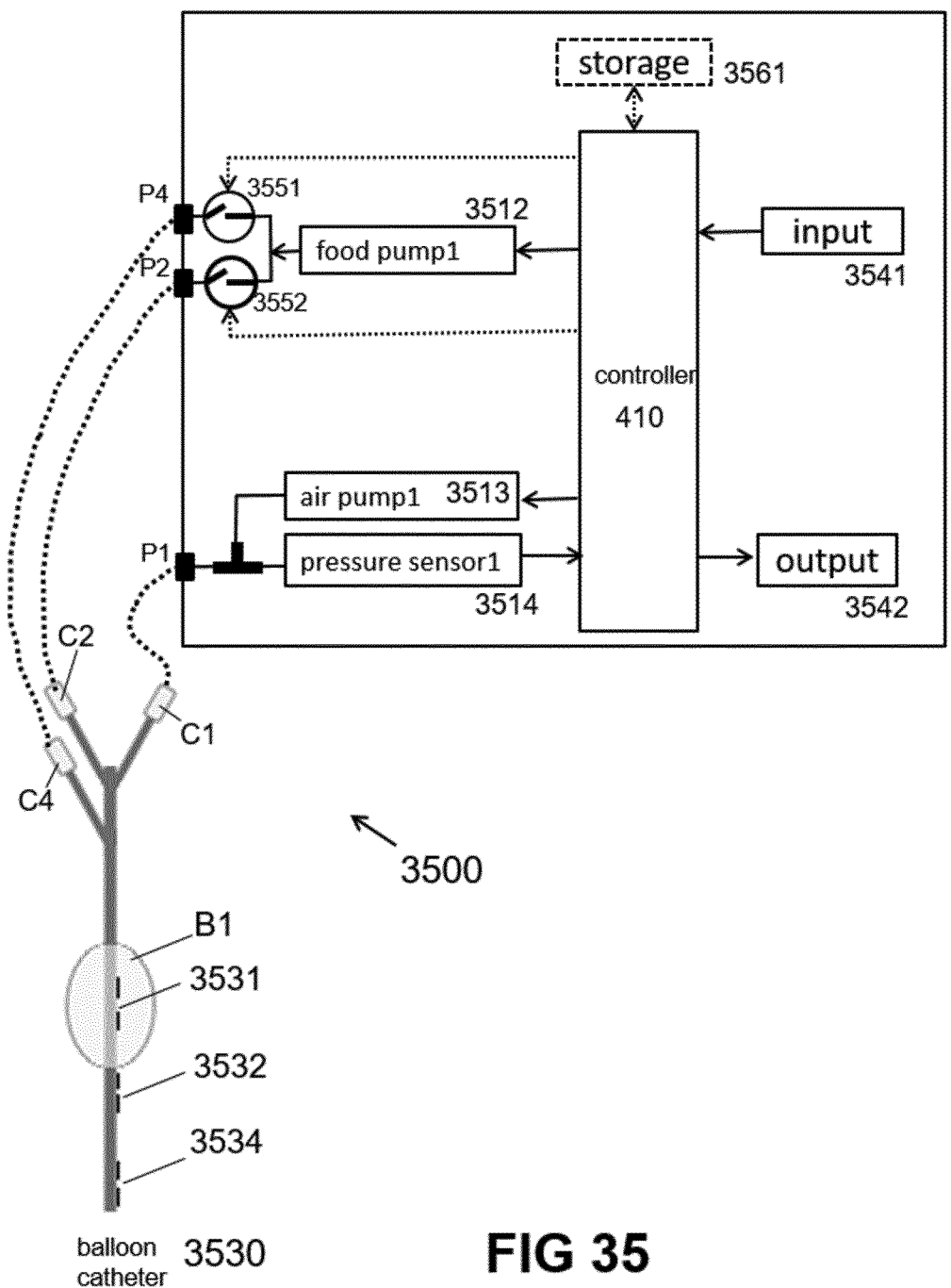

FIG. 35 shows a schematic block diagram of a system according to an embodiment of the present invention. The system comprises a balloon catheter with one balloon and three lumen: a first lumen connected to the first balloon, a second lumen for feeding into the stomach, a fourth lumen for feeding into the duodenum or small intestine.

DETAILED DESCRIPTION OF EMBODIMENTS OF THE INVENTION

The following Detailed Description is merely exemplary in nature and is not intended to limit the invention or the application and uses of the invention. Furthermore, there is no intention to be bound by any theory presented in the preceding Background of the Invention or the following Detailed Description.

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is relevant prior art for the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. For example, if a balloon catheter described herein has a first and a fourth lumen, this does not necessarily mean that it also has a second and third lumen.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination. In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only. Each and every claim is incorporated into the specification as an embodiment of the present invention. Thus, the claims are part of the description and are a further description and are in addition to the preferred embodiments of the present invention.

Each of the claims set out a particular embodiment of the invention.

Particular and preferred aspects of the invention are set out in the accompanying independent and dependent claims. Features from the dependent claims may be combined with features of the independent claims and with features of other dependent claims as appropriate and not merely as explicitly set out in the claims. Thus, the claims following the detailed description are hereby expressly incorporated into this detailed description, with each claim standing on its own as a separate embodiment of this invention.

The following terms are provided solely to aid in the understanding of the invention.

The term "balloon" as used in this application refers to a flexible substrate forming an inflatable body. More specifically, a balloon refers to a flexible bag that can be inflated with air, water, oil or another fluidic medium.

"Compliant, non-compliant and semi-compliant" refers to physical properties of the wall of the balloon. "Non-compliant and semi-compliant" balloons expand to one specific size or size range without noticeable pressure increase. Beyond this specific size or size range the pressure increases with increasing volume. On the contrary "compliant" balloons expand as internal pressure increases.

"Gastric motility" as used in this application can be defined as contraction(s) and/or relaxation(s) of the gastric smooth muscles. In the stomach different types of motility are present:

"Tonic motility" refers to sustained, non-phasic contraction. In between meals the (proximal) stomach maintains a high basal muscle tone. This tone is partially due to the myoelectrical properties of the fundus: the resting membrane potential in the fundic muscles is near or above the mechanical threshold. In addition, muscle tone in the (proximal) stomach is sustained by constant cholinergic input mediated by the vagal nerve. Gastric tone decreases during food intake, and this process of active relaxation is mediated by several different (para)sympathetic reflex pathways that have been shown to decrease the contractile cholinergic input and activate the release of nitric oxide. This reflex, also referred to as gastric accommodation will enhance the storage capacity of the stomach by increasing the compliance of the stomach muscles and thus keeps the intragastric pressure low during food intake.

"Phasic motility" refers to intermittent contractions (or relaxations or both). In the stomach, the phasic contraction rhythm is usually governed by slow wave activity triggered by the gastric pace-maker cells.

"Peristaltic motility" refers to regular and propulsive phasic contractions that move food and chyme through the stomach. Peristaltic contractions follow the slow wave rhythm.

"Migrating motor complex or MMC" refers to a cyclic contraction pattern that takes place during fasting conditions. Indeed, when stomach and small intestines are emptied after a meal a very typical myoelectrical and contraction pattern emerges that is characterized by 3 phases: phase I is a quiescent period with virtually no contractions, phase II consists of random irregular contractions, while phase III is a short burst of regular high-amplitude contractions. Phase III contractions are made up of a group of contractile waves that migrate from the oral to the anal side successively over a constant period, in physiological conditions characterized by an interval of 100-150 minutes during fasting. In man, about half of all phase III onsets are located in the stomach and the other half is located in the duodenum.

When referring in this application to "gastric sensitivity to gastric distention", this means sensitivity as measured by the detection of different symptoms as analysed by a subject which experiences gastric distension. An intragastric balloon can be used to assess sensitivity to gastric distension by inflating the balloon after it has been placed in the stomach while the subject reports symptoms. The latter can be done for example using a visual analogue or graded scale on which the subject has to score different symptoms such as bloating, pain, nausea and discomfort. During this process the balloon can be inflated linearly or stepwise (e.g. steps of 50 ml) and this can be done in a randomized fashion (e.g. the following stepwise randomized sequence: 0 ml-50 ml-250 ml-100 ml-300 ml-200 ml-150 ml in steps of 2 minutes each). The sensation threshold is the minimum volume at which the subject scores more on a symptom as compared to the baseline (0 ml).

The term "biocompatible material" as used in this application refers to biologically evaluated and tested material (such as using ISO10993) with no noticeable negative impact on biological safety. It refers to the ability of the material to be in contact with a living system without producing an adverse effect. With respect to a balloon catheter that will be inserted through the nose and oesophagus into the stomach, the material will have to be tested for extractable and/or leachable components, chemical characterization of the balloon catheter, cytotoxicity, sensitization and irritation reactivity to mucosal membranes according to ISO 10993.

The term "gastroparesis" as used in this application refers to a condition in which the spontaneous movement of the muscles (motility) in the stomach does not function normally. As a consequence, the movement of food from the stomach to the small intestine (gastric emptying) is delayed or stopped.

The term "functional dyspepsia" (FD) as used in this application refers to one of the most comment gastrointestinal disorders encountered in clinical practice. Based on Rome III criteria, FD is defined as the presence of symptoms thought to originate in the gastroduodenal region (early satiation, postprandial fullness, epigastric pain or burning), in the absence of any organic, systemic or metabolic disease that is likely to explain the symptoms. The Rome consensus has also proposed to further subdivide FD into 2 new diagnostic categories of meal-induced dyspeptic symptoms (postprandial distress syndrome [PDS], characterized by postprandial fullness and early satiation) and epigastric pain syndrome ([EPS], characterized by epigastric pain and burning). Several pathophysiological mechanisms have been proposed to underlie symptom generation in FD. The main hypotheses for this pathophysiology include abnormalities of gastric motor function, visceral hypersensitivity due to central or peripheral sensitization, low-grade inflammatory states, altered secretion of gastrointestinal hormones and genetic predisposition.

The term "fluid" as used in this application refers to a continuous amorphous matter that tends to flow and to conform to the outline of its container.

"Distal end of the balloon" as used herein refers to the posterior extremity of the balloon which is, in the context of the present invention, attached to the distal end of the catheter, at a distal position on the catheter as compared to the proximal end of the balloon (see schematic 4)

"Proximal end of the balloon" as used herein refers to the anterior extremity of the balloon which is, in the context of the present invention, attached to the distal end of the catheter, but at a proximal position on the catheter as compared to the distal end of the balloon (see schematic 4);

"Distal end of the catheter" as used herein refers to the posterior extremity of the catheter and which, in the context of the present invention, includes the part of the catheter which is introduced into the stomach and which comprises the balloon of the present invention. Typically, the distal end of the balloon is attached at about 1 cm to about 50 cm distance from the end point of the distal end of the catheter.

"Deflated state" as used herein refers to the state of the balloon of the present invention wherein the balloon is not filled with a fluid, such as, in the context of the present invention, either prior to inflating the balloon with said fluid, or after the fluid has been removed from the balloon. Typically, the volume of the balloon in a deflated state is about 0 ml. In a deflated state, the balloon and catheter can be readily passed through an opening of about 7.7 mm (23 French).

"Inflated state" as used herein refers to the state of the balloon of the present invention wherein the balloon is filled with a gas or a liquid applied to the balloon through a lumen which is fluidly coupled to the inside of the balloon via an opening in the surface of the catheter.

Figure 26:
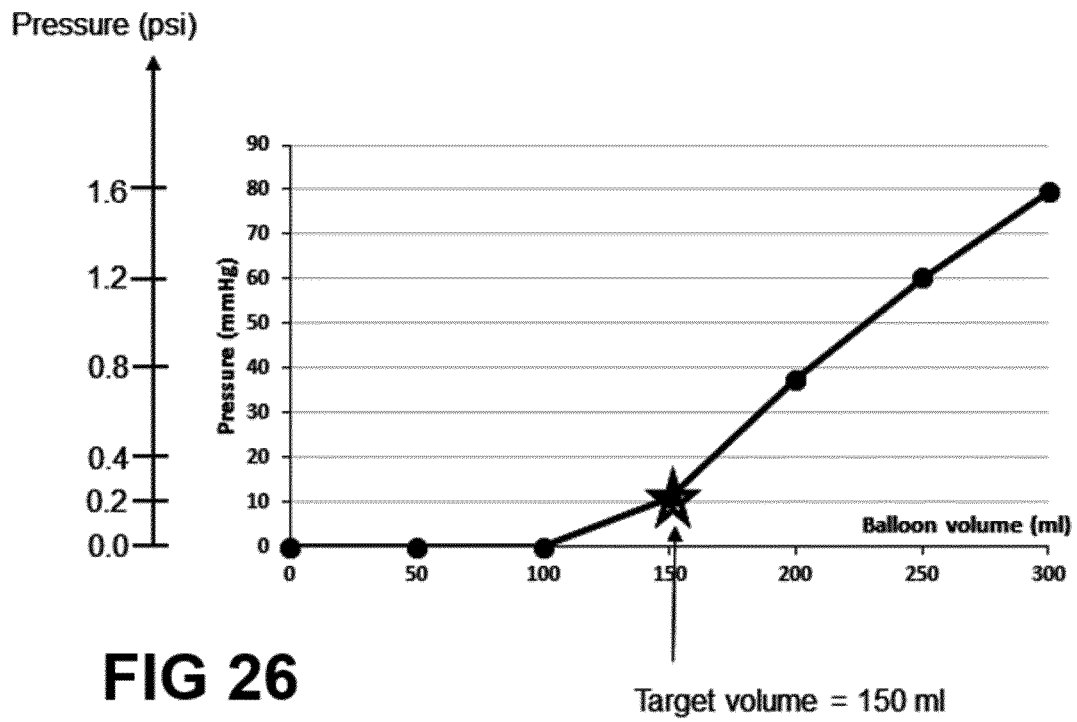
FIG. 26 shows a volume versus pressure profile for an exemplary balloon made of polyurethane with a durometer of 90 shore A, and having a target volume of about 150 ml.
Figure 28:
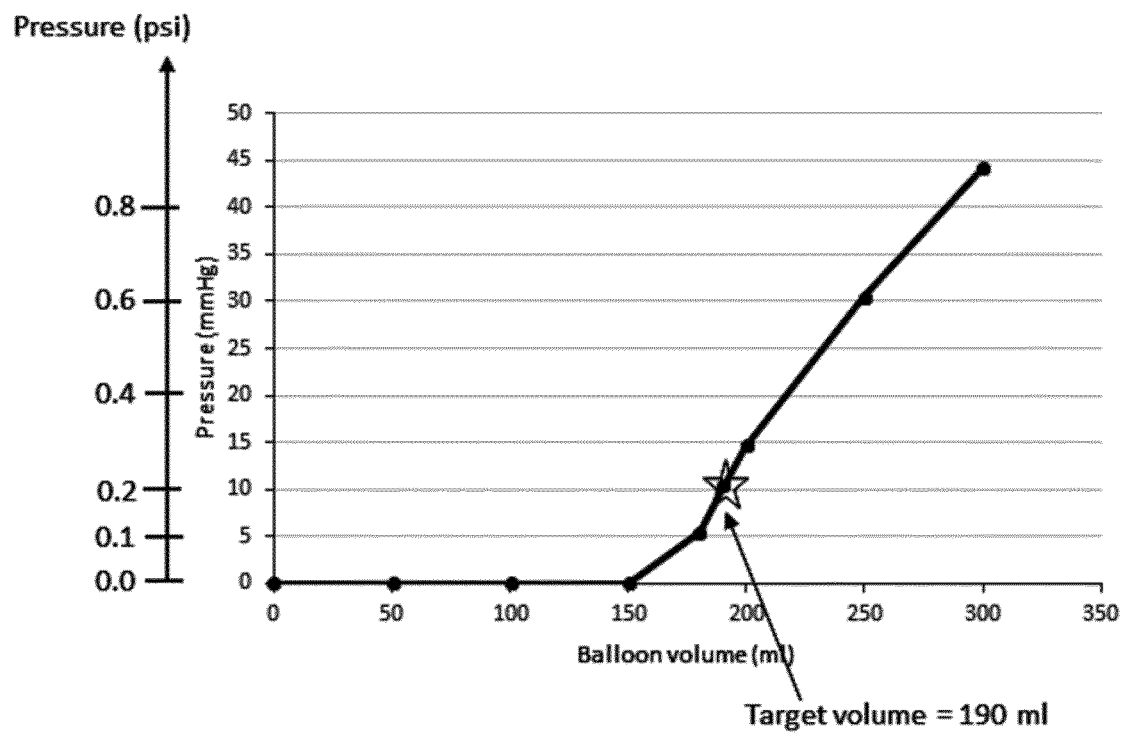
FIG. 28 shows a volume versus pressure profile for another exemplary balloon made of polyurethane with a durometer of 90 shore A, and having a target volume of about 190 ml.

In order to have an unambiguous definition for the "target volume" of a balloon as used in embodiments of the present invention, the expression "the target volume of a balloon if no external pressure is applied" or "target volume of a balloon absent external pressure", or in short "the target volume of a balloon" is defined as the balloon volume that is obtained, when inflating the balloon 'on the bench' (not in a stomach) with a pressure of 0.20 psi (1.379 kPa) in an environment at 20° C. and atmospheric pressure (1 atm=101300 Pa=1013 mbar), as illustrated by the example of FIG. 26 and FIG. 28, after the balloon has been in a deflated stated for a period of at least 24 hours.

As can be appreciated from these examples, the "target volume" corresponds with the approximate location of the "break point" or "point of inflexion" on the P-V curve, but the above definition gives an unambiguous value.

The "target volume" as used herein is also the preferred volume of fluid applied to the balloon when inflating the balloon after being inserted in the stomach for determining gastric motility. For completeness it is noted that optionally temporarily a somewhat higher volume may be applied to the balloon for phase III stimulation or to investigate sensitivity to distension (e.g. in functional dyspeptic patients), but that is not the main target of the present invention.

When reference is made to "applying a pressure X", what is typically meant is that a pressure X higher than atmospheric pressure is applied, as would be reasonably understood by the skilled reader.

With "effective length of the one or more balloons" is meant: "the distance between the proximal end 6 of the proximal balloon and the distal end 5 of the distal balloon". For example, in case of a single balloon, this simply means the length of the single balloon. For example, in case of two balloons, each having a length of 6.0 cm, spaced apart by 1.0 cm, the "effective length of the balloons" is 6.0+1.0+6.0=13.0 cm. When the word "effective" is not mentioned, the reader will understand from the context whether "individual length" or "effective length" is meant.

When using in the detailed description of the invention numbers in bold, we are referring to the numbers as used in FIG. (schematic) 1.

It is noted that the balloon as used in a balloon catheter according to the present invention does not have to be translucent, transparent or optically clear (or contain such portions), although it may.

For the purpose of the products and system of the present invention, the catheter only requires the positioning of a balloon or balloons in the stomach. Additional balloons for positioning a balloon in the oesophagus are not required and can be omitted in the design of a catheter.

A first aspect of the present invention describes balloon catheters suitable for delivery of one or more balloons to the stomach via application by the nose, and suitable for obtaining information related to gastric motility, more in particular, suitable for allowing accurate pressure measurements related to tonic and/or phasic contractions in the proximal and/or distal stomach, preferably without causing great discomfort or bloating or nausea or pain to the person.

Such balloon catheters can be used amongst others for (i) measuring gastric motility through intraballoon pressure changes; (ii) assessing gastric sensitivity to gastric distention in the stomach of a human subject and/or (iii) for stimulating gastric motility and emptying.

An example of such a balloon catheter 100 with a single balloon is shown inter alia in FIG. 22 and FIG. 23 and FIG. 30 and FIG. 32 and FIG. 35.

The balloon catheter 100 comprises: a catheter 2, and an inflatable balloon 1 fixedly attached to said catheter 2. The balloon catheter has the following characteristics:

The external diameter of the balloon catheter 100, when the balloon is deflated, is such that the balloon catheter can bed passed through a hole or opening having a diameter of about 7.7 mm (23 French). In practice this typically means that the balloon can be flattened and/or squeezed and/or compressed and/or crumbled against the outer diameter of the catheter itself, in order to reduce the outer diameter of the balloon catheter to a value of at most 7.7 mm without damaging the balloon.

The catheter 2 contains at least a first lumen 3 (or first channel) which is fluidly coupled to a cavity inside of the balloon 1 via one or more first opening 4, made in the surface of the catheter, and located inside said cavity.

The balloon 1, when inflated, has an overall non-spherical shape, but rather an elongated shape with a central cylindrical portion. The cylindrical portion has a diameter 11 in the range from 4.0 to 7.0 cm.

The balloon 1 has a length in the range from 7 cm to 18 cm, or has a "target volume" in the range from 90 ml to 330 ml.

The balloon is made of a polyurethane material having a durometer in the range from 70 to 100 shore A, or of a plastic material having a durometer in the range from 25 to 100 shore D, or of a plastic material having a durometer in the range from 50 to 120 rockwell R.

An example of such a balloon catheter with two balloons arranged in series, is shown inter alia in FIG. 31 and FIG. 33 and FIG. 34, in which case the two balloons together must satisfy the requirements listed above, in particular, their combined overall shape must be non-spherical (when both balloons are inflated with 0.2 psi), and their effective length should be in the range from 7.0 to 18.0 cm or their total inner volume should be in the range from 90 to 330 ml. The outer diameter of each balloon should be in the range from 4.0 to 7.0 cm.

When used to assess gastric motility the fluid pressure in the balloon, inflated to its target volume and without any external pressure applied, is typically low (e.g. well below 1 psi). However, when used to distend or stimulate the stomach and/or assess sensitivity to distension, the pressure may be slightly increased in order to further inflate the balloon (above 0.2 psi), for example a pressure in the range from about 20 to about 30 cm $H_2O$, or about 2.0 to about 3.0 kPa, or about 14 to about 22 mm Hg or about 0.3 to about 0.4 psi, corresponding to the "endotracheal cuff pressure", which is generally considered to be "safe for emergency care" in terms of not squeezing blood vessels.

Figure 1:
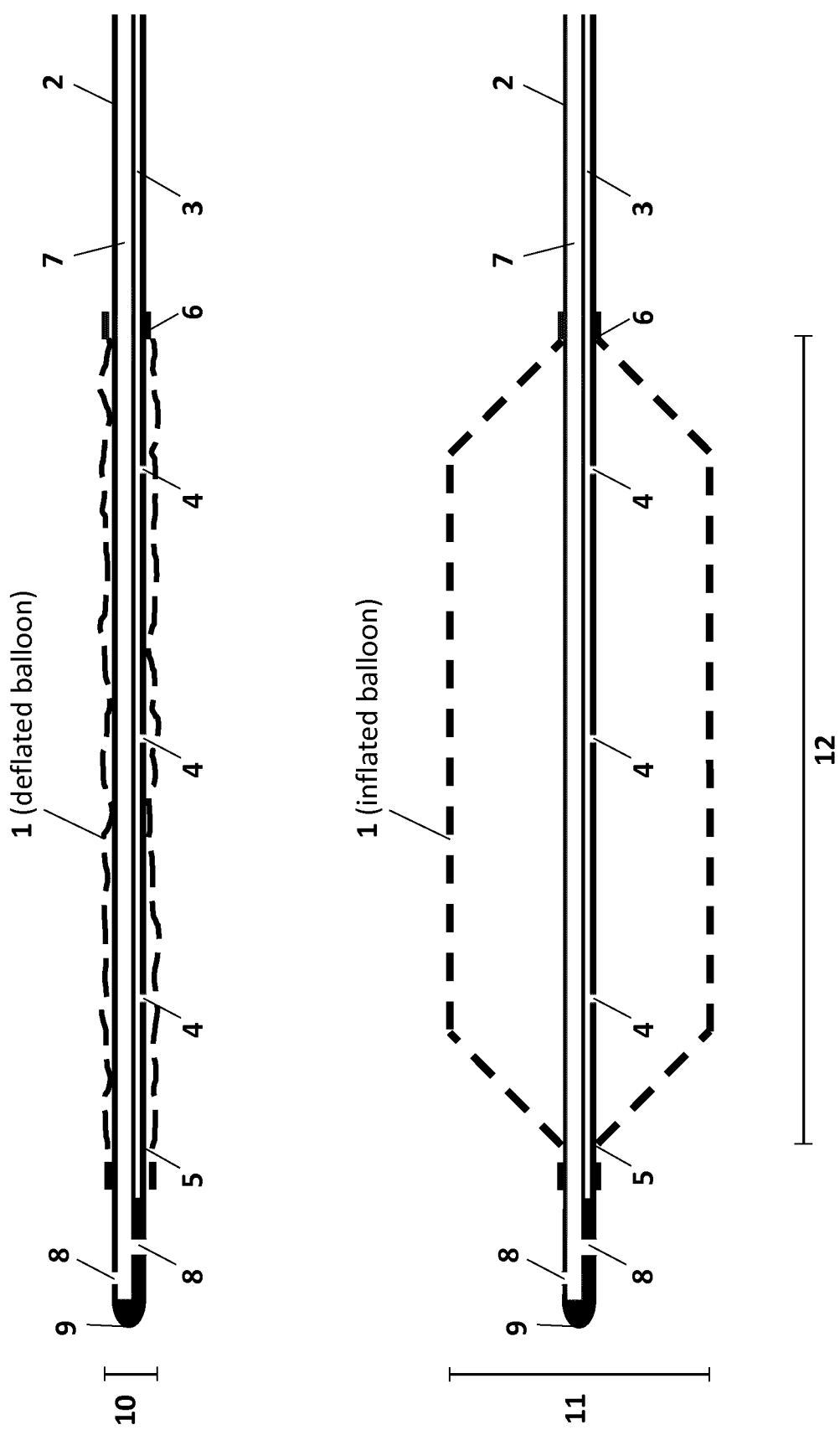
Figure 2:
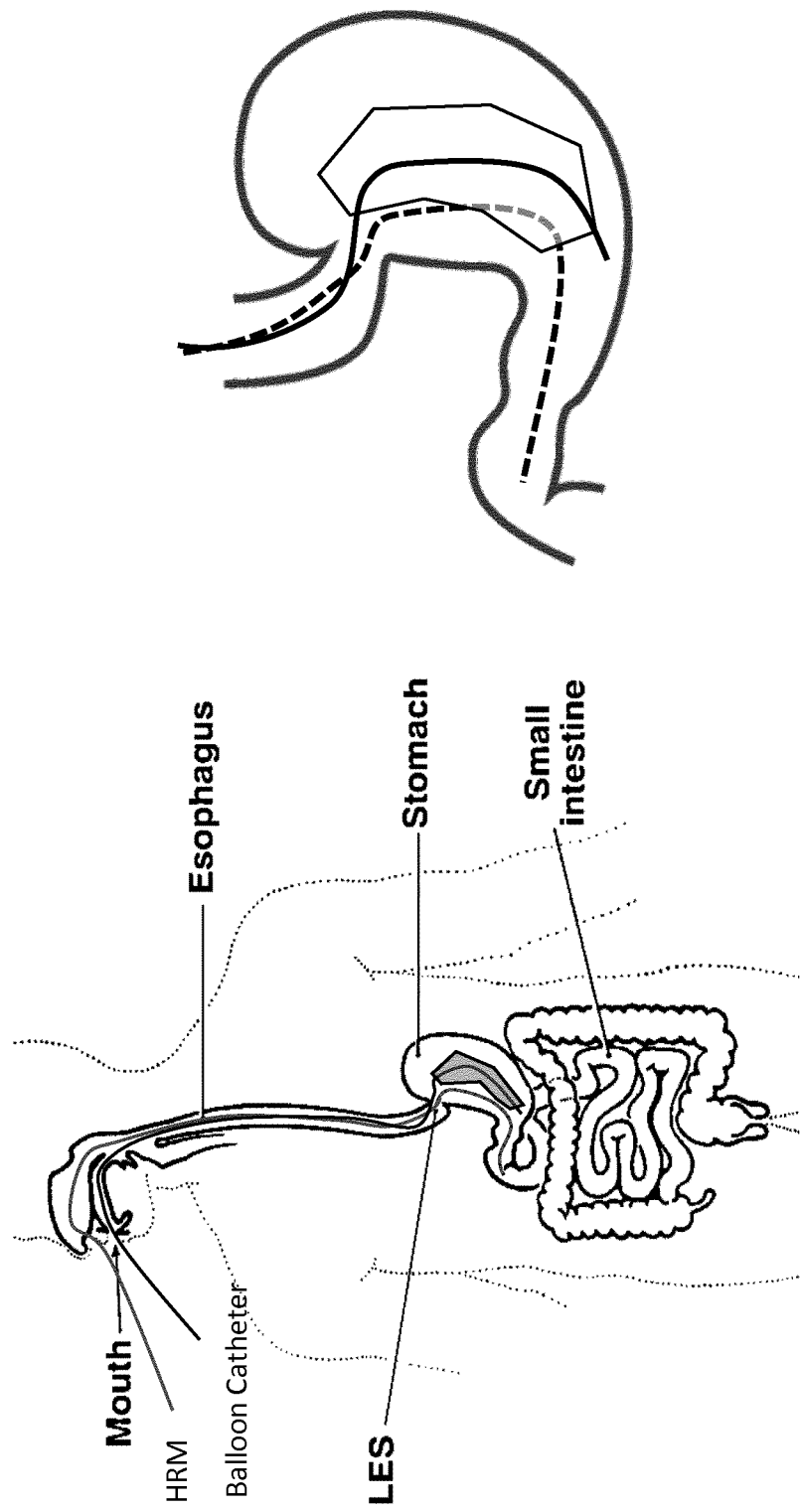
Figure 3:
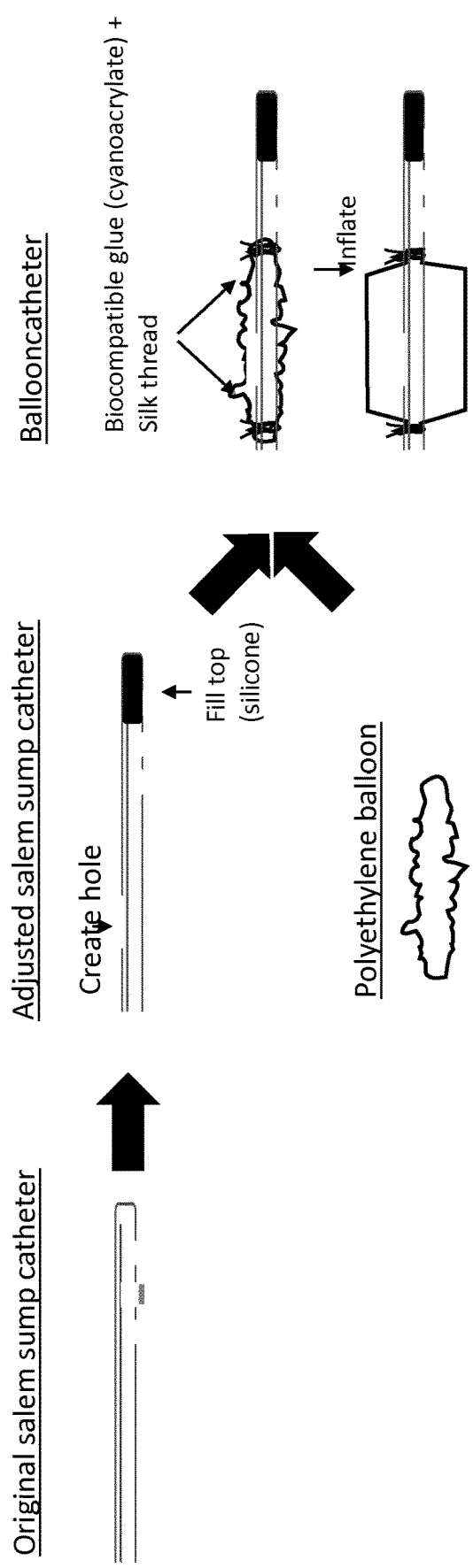
Figure 4:
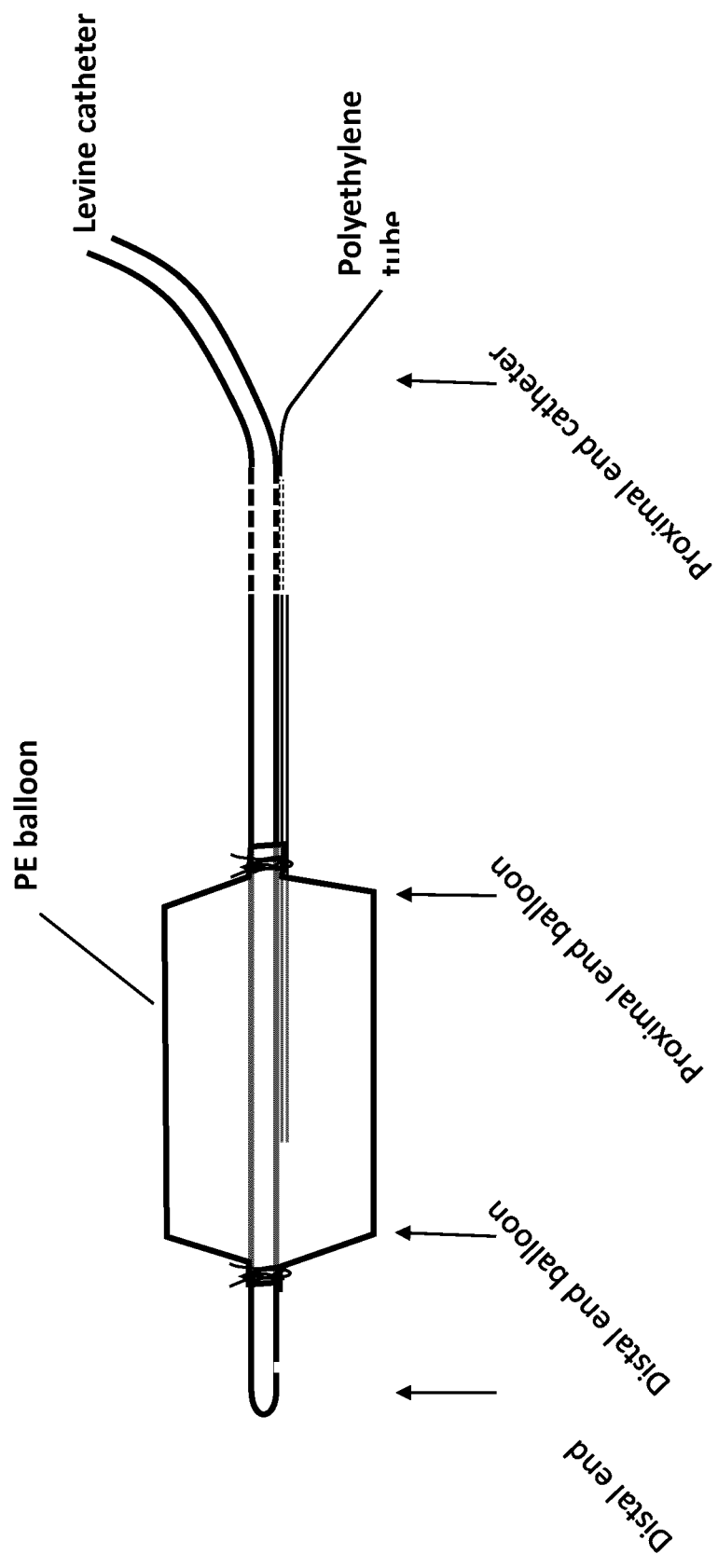
Figure 5:
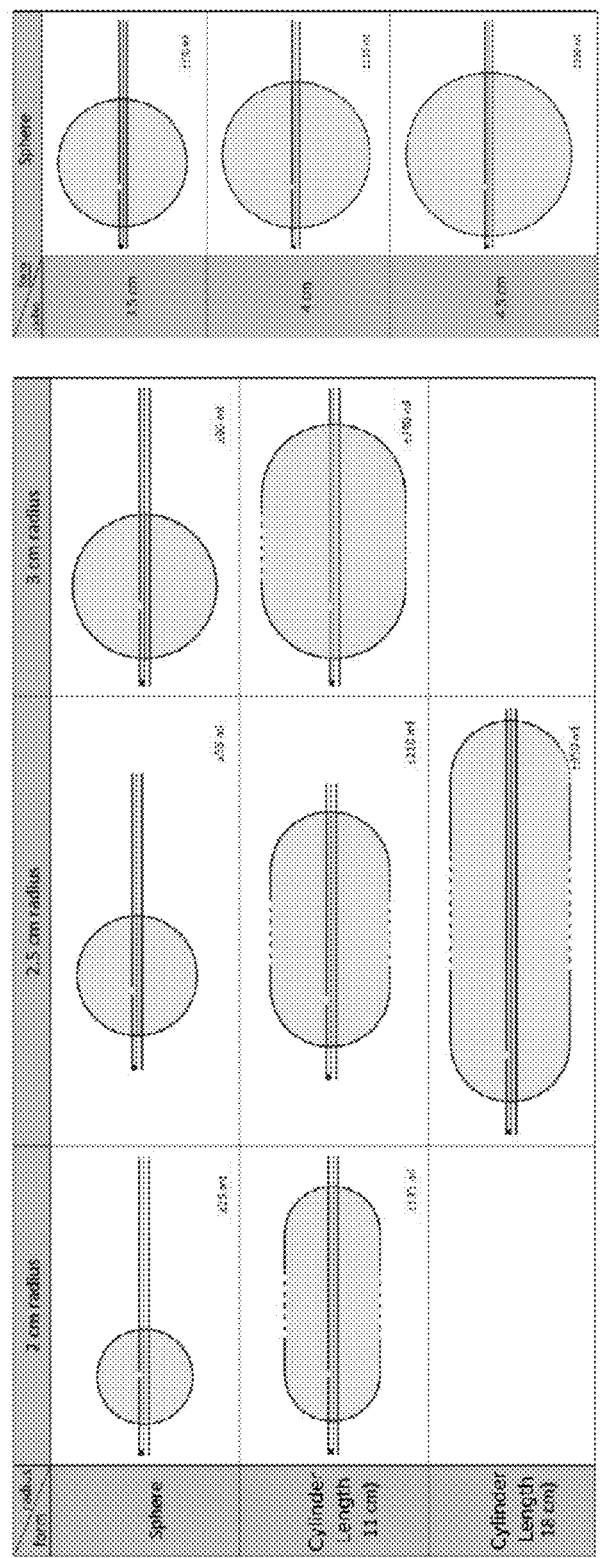
Figure 6:
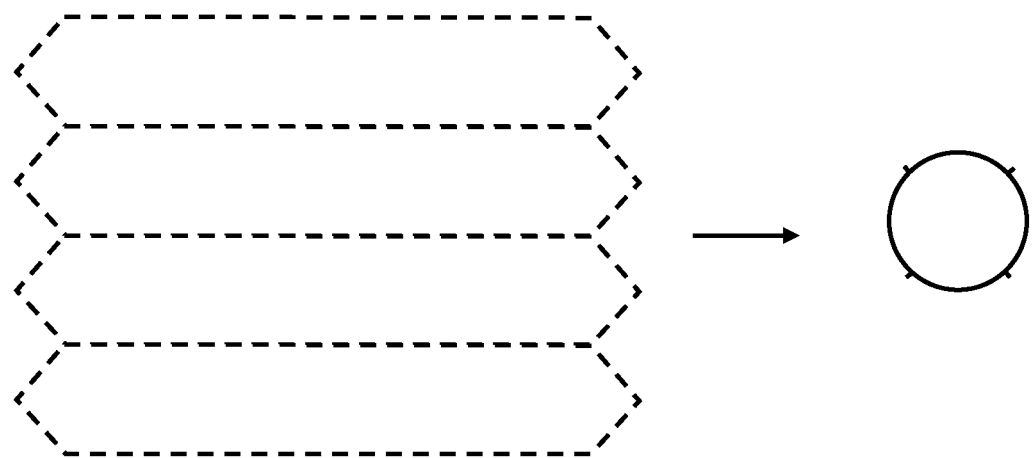
Figure 7:
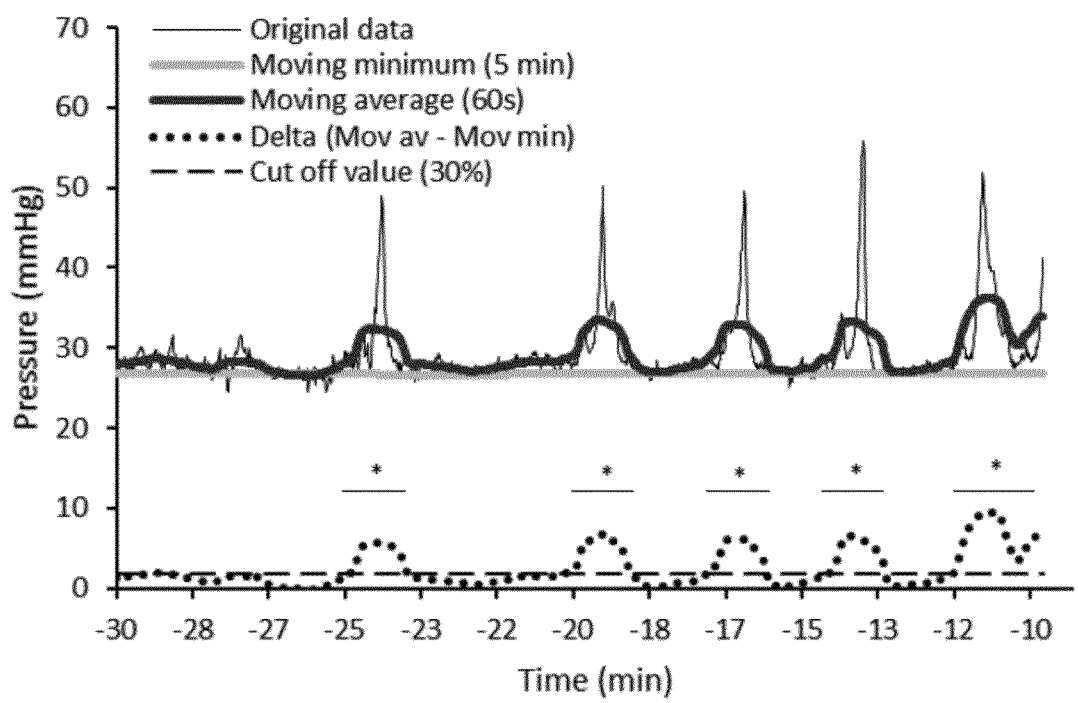
Figure 8:
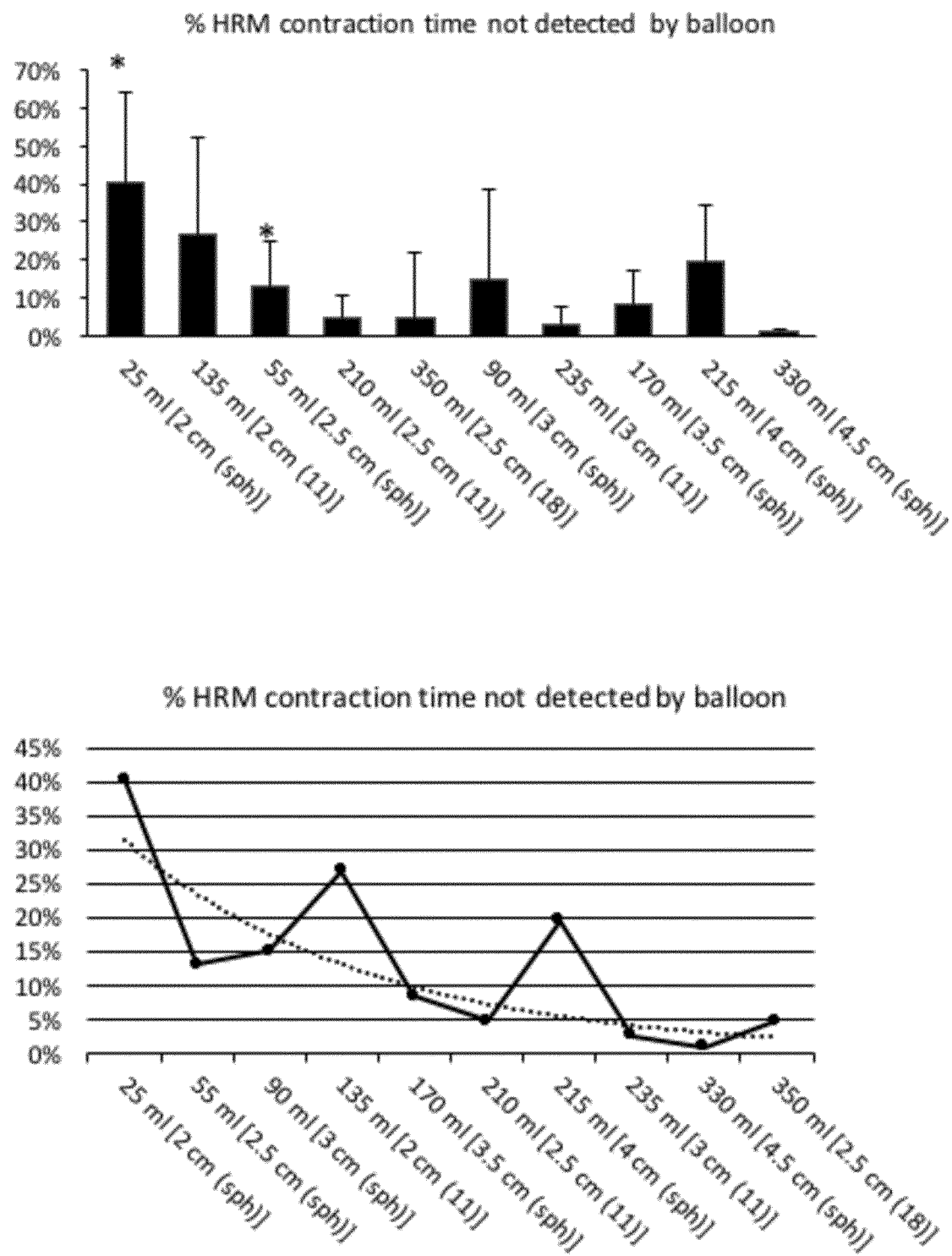
Figure 10:
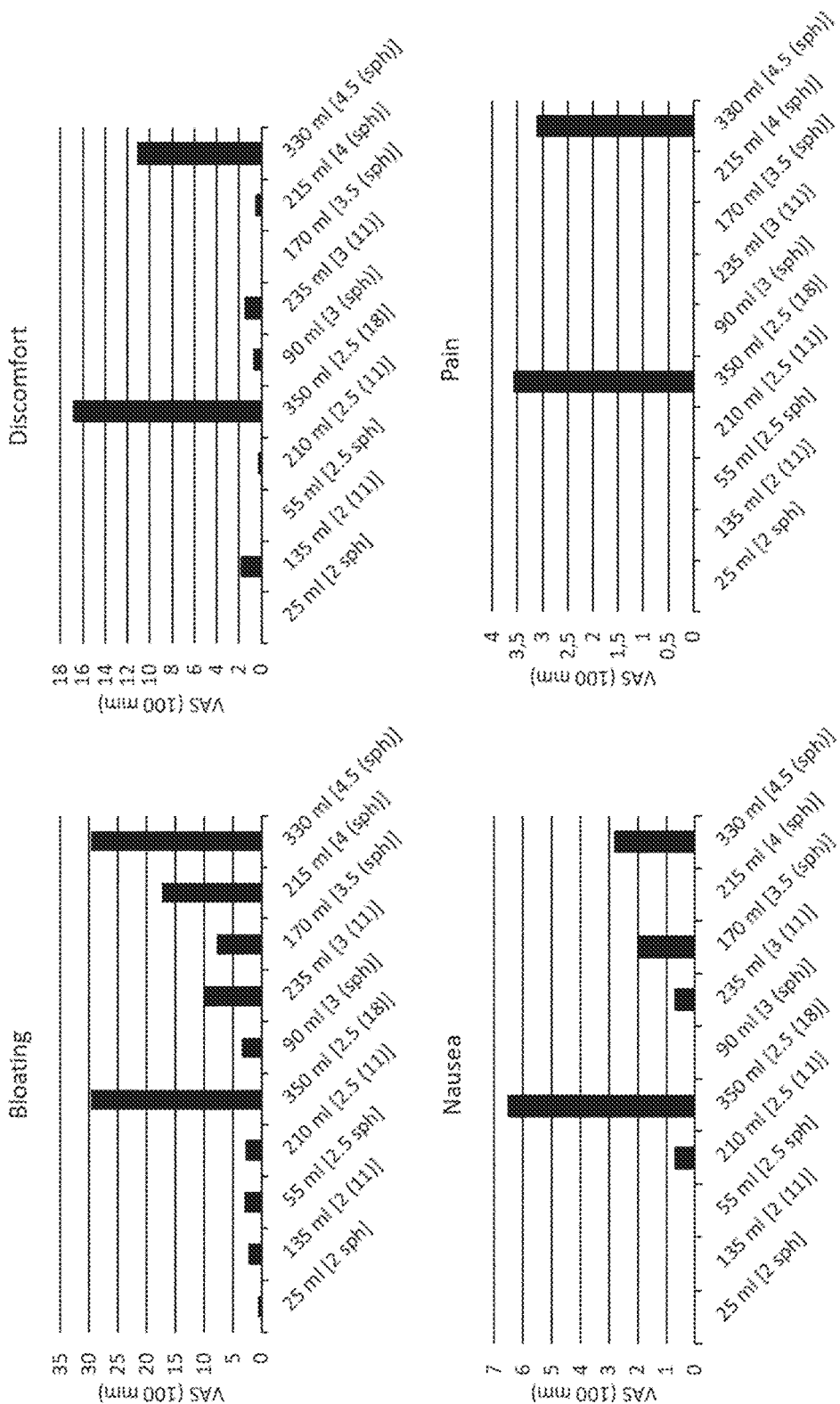
Figure 11:
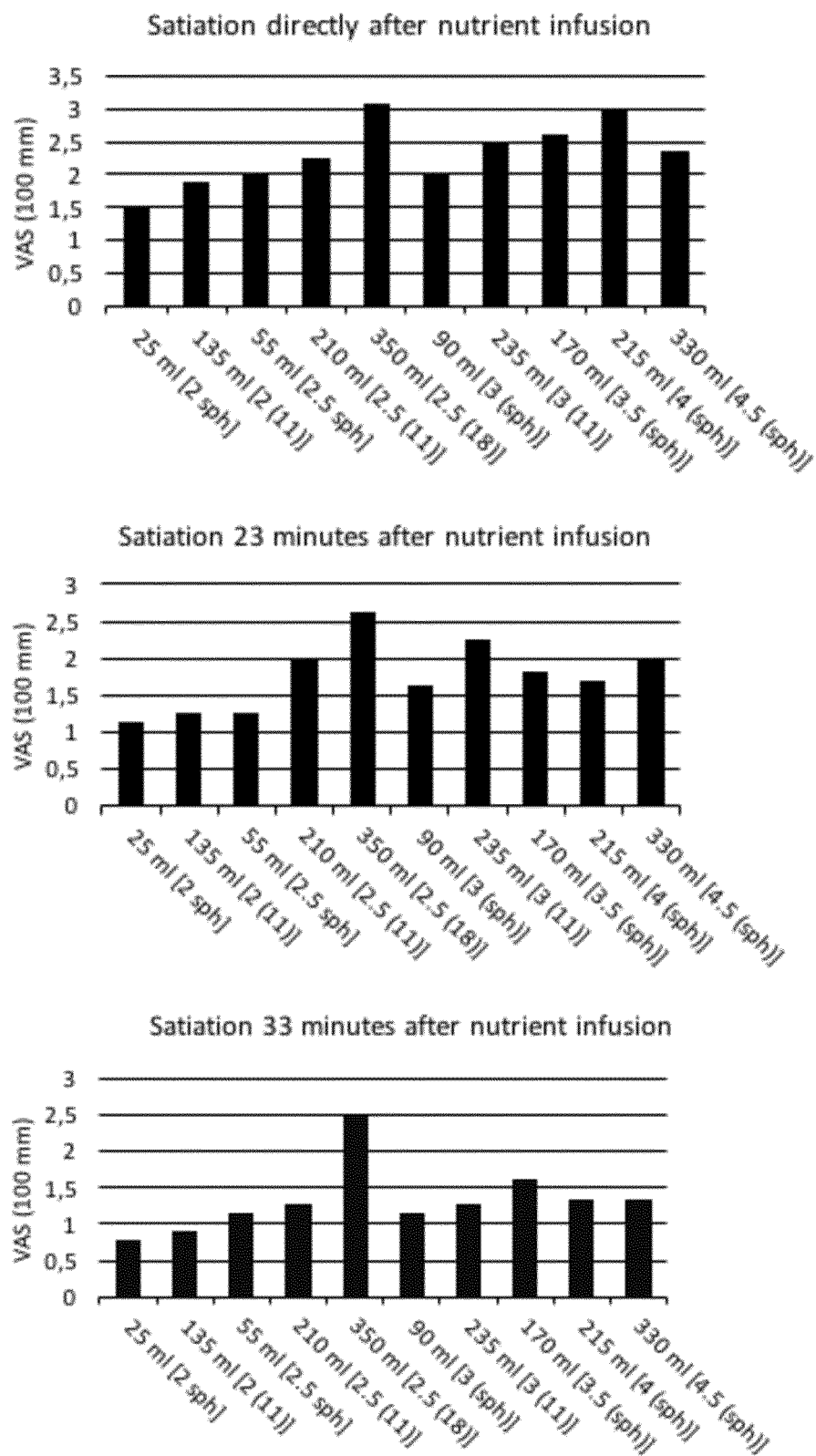
Figure 12:
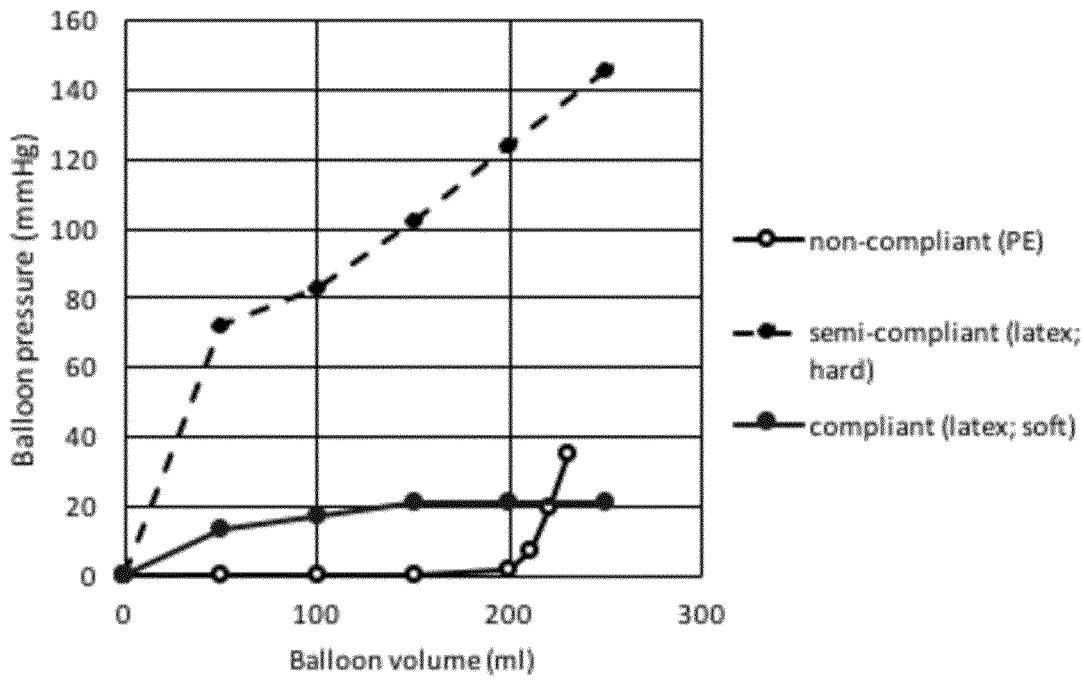
Figure 12:
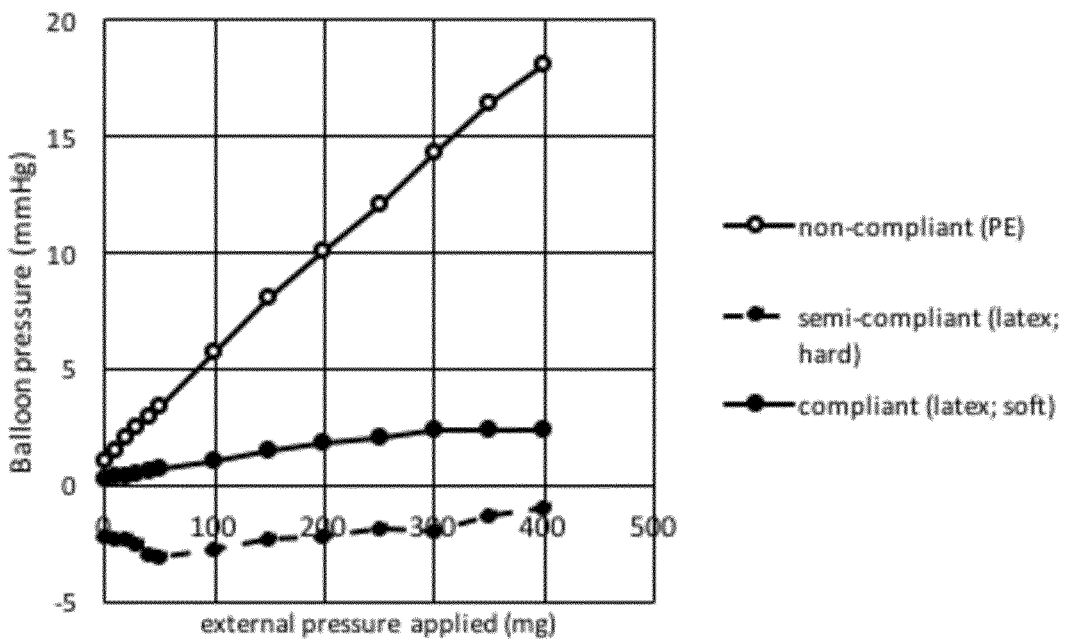
Figure 13:
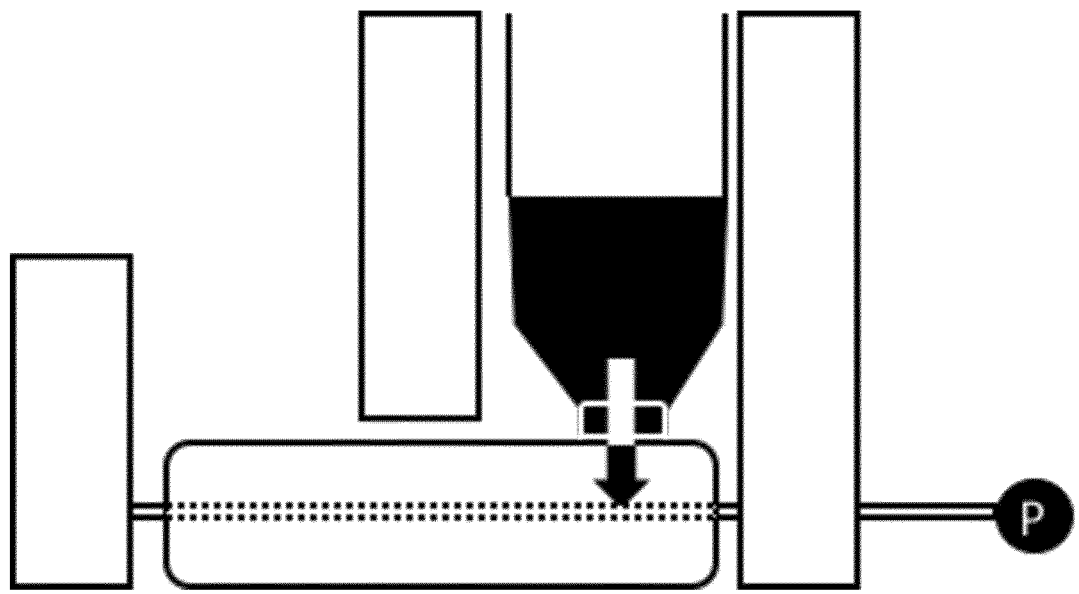
Figure 14:
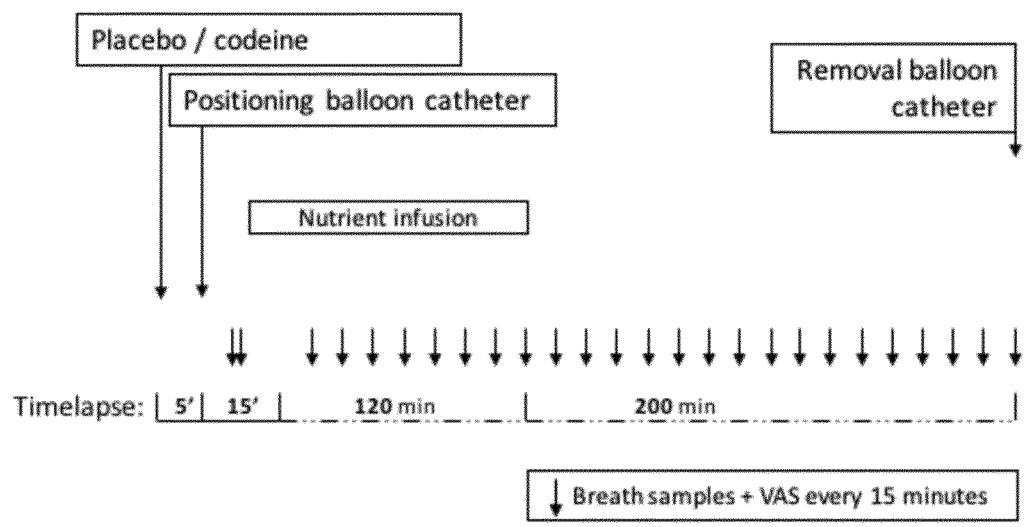
Figure 15:
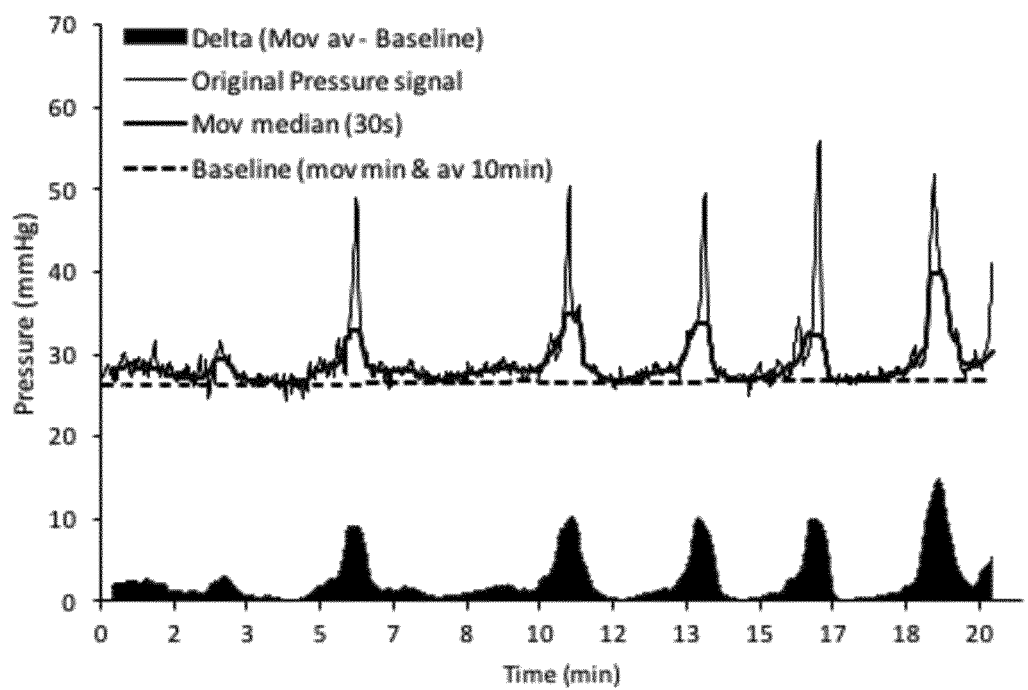
Figure 16:
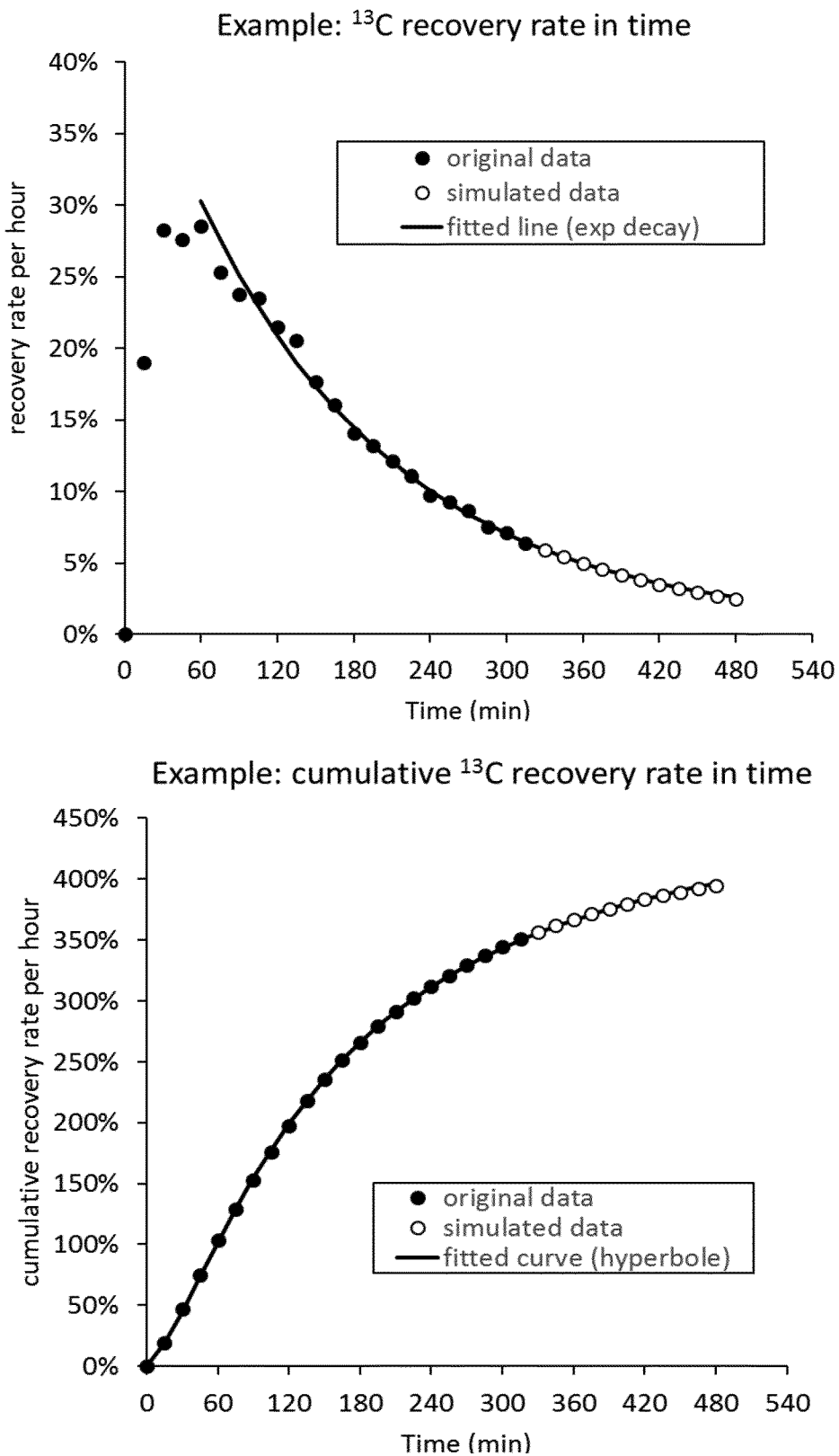
Figure 17:
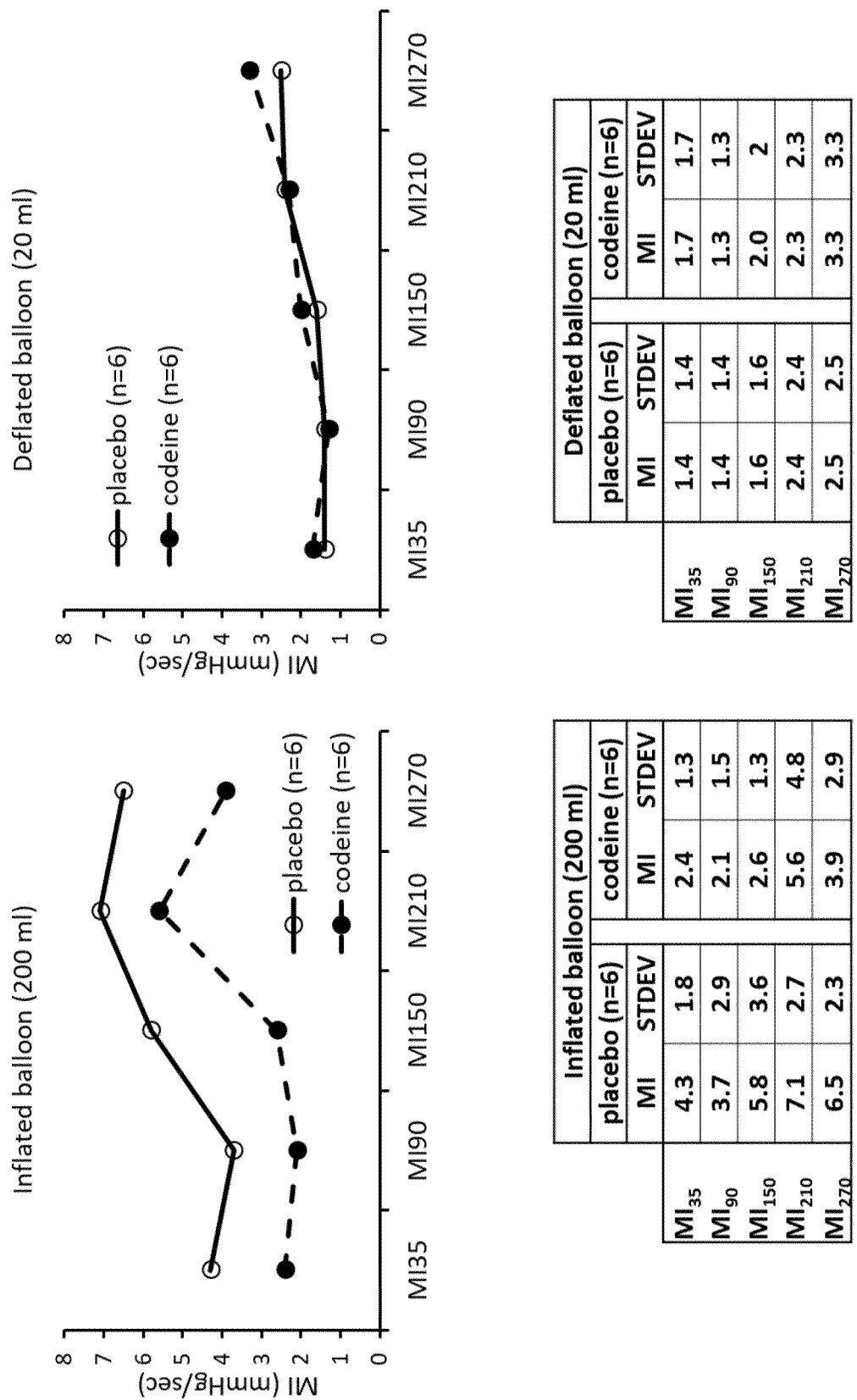
Figure 18:
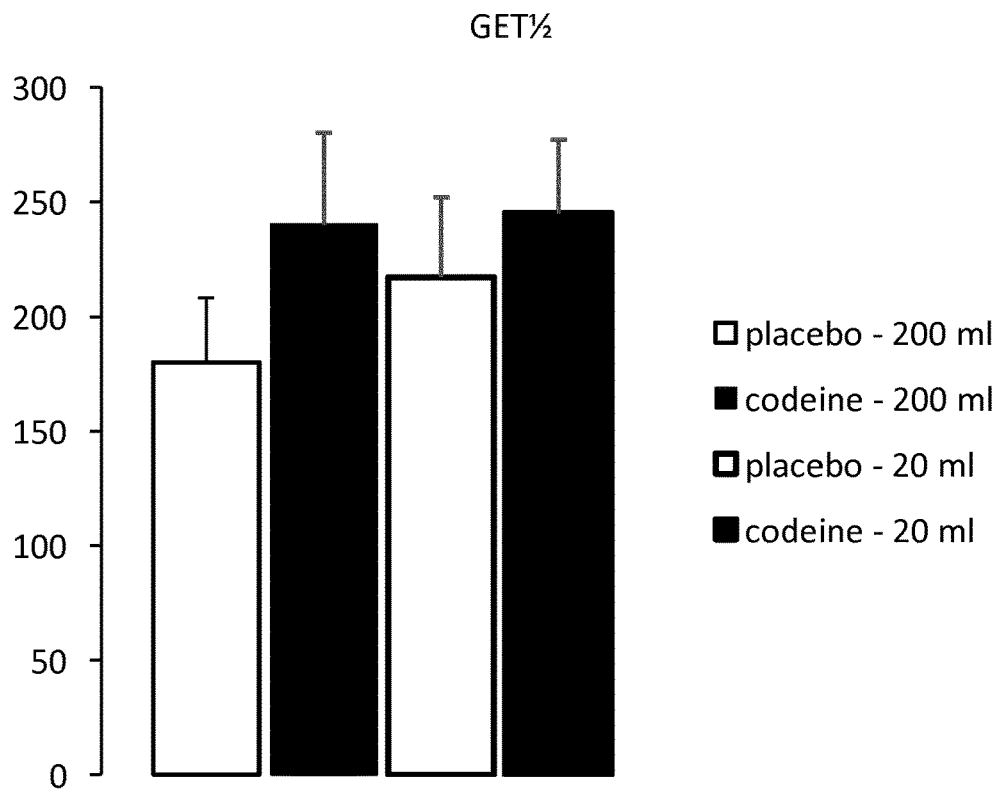
Figure 19:
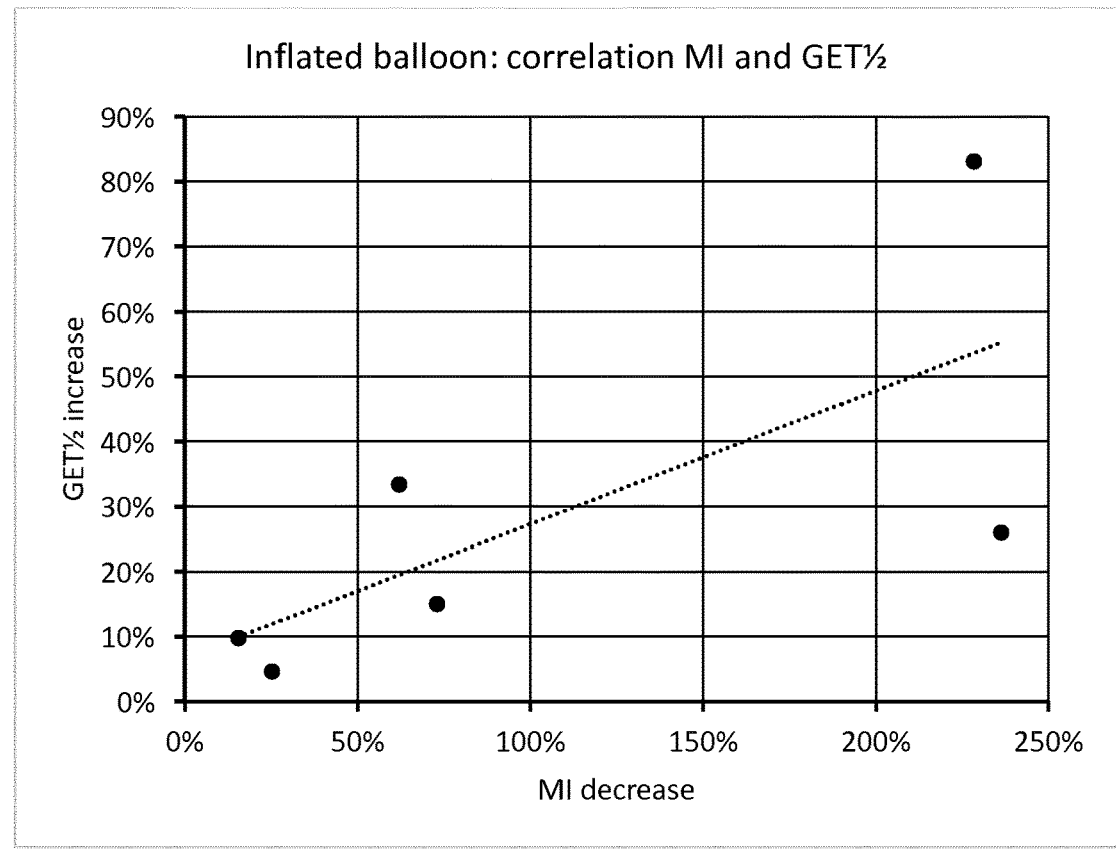
Figure 20:
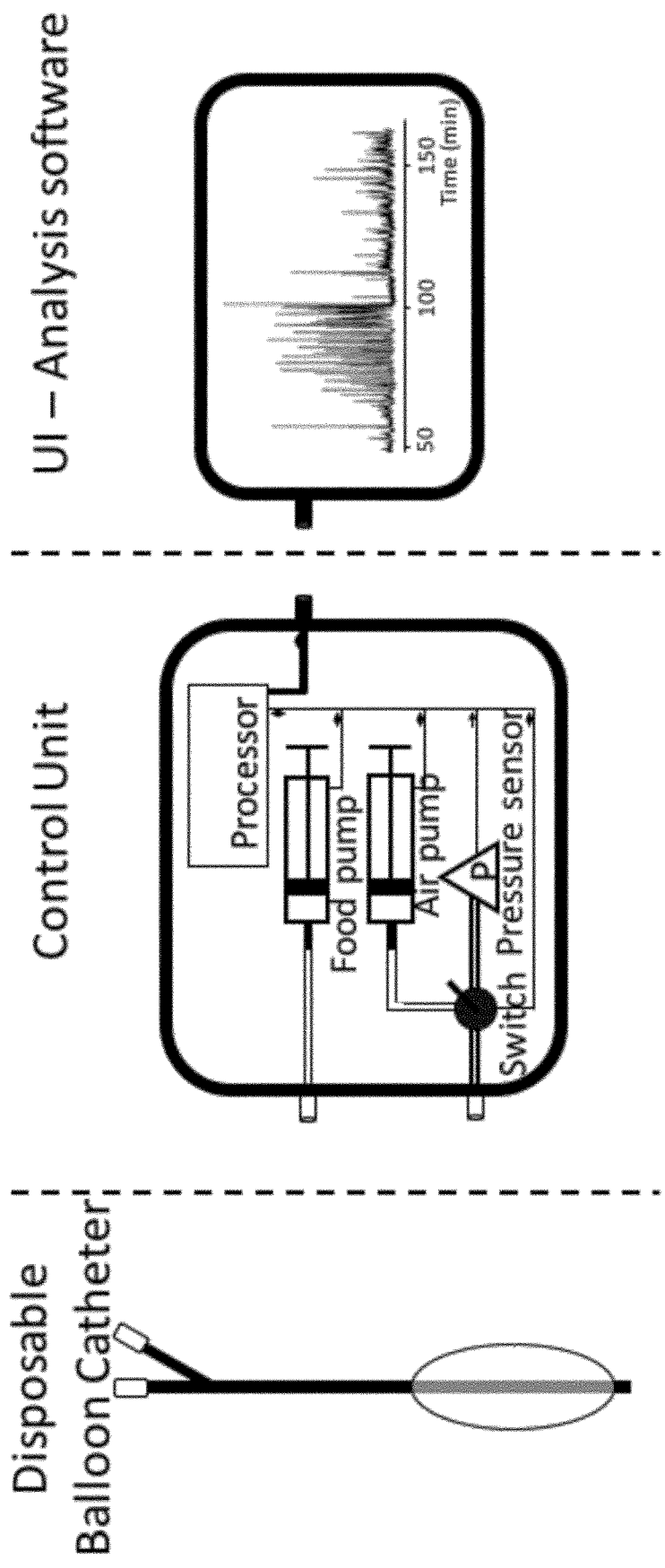

In some embodiments, the inflated balloon of said balloon catheter has a maximum diameter of between 4.0 cm and 7.0 cm, preferably between 4.1 cm and 6.5 cm, more preferably between 4.2 cm and 6.2 cm, even more preferably between 4.3 cm and 5.7 cm, most preferably between 4.3 cm and 5.5 cm, for example about 4.5 cm. In certain embodiments, the balloon has a length 12 (according to the numbering in FIG. 1) of about 7 cm to about 18 cm. The balloon may have a length of about 9 cm to about 16 cm, or a length of about 9 cm, about 10 cm, about 11 cm, about 12 cm, about 13 cm, about 14 cm, about 15 cm or about 16 cm, typically a length of about 14 cm.

In certain embodiments, the inflated balloon has a central cylindrical portion and the distal and proximal ends are closed off smoothly, for example in a substantial conical or semi-spherical or paraboloid manner, or using any other suitable shape.

In some embodiments, the inflated balloon with the required dimensions of length and diameter and volume is subdivided in multiple fluidly coupled segments. In some embodiments, the required dimensions of length and diameter are reached by using multiple balloons.

In certain embodiments, said catheter 2 extends through the distal end 6 of the balloon and said catheter contains a second lumen 7 that is fluidly coupled to the stomach via at least one opening 8 in the surface of the catheter. Preferably, said lumen 7 is coupled to the stomach via at least one, two, three, four, five or more openings 8 in the surface of the catheter.

Through these at least one openings 8 a fluid can be administered to or collected from the stomach. When the at least one opening 8 is situated distally from the distal end 5 of the inflated balloon, said at least one opening is located in a range between about 0.1 to about 5 cm from the distal end 5 of the inflated balloon, typically in a range between about 0.5 to about 3 cm from the distal end 5 of the inflated balloon, such as a range between about 0.5 to about 1.5 cm from the distal and 5 of the inflated balloon. When said at least one opening 8 is situated proximally to the proximal end 6 of the balloon, the opening is located in a range between about 0.1 to about 5 cm from the proximal end 6 of the inflated balloon, typically in a range between about 0.5 to about 3 cm from the proximal end 6 of the inflated balloon, such as a range between about 1 to about 1.5 cm from the proximal and 6 of the inflated balloon.

If a substance is to be introduced in the duodenum or small intestine rather than in the stomach, the opening(s) 8 are preferably located at a distance from about 10 cm to about 50 cm from the distal end 5 of the balloon, for example at about 15 cm, or about 20 cm, or at about 25 cm, or about 30 cm, or about 35 cm, or about 40 cm.

The inside diameter of the lumen 7 is in the range between about 1 to about 7 mm, generally in the range between about 2 and about 7 mm, typically in the range between about 2 to about 6 mm. A fluid coupling between the lumen 7 and the stomach refers to the fact that a fluid can be administered to or collected from the stomach by transferring said fluid through the lumen 7 of the catheter.

In specific embodiments the catheter can be used for administering and/or removing fluid e.g. liquid substance into/from the stomach, duodenum/small intestine via opening 8 in the catheter but located outside of the balloon. Should the lumen 8 with an opening situated distally from the distal ending of the balloon be used to infuse a fluid in the stomach it is of importance to have that opening as close to the distal end of the balloon as physically possible to avoid infusion of the nutrient to distally in the antrum of even the duodenum to avoid dumping syndrome.

In certain embodiments, the catheter 2 is positioned through the inside of said balloon 1 and wherein the distal end 5 and the proximal end 6 of said balloon are attached to said catheter.

The distal and proximal ends of the balloon 1 are attached and/or connected to the catheter 2 in a non-detachable manner. In other words, the balloon 1 and the catheter 2 are to be connected in a manner that upon positioning of said apparatus in the stomach, the balloon and catheter are not detached from each other. This non-detachable attachment can be performed using adhesive material including but not limited to drying adhesives, pressure-sensitive adhesives, contact adhesives and hot adhesives or such as reactive adhesives including but not limited to one-part adhesives or multi-part adhesives. In addition, non-detachable attachment and/or connection of the ends of the balloon to the catheter can be performed by different procedures such as melting the distal and proximal ends of the balloon to the catheter (thermal bonding).

The diameter 10 of said vertical section of said deflated balloon together with said catheter allows easy passage through a 7.7 mm (23 French) hole or opening, or a 6.3 mm (19 French) hole, or a 5.3 mm (16 French) hole. The maximum allowed diameter of the deflated balloon will be determined by the anatomy of the nose since the apparatus of the present invention needs to be inserted in the stomach of the mammalian subject via the nose.

The balloon is attached to the distal end 9 of said catheter wherein the diameter 10 of the combined deflated balloon together with said catheter allows easy passage through a 7.7 mm (23 French) hole, preferably through a 7.0 mm (21 French) hole, more preferably through a 6.3 mm (19 French) hole, even more preferably through a 5.3 mm (16 French) hole. The small diameter allows the application of the deflated balloon catheter via the nose. The above dimensions are typical for catheters for use in adults. Dimensions can be adapted to allow the use of the catheters in veterinary applications, or for infants/children.

Typically, a balloon of a balloon catheter according to the present invention has a "target volume" of about 90 ml to about 330 ml, a volume of about 100 ml to about 330 ml, a volume of about 150 ml to 300 ml, a volume of about 160 ml to about 290 ml, a volume of about 170 ml to about 250 ml, a volume of about 170 ml, 180 ml, 190 ml, 200 ml, 210 ml, 220 ml, 230 ml, 240 ml or 250 ml with some embodiments wherein the volume is about 180 ml.

In certain embodiments, lumen 3 is fluidly coupled to the inside of the balloon via at least one, two, three, four, five or more openings 4 in the catheter, allowing complete removal of fluid from the balloon after use.

Preferably, said lumen 7 is coupled to the stomach via at least one, two, three, four, five or more openings 8 in the surface of the catheter.

In certain embodiments, the balloon or balloons is/are made of semi-compliant or non-compliant material such as polyurethane (PU), thermoplastic polyurethane (PUR), thermoplastic elastomers as polyether block amides (PEBA), nylon, polyethylene (PE), polyethylene terephthalates (PET) or polyvinyl chlorides.

More preferably, said balloon is made of semi-compliant materials as PUR or polyether block amide, or none-compliant materials as PE or PET. Possible techniques to achieve the dimensions and shape of the balloon(s) are thermoforming and radio frequency welding of polyurethane, extrusion or casting, balloon blowing or by using injection or dip molding. Most preferably the balloons are made of aromatic thermoplastic polyurethane that is either polytetramethylene glycol-based or polycarbothane-based. TPU with a durometer in the range from 70 to 100 Shore A is preferred over a high durometer (e.g. 70 shore D or 70 Rockwell R).

Softer materials such as e.g. silicone, latex, chloroprene, and biocompatible elastic polymers are less suitable materials as these materials normally behave as compliant balloons and further inflation would not make the balloon sensitive to external pressure e.g. as exerted by the stomach upon the outer surface of the balloon.

The folding of the balloon and the openings of the lumen that connects to the inner space of the balloon is made in such a way that it enables to readily deflate the balloon without air trapped inside the balloon. Possibilities are multiple openings or openings along the circumference of the catheter.

In preferred embodiments, no electronic or optical devices or sensors are present in the balloon and/or in the catheter.

A specific embodiment of the above described catheter for measuring pressure or pressure changes, and/or for determination of gastric sensitivity to gastric distention, and/or optional stimulation of gastric motility and/or gastric emptying in the stomach comprises an inflatable balloon 1 wherein, in an inflated state, the vertical section of said balloon has a length of about 14 cm, has a diameter of about 4.5 cm and a volume of about 180 ml. The balloon is made of a semi-compliant or non-compliant material and only needs a low pressure to be inflated to its target volume, typically a pressure in the order of only about 0.1 psi (about 0.7 kPa) or only about 0.2 psi (about 1.4 kPa). When further inflated (e.g. for gastric stimulation), the intraballoon pressure increases steeply. Furthermore, the catheter 2 contains at least one lumen 3 fluidly coupled to the inside of the balloon via at least one opening in the surface of the catheter 4.

Another aspect of the present invention consists of a kit of parts comprising the balloon catheter as described in the first aspect of the present invention and an external pressure sensor for attachment to the proximal end of the small lumen 3 of said catheter. The baseline pressure in the stomach typically varies around 0.93 kPa (7 mmHg), depending on the weight of the person. Stomach contractions can generate pressures with peak pressures above 13.3 kPa (100 mmHg). Absolute pressure in the stomach is dependent on the atmospheric pressure and may need to be compensated for that. The balloon, tubing and sensor medium will be preferentially air. The temperature in the balloon is around 37° Celsius while the surrounding atmosphere typically has a temperature around 21° Celsius. Preferably sensors are used which are insensitive to temperature changes in the range from about 21° C. to about 37° C.

Pressure events in the stomach are relatively slow: based on our experience, data collection at a sampling rate of at least 5 Hz, e.g. at 10 Hz enables correct interpretation and analysis.

Further tests have shown that it may be beneficial to sample the balloon pressure at a sampling rate in the range from 1 Hz to about 10 Hz. This allows for example to also measure pressure changes related to breathing.

Other variables that may be taken into consideration for further processing of the raw measurement data are the input and output of the sensor device, and its sensitivity and accuracy.

Different types of pressure sensors may be used, such as for example piezoresistive, capacitive, optical, or any other suitable technology.

The balloon catheter of the present invention may be used to assess gastric motility, and/or to evaluate sensitivity to gastric distention and/or to stimulate gastric motility and gastric emptying.

Another aspect of the present invention relates to a system for measuring gastric motility, said system comprising a balloon catheter as described above and a control unit for recording and/or visualizing the pressure exerted upon the balloon when being inflated.

Important elements of the controlling unit are measuring the pressure in the balloon and processing this information to a display or computer for analysis. Optionally the control unit can contain a system (pump) to inflate and/or deflate the balloon. Optionally, the control unit further comprises a second pump adapted for pumping a liquid meal through the catheter directly in the stomach through a second lumen that has no connection with the inner balloon 7, but has an opening at a distal end of the catheter 2, outside of the balloon.

Once correctly positioned in the stomach, the balloon may be inflated with a predetermined volume (e.g. to its target volume, e.g. 200 ml or another value specific for the balloon in question), or with a predetermined pressure, or in any other suitable way.

If the balloon is not manually inflated but with an automatic or semi-automatic inflation system integrated in the controlling unit, this predefined volume may be delivered to the balloon at a certain speed or flow rate, and/or with a certain strength (contractions created by the stomach can be powerful (e.g. about 100 mmHg or 13.3 kPa) and the balloon will have a certain resistance to inflation). When an automated inflation and deflation system is integrated in the controlling unit, it is recommended to build in a safety/emergency deflation system for when the balloon is incorrectly positioned and the balloon is inflated while still in the oesophagus. Also, when the experiment is finished the balloon needs to be deflated manually, or the system has to deflate the balloon until all air is removed. It is advantageous to know how much air is deflated so that it is possible to detect leakage or incomplete deflation of the balloon.

The controlling unit optionally comprises at least one switch or valve, e.g. a three-way valve that allows the balloon catheter to be connected to either the pressure sensor or the pump. In other embodiments, such switch(es) or valve is omitted, and a simple T-connection may be used for interconnecting both the air pump and the pressure sensor to the first lumen of the balloon catheter. It is an advantage of disconnecting the air pump from the first lumen to reduce the amount of dead volume (thus increase the sensitivity). It is an advantage of disconnecting the pressure sensor from the air pump to reduce the risk of damaging the pressure sensor.

Internal tubing and connections in the control unit preferably does not deform in time or with temperature. Pressures and volumes are preferably not influenced in time by changed properties of the tubing. The system of the present invention can function without food pump. Control elements for integrating the control of a food pump are optional.

The input from the sensor, the switch, the air pump and the meal pump as well as the steering of the at least one switch or valve and the pumps can be processed by a processor that allows communication with a computer or a simple display. When connected to the computer information can be processed so that the computer can command the controlling unit, using dedicated communication protocols with the computer.

Another aspect of the present invention (as depicted in schematic 20) relates to a diagnostic non-therapeutic method for measuring pressure changes in the stomach, wherein said method comprises the steps of
a) inserting a balloon catheter as described above with the balloon in its deflated state into the stomach through the nose of said subject; and
b) inflating said balloon by inserting a pre-defined volume of fluid through lumen 3 and
c) measuring pressure changes inside the balloon using an external pressure sensor while keeping the volume of the balloon at a constant value.

Optionally, liquid can be administered into the stomach via opening 8 in the catheter at any moment after the apparatus has been inserted into the stomach of the subject through the nose.

Food intolerance with enteral feeding is an important issue particularly in critically ill patients. These patients often receive nasogastric tube feeding to maintain their nutritional intake in periods of critical illness. Gastric motility and emptying is often disturbed (50-80% of intensive care unit (ICU) patients). This leads to stasis of the nutrition in the stomach and food intolerance, failure to absorb essential nutrients and a risk of other complications such as aspiration pneumonia, regurgitation, emesis and vomiting. On the ICU delayed gastric emptying as a consequence of impaired motility is evaluated by clinical evaluation of the patient (e.g. bloated patient, regurgitation or diarrhoea) or by aspiration of the entire gastric residual volume (GRV) (7). No consensus exists on relevant GRV thresholds, neither for the guidelines on enteral nutrition protocols. Fearful management of nasogastric tube feeding, based on avoidance of high GRV, may deprive critically ill patients unnecessarily from their optimal nutritional intake.

Impaired motility of stomach and stomach emptying are important pathophysiological factors in different gastrointestinal diseases and disorders and food intolerance in general. In particular, the apparatus and methods of the present invention are applicable in the diagnosis and follow up of the following conditions. Furthermore, the apparatus and methods of the present invention may be used to stimulate gastric motility and emptying and thereby provide a therapeutic benefit in these conditions.

Gastroparesis (partial paralysis of the stomach muscles) is defined by severely delayed gastric emptying in the absence of an obstruction, resulting in postprandial fullness, early satiation, nausea and vomiting. Gastroparesis is estimated to affect up to 2% of the population and to account for major healthcare expenditure. A large group of gastroparesis patients is in fact a subset of functional dyspepsia (FD) patients with more severe symptoms in whom gastric emptying has been measured, and data from the U.S. show a shift over time to diagnosing gastroparesis at the expense of FD (8).

Functional dyspepsia (FD) is characterized by symptoms like early satiation, postprandial fullness and epigastric pain and burning. Due to the high prevalence (5 to 45% of the population) and the chronic nature of the symptoms, FD constitutes a major health-economic burden (9). The diagnosis of FD is based on the presence of chronic epigastric symptoms in the absence of an organic or metabolic cause that is likely to explain these symptoms, which is mostly confirmed by a negative upper gastrointestinal endoscopy. It is known from research that the underlying pathophysiological mechanism is multifactorial, including impaired gastric motility, delayed gastric emptying, visceral hypersensitivity, low-grade mucosal inflammation and impaired duodenal feedback mechanisms. However, in clinical practice the underlying pathophysiology is not diagnosed, since there is no conclusive test or biomarker that can discriminate between these disorders.

Several balloons are described in patent literature that comprise features that would allow pressure measurements in the stomach of a patient (pressure measurement systems). The present invention differs from the known devices inter alia as follows:
WO2012006625: The balloon of the present invention is larger in all dimensions. In fact, the balloon described in WO2012006625 (with a maximum length of 8 cm and a diameter of 3 cm) would be too small to accurately measure gastric motility-induced pressure changes and is for the assessment of abdominal pressure instead.

WO200866943: Even though balloons are described in WO200866943 that range with an inflated diameter between 2 and 5 cm and an inflated length of between about 10 and 30 cm, the deflated diameter of balloon catheter assembly described in WO2008066943 seems not to allow comfortable passage through the nose (<7.7 mm (23 French)). The unique combination of properties of the balloon described in the present invention (low pressure (between 0-1 psi), fairly large and specific diameter (between 4 and 7 cm) and length (between 7 and 18 cm) gives it unique features that allow accurate measurement of gastric motility without inducing epigastric symptoms as opposed to the wide range of balloon possibilities described in WO200866943 that includes balloons that are too small to accurately assess motility or are too large so they would induce epigastric symptoms.

US200816707 discloses an enteral feeding catheter for delivering nutrient into a patient's stomach, which may be advanced with its distal tip ahead through the nose or mouth of a patient into the oesophagus and stomach of the patient. The catheter has several lumen that can also be used to inflate several balloons attached to the catheter. The balloons are for anchoring the balloon catheter and for the determination of abdominal pressure. The balloons described in US2008167607 are smaller as compared to balloon described in the claims of the present invention. In fact, in order to measure the abdominal pressure the balloons cannot be influenced by gastric motility and therefore need to be small enough.

Also outside patent literature several examples can be found with features that might allow the measurement of intragastric pressure. The present invention differs from the known literature inter alia as follows:

The so-called Blakemore/Sengstaken tubes comprise a first balloon for application in the oesophagus and a second balloon for application in the stomach. The major difference vs. the balloon described in the current patent is that the length of the intragastric balloon is shorter than 7 cm and the balloon material is elastic in nature (e.g. latex). In addition, pressures needed to inflate the balloon are relatively high (>1 psi).

The Goremedical Q50 Stent Graft balloon catheter is used for temporary occlusion of a large vessel. The major difference vs. the balloon described in the current patent is that the pressure needed to inflate the Q50 balloon to a diameter more than 4 cm is well-above 1 psi.

Foley (Rusch) catheters are placed through the urethra into the bladder. Also here the pressure needed to inflate these balloon to a diameter more than 4 cm is well-above 1 psi. These balloons are spherical and made of elastic or compliant material such as latex or silicone.

The Mcompass balloon catheter is used for anorectal manometry measurements. This catheter is too short to place through the nose into the stomach. To place a catheter with a balloon of minimally 7 cm length at the distal end through the nose with the balloon into the stomach and the proximal end outside the nose a minimal catheter length of 80 cm is required with adults. To inflate the Mcompass balloon to more than 90 ml a pressure above 1 psi is needed.

The Bakri Balloon Tamponade catheter is used to control and diminish uterus bleeding after delivery. The balloons on the Bakri Balloon Tamponade are made of elastic or compliant material such as latex or silicone.

Contrary to catheters wherein optical detection is performed, the balloons of the present invention which are used for pressure measurement do not have be translucent, transparent or optically clear (or contain such portions), although they may.

For the purpose of the device and system of the present invention, the catheter only requires the positioning of a single balloon in the stomach. Additional balloons for positioning a balloon in the oesophagus are not required and can be omitted in the design of a balloon catheter.

None of the balloon catheters described in literature are optimised for the measurement of gastric motility-induced pressure changes or can be comfortably positioned through the nose (maximum deflated diameter of balloon+catheter less than 23 French.). The present invention allows to measure gastric motility via a balloon catheter that can be positioned through the nose because of a unique combination of properties:

Length of the inflated balloon to allow accurate measurement of stomach motility-induced pressure changes without inducing epigastric symptoms. (instead of specifying a length, one can also specify the volume of the balloon).

Diameter of the inflated balloon such that inflated accurate measurement of stomach motility-induced pressure changes is possible without inducing epigastric symptoms, but when deflated (but still mounted on the catheter) can pass through a 7.7 mm (23 French) hole.

Pressure to inflate the balloon to its "target volume" is relatively low, preferably in the range from about 20 to 30 cm $H_2O$, which is about 0.3 to 0.4 psi).

The balloon is made of a relatively hard material (for allowing accurate measurements), but not too hard (for easy passage through the nose).

EXAMPLES

Examples 1

In the present example, optimal dimensions of the balloon (shape, size and volume) for gastric motility measurement were determined by measuring the pressure in an intragastric balloon filled with a pre-determined volume of air. Therefore, balloon pressure readout was compared vs. a reference method (High Resolution Manometry). Furthermore, the potential for stimulating gastric motility was investigated as well as the symptoms provoked by balloon distension.

Eight healthy volunteers were recruited for this study. After a first successful experiment, the subjects were asked to return several times with at least one week in between each visit, up to 10 visits per subject. Subjects were asked to the clinic after at least 6 hours fasting, none of the subjects were taking any medication apart from contraception pills. The subjects were asked to refrain from alcohol, thee and coffee at least 12 hours before participation, moreover were they asked to refrain from smoking cigarettes at least 1 hour before the start of the experiment.

Healthy volunteers were recruited from an existing mailing list with subjects that have already participated in clinical studies. All subjects signed the informed consent form.

Inclusion criteria were:
Between 18-60 years old (adults).
Must provide witnessed written informed consent prior to any study procedures being performed.
Exclusion criteria were:
Taking medication or drugs
Severely decreased kidney and/or liver function.
Severe heart disease, for example a history of irregular heartbeats, angina or heart attack.
Severe lung disease.
Severe psychiatric illness or neurological illness.
Gastrointestinal disease.
Dyspeptic symptoms.
Women that are pregnant or breastfeeding.

In every experiment gastric motility was assessed with 2 techniques: a well-validated high resolution manometry technique and a flaccid bag connected to a single lumen tube connected to an external pressure transducer. Both catheters were positioned in the stomach as depicted in schematic 2.

A High-Resolution Manometer [HRM; 36 pressure channels; Sandhill (Milwaukee, USA), UNI-ESO-ZK40A, Unisensor, Attikon, CH] was positioned through the nose in the stomach so that the pressure channels span the entire stomach from the lower esophageal sphincter to the duodenal sphincter. The balloon catheter was positioned through the mouth in the stomach using a water-based lubricant gel to ease the intubation. Depending on the subject preferences local anesthetic (xylocaine spray) was used. After positioning the catheters, the subjects were asked to take place in a bed in a comfortable sitting position with the trunk upright.

After positioning the balloon catheter, the balloon was initially filled with a small volume of air: 10 ml (for a 25 ml balloon), 20 ml (for a 50 ml balloon) or 50 ml (for 90-350 ml balloons) for 10 minutes. Thereafter the catheter was retracted to ensure the balloon was positioned with its proximal part close to the lower esophageal sphincter. Hereafter the balloon was inflated its test volume (90% of the balloon maximum volume). No interventions were performed until at least 1 phase I and III were witnessed (by visual inspection) or for maximally 2 hours. Hereafter 200 ml of a nutrient drink [Fortimel Nutridrink; Nutricia (The Netherlands)] or water was infused directly into the stomach through the catheter at a constant speed of 30 ml/min. 30 minutes after the start of the nutrient drink infusion the balloon was deflated to its initial volume (10-50 ml) for 10 minutes. Hereafter the catheters were disconnected and removed and the volunteers could leave the hospital. Throughout the experiment discomfort, nausea, pain, bloating and hunger were scored on a visual analogue scale of 100 mm.

Custom-made balloon catheters were used to compare different balloon sizes. Balloons were made separately and pasted on a catheter using glue (Cyanoacrylate). Different catheters assemblies were used with similar characteristics. The subjects in the study never mentioned any difference when different catheters were used. In all constructions the length of the catheter was more than 100 cm so that the distal tip of the catheter can be positioned in the stomach while the catheter runs through the esophagus, the oral cavity and can be connected comfortably outside the body. The proximal endings were modified to allow airtight connection to a 3-way luer stopcock. 2 type of catheters were used: sump and Levine catheters:

SUMP CATHETER ASSEMBLY: e.g. polyvinyl chloride (PVC) or polyurethane (PU) dual flow (Sump) CH8-10 catheters (Vygon; Ecouen (France)). The catheters were manually modified to block the distal end opening of the small diameter lumen and to add an opening of the small diameter lumen at the location of the balloon (see schematic 3). The modified Sump catheter has 2 lumina:
1) Small lumen that was used for balloon in- and deflation and pressure measurement. 2) Large diameter lumen that was used for infusion of liquid nutrient, drugs or other substances. This lumen was also used for the guide-wire.

LEVIN CATHETER ASSEMBLY: an 8-10 Fr single lumen polyurethane nasogastric feeding tube was used (Entral RT8/80; Maxter catheters (UK) or Nutricia Flocare; Nutricia Advanced Medical Solutions). A second thin single lumen rigid polyethylene (PE) tube (inner diameter 0.86 mm; Intramedic; Becton Dickinson) was used to in- or deflate the balloon and to measure intraballoon pressure. The thin PE tube was inserted in the proximal balloon end while attaching the balloon to the catheter (schematic 4).

Balloon characteristics

Inflated balloon size: see schematic 5. Balloons with different radius (2, 2.5, 3, 3.5, 4 and 4.5 cm) and different lengths (sphere, 11 and 18 cm) were tested. The balloon volumes varied from 25 ml (2 cm radius sphere form) up to 350 ml (2.5 cm radius elongated to 18 cm).

In this set of experiments, 10 different balloons were tested:
1) Circumference of 13 cm, sphere form (diameter of 4 cm); approximate volume 25 ml.
2) Circumference of 13 cm, cylinder form, length of the cylinder: 11 cm; appr. volume 135 ml
3) Circumference of 16 cm, sphere form (diameter of 5 cm); appr. volume 55 ml
4) Circumference of 16 cm, cylinder form, length of the cylinder: 11 cm; appr. volume 210 ml
5) Circumference of 16 cm, cylinder form, length of the cylinder: 18 cm; appr. volume 350 ml
6) Circumference of 19 cm, sphere form (diameter of 6 cm); appr. volume 90 ml
7) Circumference of 19 cm, cylinder form, length of the cylinder: 11 cm; appr. volume 240 ml
8) Circumference of 22 cm, sphere form (diameter of 7 cm); appr. volume 170 ml
9) Circumference of 25 cm, sphere form (diameter of 8 cm); appr. volume 215 m
10) Circumference of 28 cm, sphere form (diameter of 9 cm); appr. volume 330 ml Material and construction: balloons were custom-made using polyethylene foil (PE; non-elastic). The PE balloons were assembled out of 4 separate pieces (see schematic 6) using a vacuum bag sealer (Vacupack Plus F380; Krups, Solingen, Germany). Once sealed, at both lateral sides of the balloon a hole was pierced so that the catheter could be slid through the balloon. Once the catheter was slid through the balloon the balloon was glued to the catheter using cyanoacrylate glue, furthermore was a silk threat bound around the endings of the balloon around the catheter to ensure the air-tight sealing. The balloon catheter was always checked to be air-tight by inflating the balloon to its maximal volume while measuring the pressure (pressure should be stable for more than 1 hour).

The small lumen of the catheter was connected to a 3-way Luer stopcock that connected via custom-made air-tight tubing to a differential pressure sensor [MPX2010DP Freescale Semiconductor, NXP (Eindhoven, The Netherlands)] to record the balloon pressure via a custom-made data acquisition system and recording system [PharmLab 5.0, AstraZeneca (R&D Mölndal, Sweden)]. The 3-way stopcock also allowed to manually inflate and deflate the balloon with air using a syringe.

Balloon pressure data. Customized computer software [Pharmlab 5.0, AstraZeneca R&D (Mölndal, Sweden)] was used to record pressure as mmHg at 1 Hz. Data was imported at 1 Hz for analysis into Microsoft Excel 2013 [Microsoft (Redmont, USA)]. A moving median over 30 seconds was calculated from the original data (to discard short-term extreme outliers such as deep breathing and movement artefacts). From this moving median a moving minimum was calculated over 5 minutes, which was averaged out over 5 minutes (=baseline). A moving average over 30 seconds was calculated from the original data. A delta value was calculated as the difference between the moving average (30 seconds) and the moving minimum baseline. The maximum delta value was calculated. Per second a delta value exceeded 30% of the maximum delta value it was flagged as contraction (see schematic 7).

HRM pressure data. Customized Sandhill Analysis Recording software [Sandhill Scientific (Denver, USA)] was used to record pressure in mmHg. Data was imported into Microsoft Excel (Redmont, USA) at 1 Hz and divided into 3 data sets:

1) Average pressure in the proximal stomach: average pressure of the pressure channels located in the proximal half of the stomach, from the lower esophageal sphincter downwards (channels in the sphincter not included).

2) Average pressure in the distal stomach: average pressure of the pressure channels located in the distal half of the stomach, until the pyloric sphincter (channels in the sphincter not included).

3) Overall stomach pressure: average of the proximal and distal pressure channels. Similar to the balloon pressure a moving minimum was calculated over 5 minutes from a moving median over 30 seconds. A moving average (over 5 minutes) from this moving minimum was defined as the baseline. A moving average over 60 seconds was calculated from the 3 data sets (proximal stomach, distal stomach and overall stomach pressure). Per second the delta value exceeded 30% of the maximum delta value it was flagged as contraction (see schematic 7).

To investigate how well the balloon could detect contractions in the distal stomach the time during which a contraction was seen in the distal half of the HRM pressure channels located in the stomach while at the same time no corresponding contraction was detected from the balloon pressure data was summed and divided by the total time during which a contraction was detected in the HRM distal channels. This percentage is an indication of the contractions measured by the HRM in the distal stomach that were not picked up by the balloon. This analysis was performed in the time period during which the balloon was fully-inflated and before the start of the nutrient drink infusion.

In the 2-hour measurement after balloon inflation and before nutrient drink infusion the occurrence of a phase III contraction pattern followed by a phase I was manually and visually detected (score 0=no phase III occurred, score 1=phase III occurred followed by a phase I).

At several time-points epigastric sensations (bloating, pain, discomfort, nausea and hunger) were scored using a 100 mm Visual Analogue Score. Scores were collected before balloon inflation, directly after inflation, before nutrient drink infusion, directly after nutrient drink infusion and before balloon deflation.

Satiation was scored on a graded scale 0-5 whereby 0 represents 'no satiation feeling' and 5 represents 'the most satiated I have ever felt'. Satiation was scored every minute from the start of the nutrient drink infusion until the balloon was removed (40 minutes after the start of the nutrient drink infusion).

Results are represented as mean±STDEV. Comparisons were made in paired-wise fashion using a Students t-test (2 comparisons) or ANOVA (multiple comparisons). $P<0.05$ was considered significant.

The HRM pressure catheter is regarded as the golden standard to assess contractions in the distal stomach, and was used to evaluate to what extent the balloons can detect all contractions in the distal stomach. The time during which contractions are detected by the HRM in the distal stomach and no corresponding contraction could be detected by the balloon was summed and divided by the total HRM contraction time and represented as % in Schematic 8. In general, the balloon could detect more contractions in the distal stomach the larger the balloon was (wider and longer). Phase III contractions were defined as described in (10), could easily be observed from the HRM tracing, and were used to determine to what extent the balloons could stimulate phase III contractions. The occurrence of a phase III followed by phase I was compared between the different balloons used (see schematic 9). Phase III and I always occurred when balloons with a radius of 2.5 cm and a length of 11 or 18 cm were used, when balloons with a radius of 3 cm and length of 11 cm were used and when balloons with a radius of 4 cm were used.

In general, the more volume the balloon had, the more phase III contractions occurred (bottom figure schematic 9).

Sensitivity upon balloon inflation was compared by comparing the different epigastric sensation scores directly after balloon inflation. See schematic 10. Symptoms such as, bloating, discomfort, nausea and pain were scored with high-volume balloons: 2.5 cm radius with a length of 18 cm length and the 4.5 cm radius balloons.

See schematic 11: satiation scores are represented for the different balloons tested at 3 time points: directly after the nutrient drink was infused, 30 minutes after the start of the nutrient drink infusion (directly before the balloon was deflated) and 40 minutes after the start of the nutrient drink infusion (deflated balloon). It appears the longest balloons induced the longest lasting satiation.

The following trends emerged from these experiments:
With increasing balloon volume contractions are better detected.
With increasing balloon volume phase III contractions are better stimulated
Epigastric sensations are consistently induced with high-volume balloons (>300 ml) and balloon with a diameter of 6 cm and above
Satiation after nutrient drink infusion remains highest with the longest balloon (18 cm long)

In this study, the balloon was positioned with its proximal end close to the lower esophageal sphincter. From this study, it can be concluded that the best balloon to accurately measure gastric motility is the balloon with a diameter of about 4.5 to 5.5 cm diameter and a length of about 11 cm. With such a balloon, also motility is consistently stimulated while this balloon does not provoke epigastric symptoms.

Examples 2

The example investigates balloon material properties for optimal sensitivity to external pressure.

To understand the optimal material properties of the balloon necessary to obtain optimal sensitivity to external pressure 3 balloons with similar inflated dimensions but different elastic properties were compared. The following balloons were tested:

Non-compliant polyethylene (PE) balloon (also used in examples 1)

Compliant latex balloon that generates low pressures upon inflation [Durex Invisible Condom (Reckitt Benckiser, Brussels, Belgium)]

Compliant latex balloon that generated high pressures upon inflation [Sempertex 260 Modelling balloon (Sempertex Europe, Genk, Belgium)]

All balloons were made so that when bound to the catheter as in schematic 3 and inflated to 200 ml, the balloons had a cylindrical shape with a length of 11 cm and a diameter of 5 cm.

Balloons were stepwise inflated "on the bench" with steps of 50 ml to 250 ml while measuring the intraballoon pressure (see schematic 12A). During stepwise inflation, the pressure in the non-compliant PE balloon increased exponential: the pressure was very low until approximately 200 ml after which the pressure increased rapidly. During stepwise infusion of the compliant latex balloons the pressure increased rapidly at first while pressure increase was less pronounced after initial inflation. In the compliant Durex balloon the pressure increase plateaued after 150 ml was inflated.

A custom-made setup was used to measure sensitivity of the balloon to externally-applied pressure (see schematic 13). Once inflated to 200 ml the balloon was connected to a pressure sensor and positioned in the setup. The setup was built so that the balloon was loosely constricted for movement. On one end of the balloon a construction allowed to apply external pressure on the balloon (adjustable water-load). The other end of the balloon was left untouched. Schematic 12B shows the effect of increasing the water load with steps of 10 ml to a total of 50 ml. Thereafter the load was increased with steps of 50 ml to a total of 400 ml. With increasing external pressure, the pressure in the non-compliant PE balloon increased linearly (black lines and filled symbols). On the other hand, the pressure increase in the compliant latex balloons were much less pronounced and had a non-linear relationship.

It was concluded from this set of experiments that external pressure applied on a limited area of an inflated balloon does not always increase the intra-balloon pressure in the same manner. External pressure applied on a limited area of a compliant balloon displaces the volume in that balloon rather than increasing the intraballoon pressure. A sensitive balloon is therefore preferentially non-compliant or semi-compliant since external pressure applied on a non-compliant balloon will result in pressure increase rather than volume displacement.

On the other hand, the intraballoon pressure itself may also play a role: the compliant latex balloon with a high intraballoon pressure when inflated to 200 ml was less sensitive to low-weight external pressure: the intraballoon pressure only increased with a load of 100 ml or more despite that this balloon was less compliant as compared to the durex balloon.

In summary, a balloon that is sensitive to external pressure is typically a non-compliant or semi-compliant balloon that, when inflated to its full volume, has a low pressure to be inflated to the target volume, but intraballoon pressure increases (rapidly) when further inflated.

Example 3

The example explored the potential of a balloon with the optimal balloon size as determined in examples 1 and the optimal balloon material characteristics as determined in examples 2. More specifically the aim was 3-fold:

To investigate whether the nasogastric balloon catheter can be used to detect (codeine-induced) decreased gastric motility.

To investigate the correlation between gastric motility and gastric emptying changes after codeine treatment.

To investigate whether the presence of an inflated intra-gastric balloon influences gastric motility and emptying.

6 healthy subjects were recruited for this study. After a first successful experiment, the subjects were asked to return 3 times (hence 4 experiments in total). Subjects were asked to come to the clinic after at least 6 hours fasting, none of the subjects were taking any medication apart from contraception pills. The subjects were asked to refrain from alcohol, thee and coffee at least 12 hours before participation, moreover were they asked to refrain from smoking cigarettes at least 1 hour before the start of the experiment.

Healthy subjects were recruited from an existing mailing list with subjects that have already participated in clinical studies. All subjects signed the informed consent form.

Inclusion criteria were:

Between 18-60 years old.

They can go home without driving a vehicle

They will not operate machines on the same day of treatment

Exclusion criteria were:

Taking medication.

Have severely decreased kidney function.

Have severely decreased liver function.

Have severe heart disease, for example a history of irregular heartbeats, angina or heart attack.

Have severe lung disease, asthma, chronic bronchorroe (bronchiectasis, cystic fibrosis).

Have severe psychiatric illness or neurological illness.

Have any gastrointestinal disease.

Have any dyspeptic symptoms.

Women that are pregnant or breastfeeding.

Taking drugs

Having known side-effects/allergic reactions when taking codeine/morphine

The study was designed as a randomized crossover study with 4 groups was (see schematic 14):

20 ml balloon—placebo 20 ml balloon—codeine 200 ml balloon—placebo 200 ml balloon—codeine The 20 ml balloon experiments served as a control for the 200 ml balloon experiments since the effect of a 200 ml balloon on gastric motility and emptying is unknown. Gastric motility was assessed with a double lumen balloon catheter as described below by measuring the pressure in the balloon with an external pressure sensor. A water-based lubricant jelly was used to ease the intubation. Depending on the subject preferences a local anaesthetic (xylocaine spray) was used. The catheter was not fixed to the subject's chin. The volunteers were asked to take place in a bed in a comfortable sitting position with the trunk upright.

The volunteers received either placebo or codeine as a syrup. After positioning the balloon catheter the balloon was filled with 50 ml for 10 minutes, hereafter the balloon was inflated to 200 ml of deflated to 20 ml depending on the treatment arm. After this and in total 20 minutes after syrup ingestion 150 ml of a nutrient drink (Nutridrink, Nutricia (NL)) was directly infused into the stomach at a constant speed of 75 ml/hour. Hereafter infusion stopped but measurement continued for approximately 4 hours until the experiment lasted approximately 6 hours. Hereafter the catheters were disconnected and removed and the volunteers could leave the hospital.

Gastric emptying rate was measured using the $^{13}$C-octanoic acid breath test (11). $^{13}$C-labeled octanoic acid was solved in the nutrient drink (0.5 mg/ml). Emptying of the stomach was assessed by analysis of the exhaled $^{13}CO_2$, after oxidation of octanoic acid in the liver. The breath test is routinely used in daily clinic to assess gastric emptying with no burden to healthy subjects or patients (12). Since nutrient infusion took place over 2 hours the total $^{13}$C-octanoic acid dose was 75 mg. Breath samples were collected twice before infusion start and every 15 minutes up to 320 minutes after start of the infusion. A Visual Analogue Scale (VAS) scoring on satiation, hunger, discomfort, nausea and pain was collected simultaneous with breath sampling.

In this study, the effect of codeine was studied vs. placebo. In view of the doses and the effects of codeine described in literature (13-16) a single dose of 60 mg per volunteer was chosen to decrease gastrointestinal motility. In view of the PK profile found in literature the effect of codeine is expected immediately after administration (13-16).

In de consulted literature no reference was made of side effects apart from those gastrointestinal-related (such as nausea). Codeine was administered as a syrup: BRONCHODINE® 9.8 mg codeine/5 ml syrup [Laboratoria Sterop NV, Brussels (BE)]. Normal dosing to reduce coughing is 15-30 mg 3 times per day. As placebo the same volume (30 ml) of a homeopathic syrup for the same indication was administrated [Drosetux (Boiron, Evere, Belgium)].

The balloon catheter assembly was performed as explained in example 1 schematic 3 and 4.

The characteristics of the balloon were as follows: the inflated balloon had a cylinder shape with a diameter of 5 cm (circumference of 16 cm) and a length 11 cm; appr. volume 210 ml. Balloons were custom made using Polyethylene foil (PE; non-elastic). The PE bags were assembled out of 4 separate pieces using a vacuum bag sealer (Vacupack Plus F380; Krups, Solingen, Germany). Once sealed, at both lateral sides of the balloon a hole was pierced so that the catheter could be slid through the balloon. Once the catheter was slid through the balloon the balloon was glued to the catheter and checked that it was air-tight.

The small lumen of the balloon catheter was connected to a 3-way Luer stopcock that connected via custom-made air-tight tubing to a differential pressure sensor [MPX2010DP (Freescale Semiconductor—NXP; Eindhoven, The Netherlands)] to record the balloon pressure via a custom-made data acquisition system and recording system (PharmLab 5.0, AstraZeneca R&D, Sweden). The 3-way stopcock also allowed to manually inflate and deflate the balloon with air using a syringe.

The following data were measured:

1) Gastric Motility (Balloon Pressure Data).

Customized computer software (Pharmlab 5.0; AstraZeneca R&D, Mölndal, Sweden) was used to record pressure as mmHg at 1 Hz. Data was imported at 1 Hz for analysis into Microsoft Excel 2013 (Microsoft, Redmont, USA). The baseline was calculated as follows:

A) From the original data a moving median over 30 seconds was calculated (to discard short-term extreme outliers such as deep breathing and movement artefacts).

B) From this moving median (A) a moving minimum was calculated over 10 minutes.

C) The baseline was calculated as the moving average from the moving minimum (B).

To quantify gastric motility a moving average over 30 seconds was calculated (to even out breathing). Gastric motility was quantified as the difference between this moving average and the baseline (=delta value; see schematic 15). Since data was recorded at 1 Hz, there is a delta value for each second. Gastric motility was quantified for different regions:

MI35: sum delta values in the 10-60 minutes time interval divided by 3000

MI90: sum delta values in the 60-120 minutes time interval divided by 3600

MI150: sum delta values in the 120-180 minutes time interval divided by 3600

MI210: sum delta values in the 180-240 minutes time interval divided by 3600

MI270: sum delta values in the 240-300 minutes time interval divided by 3600

2) Gastric emptying (breath test). The ratio of $^{13}CO_2$ to $^{12}CO_2$ (molar mass 45 and 44 gr/mol) in the breath samples collected was measured by isotope ratio mass spectrometry (IRMS; ABCA, Sercon, Crewe, UK). As described before (12) a $^{13}$C recovery rate per hour (% dosage per hour) was calculated per sample taking into account that the total dosage $^{13}$C was administered over 2 hours. The recovery rate per hour was plotted in time resulting in a skewed bell-shaped curve: see schematic 16a black filled circles. To estimate the half-emptying time a cumulative recovery rate curve was made (see schematic 16b). To estimate the gastric half emptying time the cumulative recovery rate must be fitted (since the maximum value is not reached by the experimental data). In most experiments fitting the cumulative values to a curve brought an uncertain maximum value and therefore an uncertain gastric half emptying time (GET½).

It was assumed that the recovery rate followed an exponential decay once the maximum recovery rate was reached. Therefore, the measured recovery rates from the point where the recovery rate only decreased was fitted to an exponential decay curve:

$Y=(Y0-\text{Plateau})*\exp(-K*X)+\text{Plateau}$     (see black line in schematic 16a)

With the estimated parameters from this fit recovery rates were simulated from the last measured point, every 15 minutes to t=480 minutes (empty symbols).

From the cumulative recovery rate data (including the simulated data) a hyperbolic curve was fitted according to the following equation:

$Y=\text{Bottom}+(X\text{-slope})*(\text{Top}-\text{Bottom})/(X\text{-slope}+\text{GET}½\hat{}\text{slope})$     (black line in schematic 16b)

GET½ was the result of this last fitting.

Results were represented as mean±STDEV. Comparisons were made in paired-wise fashion using a Students t-test (2 comparisons) or ANOVA (multiple comparisons) using Prism 7 for Windows (Graphpad software; La Jolla, USA). P<0.05 was considered significant.

Balloon pressure motility indexes (MI) were calculated for different time intervals according to the data analysis described above. Data were represented grouped per condition (inflated vs. deflated and placebo vs. codeine) in schematic 17. The following group comparisons were performed (without correction for multiple comparisons)

Placebo vs. codeine within the inflated group (200 ml balloons): significant treatment effect (P<0.01) and a significant time effect (P<0.001).

Placebo vs. codeine within the deflated group (20 ml balloons): no effect of treatment and a significant time effect (P<0.001)

Inflated vs. deflated within the placebo group: significant effect of condition (P<0.05) and a significant effect of time (P<0.001).

Inflated vs. deflated within the codeine group: no significant effect of condition or time.

Per condition a gastric half emptying time (GET½) was calculated and represented in schematic 18. The following group comparisons were performed (without correction for multiple comparisons)

Placebo vs. codeine within the inflated group: significant treatment effect (P<0.05).

Placebo vs. codeine within the deflated group: no significant treatment.

Inflated vs. deflated within the placebo group: significant condition effect (P<0.01).

Inflated vs. deflated within the codeine group: no significant condition effect.

Within the inflated (200 ml) condition the % decrease in MI (placebo vs. codeine) was correlated vs. the % increase in GET½ (placebo vs. codeine; see schematic 19). In all subjects codeine decreased MI and increased GET½. However, no significant correlation could be found between the two (Pearson r).

With the balloon inflated to 200 ml codeine significantly decreased gastric motility and delayed gastric emptying indicating that it is possible to detect decreased motility with a 200 ml balloon. No effect of codeine on motility could be detected with the balloon inflated to only 20 ml. As mentioned before the balloon can be too small for motility measurement, hence no valid comparisons can be made for motility with the deflated (20 ml) balloons.

Inflation of the balloon accelerated gastric emptying in the placebo condition. Codeine delayed gastric emptying when the balloon was inflated to 200 ml. No effect of codeine could be seen on gastric emptying when the balloon is deflated.

FIG. 21 is a schematic representation of several material hardness scales relevant for the present invention. Such scales are known per se in the art, and are provided herein only as an easy reference for the reader. It is noted that slight variations of these scales may be found in literature, but the main point of showing them here is that the scales overlap. Currently the most-preferred embodiments are those based on polyurethanes having a durometer of 70 to 100 shore A, as indicated by the dotted rectangle.

FIG. 22 and FIG. 23 show pictures of a balloon catheter 100 according to an embodiment of the present invention. The balloon catheter shown has a first lumen in fluid connection with a cavity inside the balloon for selectively inflating and deflating the balloon, and has a second lumen for supplying a substance to the stomach, or for collecting a substance from the stomach.

In FIG. 22 the balloon 1 is deflated and flattened. In order to be insertable through the nose, the balloon may be manually pressed inwardly towards the catheter.

In FIG. 23 the balloon is inflated to an external diameter of about 4.5 cm.

In a variant of the balloon catheter (not shown), the balloon catheter further comprises a third lumen, such that the second channel can be used only for supplying substance, and the third channel can be used only for collecting substance.

Figure 24:
FIG. 24 and FIG. 25 are an enlarged view of a balloon similar to those shown in FIG. 22 and FIG. 23.
Figure 25:
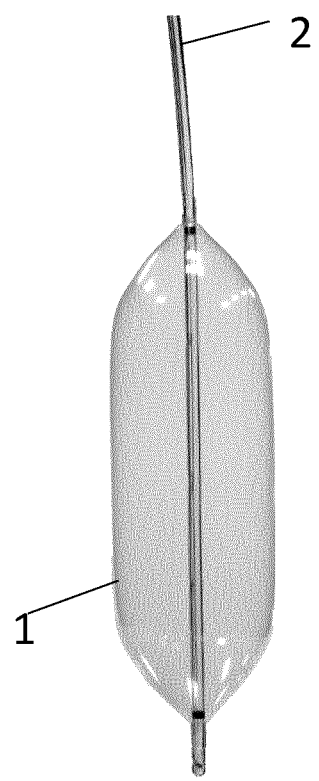

FIG. 24 and FIG. 25 are an enlarged view of a balloon similar to those shown in FIG. 22 and FIG. 23, having a target volume of about 200 ml, and made of a polyurethane commercially available from the company Lubrizol, under the name Pellethane®2363-90AE, having a durometer of 90 shore A.

As can be appreciated from FIG. 24, even a material with such a relatively high hardness can be flattened and crumpled to a very small diameter.

FIG. 25 shows the balloon of FIG. 24 after being inflated to its target volume having a smooth shape. The surface is tensioned but not or only marginally stretched.

FIG. 26 shows a volume versus pressure profile for an exemplary balloon made of polyurethane with a durometer of 90 shore A.

The balloon is inflated and deflated 'on the bench', outside a stomach. Hence there is no counter-pressure exerted on the balloon surface during this test. The outside of the balloon is air at room temperature (about 20° C.) and atmospheric pressure (about 1013 mbar or 101300 Pa).

If the balloon is inflated with a pressure of 0.20 psi (1.379 kPa), e.g. "on the bench", in an environment at 20° C. and 1013 mbar, without counter-pressure exerted on the balloon surface, the volume is about 150 ml. This value is considered the target volume of this particular balloon.

As can be appreciated from FIG. 26, the balloon volume increases quite linearly with applied pressure, however, this is not the pressure that is measured during normal use.

Figure 27:
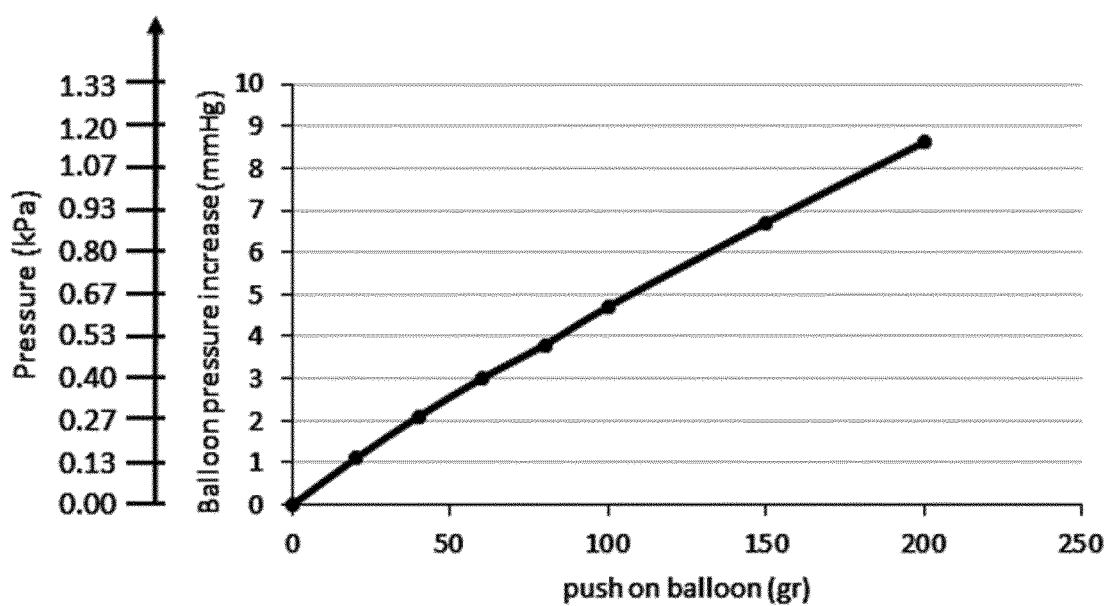
FIG. 27 shows the effect of externally-applied mechanical pressure on the fluid pressure inside the balloon having the characteristic of FIG. 26, measured 'on the bench'.

FIG. 27 shows the effect of externally-applied mechanical pressure on the fluid pressure inside the balloon having the characteristic of FIG. 26, again measured 'on the bench'. This curve is representative of what will happen when the balloon is inserted into the stomach of a person via the nose, and is inflated to its "target volume", in this case 150 ml, and when the stomach and/or other organs exert a pressure to the balloon wall. It can be understood that, when the organs press against the outer surface of the balloon, the fluid pressure inside the balloon will increase, this fluid pressure will be measured by a pressure sensor device.

The transfer function shows a surprisingly high sensitivity and linearity, thus allows for highly accurate measurements.

It is firmly believed that this behaviour is not obtained by existing balloons, which have one or more of the following characteristics: oversized, or made of a material that is too soft (e.g. less than 70 shore A) or which does not have suitable dimensions (volume, diameter, length) but instead displaces volume rather than being compressed, or need to be inflated with a higher pressure before reaching the same target volume. It is the combination of features that provides the advantageous effects of balloon catheters according to the present invention. In addition, when choosing a polyurethane having a durometer in the range from 70 to 100 shore A, the balloon catheter is far more suitable for being inserted via the nose.

As can be appreciated from the above description, several insights were required to overcome several conflicting requirements. The end-result is a balloon catheter having a unique and non-trivial combination of features, resulting in a balloon having a transfer characteristic like the one shown in FIG. 27, that allows very accurate measurements, and at the same time is insertable through the nose. It is an additional advantage that this balloon catheter can be used for feeding a person, and/or for stimulating gastric motility.

FIG. 28 shows a volume versus pressure profile for another exemplary balloon made of polyurethane with a durometer of 90 shore A, and having a target volume of about 190 ml (i.e. the volume assumed by the balloon when inflated with a pressure of 0.20 psi in an environment at 20° C. and 1013 mbar, without external pressure being applied to the balloon surface.

Figure 29:
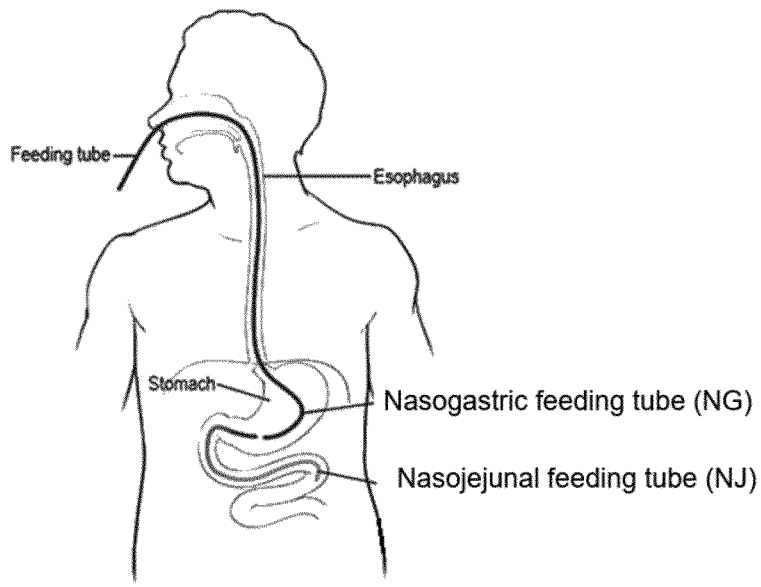
FIG. 29 shows an example of a nasogastric feeding tube, and a nasojejunal feeding tube, known in the art.

FIG. 29 shows an example of a nasogastric feeding tube, and a nasojejunal feeding tube, known in the art.
Administration/Collection to/from the Duodenum/Small Intestine:

Normally, enteral nutrition is delivered in the stomach or in case of intolerance (impaired stomach function) past the pylorus in the duodenum/small intestine. However, placing a feeding catheter through the pylorus is not easy, inter alia because the catheter typically curls in the proximal stomach, hence endoscopic assistance is typically required.

Experiments with the balloon catheter of the present invention revealed a surprising effect. It was unexpectedly observed that with a balloon catheter according to the present invention (when the balloon is inflated) the distal end 9 of the catheter is mostly automatically correctly positioned inside the stomach, so that the catheter, provided it is sufficiently long to enter the pylorus, does not require endoscopic aid. This is a major advantage, because endoscopic equipment is expensive and requires trained personnel to use and to apply, hence not requiring such equipment or training is a major advantage. This observation has led to further development of the balloon catheter to the embodiment shown in FIG. 30.

FIG. 30 shows a balloon catheter 3000, having a single balloon 1 and three lumen, referred to as first, second and "fourth" lumen for consistency of the description and claims, even if there are only three lumen: the "first lumen" 3 (with a relatively small diameter) for inflating the balloon 1 and for measuring pressure inside the balloon 1, the "second lumen" 2 with opening(s) 8 for providing a substance into the stomach, and the so called "fourth lumen" 2' with opening(s) 8' for providing a substance directly into the small intestine.

It is known in the art that nutrition can be delivered to the stomach or past the pylorus (duodenum or small intestine), using a nasogastric feeding tube (NG) and a nasojejunal feeding tube (NJ) respectively, as shown for example in FIG. 29. A typical nasogastric tube (without balloon) is about 85 cm long, a typical nasojejunal tube (without balloon) is about 125 cm long. For jejunal administration of nutrients past the pylorus the one or more opening 8 in the surface of the catheter through which fluid can be administered to or collected from the duodenum, is located typically 20 cm from the distal end 5 of the inflated balloon.

With a gastric balloon catheter according to the present invention, however, it is not only possible to provide nutrients, but also to measure gastric motility using the same catheter, moreover simultaneously. That is a major advantage.

Referring to FIG. 30, a triple or quadruple lumen catheter is shown, having at least two lumen for delivery of nutrition: the "second lumen" for providing substance into the stomach, and the "fourth lumen" for providing substance into the duodenum/small intestine. Administration of enteral nutrition into the second lumen will be guided towards the stomach 8 near the distal end of the balloon. The first lumen 3 can have a smaller diameter than the second and fourth lumen, because only air needs to pass through this lumen. This helps to reduce the outer diameter of the balloon catheter, which is important for being able to pass through the nose.

The at least one opening 8' in the fourth lumen can be located for example at a distance in the range from 10 to 50 cm from the distal end 5 of the balloon 1, for example at a distance of about 15 cm or about 20 cm or about 25 cm or about 30 cm or about 35 cm or about 40 cm.

While not shown in FIG. 30, (but see for example FIG. 32 to FIG. 35), in order to avoid connection-errors, preferably the lumen are provided with a different marking, e.g. with a different connector (e.g. different size and/or different colour). In this way, for example the risk of delivery of nutrition into the stomach while intended in the duodenum, can be avoided.

A system is also envisioned that, depending on the stomach function readout (GB-MI, which stands for "Gastric Balloon-Motility Index") delivers food to the stomach when possible (e.g. in case of a normal GB-MI) or into the duodenum when necessary (e.g. in case of a low GB-MI). Possible hardware-configurations of such systems are described in FIG. 32 to FIG. 35, but the algorithm to calculate the GB-MI falls outside of the scope of the present application. The interested reader is referred to the "co-pending system application". A balloon catheter as described in the present document is ideal for use in such as system.
Use of Multiple Balloons for the Assessment of Gastric Motility:

Productive or peristaltic gastric contractions have their origin in the proximal stomach (pacemaker area) and move distally over the antrum and pylorus towards the small intestine. This peristaltic movement of a contracted zone from the proximal to the distal stomach results in gastric emptying. Unproductive contractility on the contrary does not show this proximal to distal movement and is less or not effective promoting gastric emptying. The inventors of the present invention realized however that a balloon catheter with one balloon can measure whether or not there are contractions, but not whether these contractions are productive contractions or not.

Faced with this problem, they came to the idea of providing a balloon catheter 3100, 3330, 3430 with two (or more) balloons, for example as shown in FIG. 31 or FIG. 33 or FIG. 34. Such a balloon catheter allows to measure gastric contractions at two different locations, hence is effectively capable of detecting progression of a contractile zone from the proximal to the distal stomach.

FIG. 31 shows an example of such a balloon catheter, having two balloons (a first or proximal balloon 1, and a second or distal balloon 1'), and three lumen (referred to as first, second and third lumen for consistency of the description and claims): the first lumen 3 with an opening 4 inside the first balloon for inflating/deflating the first balloon 1 and for measuring pressure inside the first balloon 1, the second lumen 2 for providing a substance into the stomach (or the small intestine, depending on the location of the one or more openings 8), and the third lumen 3' with an opening 4' inside the second balloon 1' for inflating the second balloon and for measuring pressure inside the second balloon.

The diameter of the first and third lumen (air channel) is preferably smaller than the diameter of the second lumen (food channel).

Similar as for the balloon 3000 of FIG. 30, preferably the different lumen are clearly marked to avoid misconnection, or have different connectors, or the like.

The outer diameter 11 and effective balloon length 12 of the inflated balloons is preferably the same as for the single balloon of FIG. 30, but for the same outer diameter and effective length, the total inner balloon volume is somewhat lower than for the single balloon.

Reference 5 indicates the "distal balloon ending", i.e. the distal ending of the second balloon 1'. Reference 6 indicates the "proximal balloon ending", i.e. the proximal ending of the first balloon 1.

Similar as for the balloon catheter 3000 of FIG. 30, if the at least one opening 8 is located at a distance smaller than about 10 cm from the distal balloon ending 5, e.g. about 5 cm, then the balloon catheter 3100 is adapted for providing substance (e.g. enteral feeding) into the stomach, whereas if the at least one opening 8 is located at a distance larger than 10 cm from the distal balloon ending 5, e.g. about 20 cm from the distal end of the balloon, the balloon catheter 3100 is adapted for providing substance into the duodenum or small intestine.

A system is also envisioned, that processes the balloon pressures from both balloons. If the system detects that contractions are progressed from the proximal balloon to the distal balloon this would be an indication of a good working stomach, and the GB-MI (gastric balloon motility-index) would be increased. If the movement is in the opposite direction, the GB-MI would be decreased. It is a major advantage of such an embodiment that the GB-MI is not only a measure of contractility but also takes into account progressive or peristaltic contractility. A balloon catheter with two balloons, e.g. like the one shown in FIG. 31 of FIG. 33 or FIG. 34, is ideal for use in such as system.

In a variant of the balloon catheter 3100 just described, the balloon catheter has a first balloon and a second balloon and four lumen: a first lumen for inflating the first balloon and for measuring pressure inside the first balloon, a second lumen for providing a substance into the stomach, a third lumen for inflating the second balloon and for measuring pressure inside the second balloon, and a fourth lumen for providing a substance directly into the duodenum or small intestine. This can be seen as a combination of the balloon catheter of FIG. 30 and that of FIG. 31. A system with such a balloon catheter is shown in FIG. 33.

FIG. 32 shows a schematic block diagram of an exemplary system 3200 according to an embodiment of the present invention. The system comprises a balloon catheter 3230 with one balloon B1 and having two lumen: a first lumen with a first opening 3231 in fluid connection with the first balloon B1, and a second lumen with an opening 3132 outside of the balloon.

The system has a first port P1 which can be connected to a first connector C1 of the balloon catheter 3230 to fluidly connect the pressure sensor 3214 and (if present) also the air pump 3213 to the first lumen. The system has a second port P2 which can be connected to a second connector C2 of the balloon catheter 3230 to fluidly connect the food pump 3212 to the second lumen. The controller can read the pressure values, and can calculate a motility-index, which is displayed on the output means 3242. Medical personnel can control the food pump 3212 by providing instructions to the controller 3210 via the input means 3241, based on the motility-information provided on the output means 3242. The system may further comprise a storage device 3261 for storing said pressure data and/or said motility information. While the system is not the main focus of the present application, it illustrates by way of an example how the balloon catheter 3230 can be used.

FIG. 33 shows a schematic block diagram of an exemplary system 3300 according to an embodiment of the present invention. The system comprises a balloon catheter 3330 with two balloons B1, B2 and only four lumen: a first lumen connected to the first balloon B1, a second lumen for feeding into the stomach, a third lumen connected to the second balloon B2, a fourth lumen for feeding into the duodenum or small intestine. The system 3300 is very similar to that of FIG. 32, except that it has two pressure sensors and two air pumps and two food pumps, which are connectable via port P1 to P4 to the four corresponding lumen, via connectors C1 to C4 of the balloon catheter 3330. The storage device 3261 is optional.

FIG. 34 shows a schematic block diagram of an exemplary system 3400 according to an embodiment of the present invention. The system comprises a balloon catheter 3430 with two balloons B1, B2 and having only three lumen: a first lumen with opening 3431 fluidly connected to the first balloon B1, a second lumen with opening 3432 for feeding into the stomach, and a third lumen with opening 3433 fluidly connected to the second balloon B2. The electronics system is very similar to that of FIG. 33, except that it only has one food pump, and three ports.

FIG. 35 shows a schematic block diagram of an exemplary system 3500 according to an embodiment of the present invention. The system comprises a balloon catheter 3530 with one balloon B1 and three lumen: a first lumen with opening 3531 fluidly connected to the first balloon B1, a second lumen with opening 3532 for feeding into the stomach, and a fourth lumen with opening 3534 for feeding into the duodenum or small intestine. The electronics system is very similar to that of FIG. 33, except that it only has one food pump and two switches 3551, 3552 to either provide food into the stomach or into the duodenum or small intestine.

CITED REFERENCES

1. Szarka L A, Camilleri M. Methods for measurement of gastric motility. American Journal of Physiology—Gastrointestinal & Liver Physiology. 2009; 296(3):G461-G75.
2. Jahnberg T, Martinson J, Hulten L, Fasth S. Dynamic gastric response to expansion before and after vagotomy. Scand J Gastroenterol. 1975; 10(6):593-8.
3. Schwartz T W, Grotzinger U, Schoon I M, Olbe L. Vagovagal stimulation of pancreatic-polypeptide secretion by graded distention of the gastric fundus and antrum in man. Digestion. 1979; 19(5):307-14.
4. Malagelada J R, Rees W D, Mazzotta L J, Go V L. Gastric motor abnormalities in diabetic and postvagotomy gastroparesis: effect of metoclopramide and bethanechol. Gastroenterology. 1980; 78(2):286-93.
5. Takita S, Nishii H, Kuwajima T, Yano Y. Gastric motor function after selective proximal vagotomy and pyloroplasty for peptic ulcer. Chir Gastroent (Gastroent Surg). 1975; 9(2).
6. Takita S, Nishi H, Nishijima H. Gastric motility after selective proximal vagotomy. Gastroenterol Jpn. 1978; 13(5):345-52.
7. Hurt R T, McClave S A. Gastric residual volumes in critical illness: what do they really mean? Critical care clinics. 2010; 26(3):481-90, viii-ix.
8. Stanghellini V, Tack J. Gastroparesis: separate entity or just a part of dyspepsia? Gut. 2014; 63(12):1972-8.
9. Talley N J, Ford A C. Functional Dyspepsia. The New England journal of medicine. 2015; 373(19):1853-63.
10. Deloose E, Janssen P, Depoortere I, Tack J. The migrating motor complex: control mechanisms and its role in health and disease. Nature reviews Gastroenterology & hepatology. 2012; 9(5):271-85.
11. Schoonjans R, Van Vlem B, Van Heddeghem N, Vandamme W, Vanholder R, Lameire N, et al. The 13C- octanoic acid breath test: validation of a new noninvasive method of measuring gastric emptying in rats. Neurogastroenterology & Motility. 2002; 14(3):287-93.
12. Maes B D, Ghoos Y F, Geypens B J, Mys G, Hiele M I, Rutgeerts P J, et al. Combined carbon-13-glycine/carbon-14-octanoic acid breath test to monitor gastric emptying rates of liquids and solids. Journal of Nuclear Medicine. 1994; 35(5):824-31.
13. Hawkes N D, Richardson C, Evans B K, Rhodes J, Lewis S J, Thomas G A. Effect of an enteric-release formulation of naloxone on intestinal transit in volunteers taking codeine. Aliment Pharmacol Ther. 2001; 15(5):625-30.
14. Mikus G, Trausch B, Rodewald C, Hofmann U, Richter K, Gramatte T, et al. Effect of codeine on gastrointestinal motility in relation to CYP2D6 phenotype. Clinical pharmacology and therapeutics. 1997; 61(4):459-66.
15. Gonenne J, Camilleri M, Ferber I, Burton D, Baxter K, Keyashian K, et al. Effect of alvimopan and codeine on gastrointestinal transit: a randomized controlled study. Clinical gastroenterology and hepatology: the official clinical practice journal of the American Gastroenterological Association. 2005; 3(8):784-91.
16. Crighton I M, Martin P H, Hobbs G J, Cobby T F, Fletcher A J, Stewart P D. A comparison of the effects of intravenous tramadol, codeine, and morphine on gastric emptying in human volunteers. Anesthesia and analgesia. 1998; 87(2):445-9.

The invention claimed is:

1. A gastric motility measurement device comprising:
a catheter;
one or more inflatable balloons fixedly attached to said catheter;
wherein:
an external diameter of the balloon catheter, when each of said one or more inflatable balloons is deflated, is such that the balloon catheter can pass through a hole having a diameter of 23 French (about 7.7 mm) such that the balloon catheter is suitable for delivery of the one or more inflatable balloon to a stomach of a person via a nose of said person,
said catheter comprises at least a first lumen which is fluidly coupled to an inside of the one or more inflatable balloons via at least one first opening in the surface of the catheter;
the one or more inflatable balloons are adapted to have an overall non-spherical shape and have an outer diameter in the range from 4.0 to 7.0 cm in combination with:
an effective length from 9.0 cm to 18.0 cm and
a total inner volume in the range from 90 ml to 330 ml, when each of the one or more inflatable balloons is inflated by a pressure of 0.20 psi in an environment of 20° C. and 1013 mbar absent a counter-pressure; and
the one or more inflatable balloons are made of a polyurethane material having a durometer in the range from 70 to 100 shore A, a plastic material having a durometer in the range from 25 to 100 shore D, or a plastic material having a durometer in the range from 50 to 120 rockwell R, and
wherein the gastric motility measurement device further comprises:
a first pressure sensor fluidly connected to the first lumen for measuring a pressure of a fluid in a first balloon of the one or more inflatable balloons; and
a control unit operatively connected to the first pressure sensor for obtaining pressure information indicative of gastric motility.

2. The gastric motility measurement device according to claim 1, wherein each of the one or more inflatable balloons is made of the polyurethane material having said durometer in the range from 70 to 100 shore A.

3. The gastric motility measurement device according to claim 1, wherein each of the one or more inflatable balloons is made of the plastic material having said durometer in the range from 25 to 100 shore D.

4. The gastric motility measurement device according to claim 1, wherein each of the one or more inflatable balloons is made of the plastic material having said durometer in the range from 50 to 120 rockwell.

5. The gastric motility measurement device according to claim 1, wherein the one or more inflatable balloons are adapted for having the total inner volume in the range from 110 ml to 330 ml, when inflated by a pressure of 0.20 psi in an environment of 20° C. and 1013 mbar absent a counter-pressure.

6. The gastric motility measurement device according to claim 1, wherein the one or more inflatable balloons are adapted for having the outer diameter of between 4.3 and 5.5 cm, when inflated by a pressure of 0.20 psi in an environment of 20° C. and 1013 mbar absent a counter-pressure.

7. The gastric motility measurement device according to claim 1, wherein the external diameter of the balloon catheter, when each of said one or more inflatable balloons is deflated, is such that the balloon catheter can pass through a hole having a diameter of 19 French (about 6.3 mm).

8. The gastric motility measurement device according to claim 1, wherein the catheter extends through a distal end of each of said one or more inflatable balloons; and wherein said catheter further comprises a second lumen that is fluidly coupled with at least one second opening arranged in the surface of the catheter outside of the balloons, for delivery of a substance or collection of a substance.

9. The gastric motility measurement device according to claim 8, wherein the at least one second opening is located at a distance less than 10 cm from the distal end of the one or more inflatable balloons for delivery of said substance into the stomach of the person, or for collection of a substance from the stomach of the person.

10. The gastric motility measurement device according to claim 8, wherein the at least one second opening is located at a distance greater than 10 cm from the distal end of the one or more inflatable balloons, for delivery of said substance into the duodenum or small intestine of the person, or for collection of a substance from the duodenum or small intestine of the person.

11. The gastric motility measurement device according to claim 1, wherein the one or more inflatable balloons comprises a single balloon, the single balloon fluidly connected to said first lumen.

12. The gastric motility measurement device according to claim 1, wherein the one or more inflatable balloons comprises a first balloon and a separate second balloon, the first balloon and the second balloon being substantially fluidly isolated;
the first balloon is fluidly connected to said first lumen; and
the balloon catheter further comprises a third lumen comprising at least one third opening fluidly connected with the second balloon.

13. A gastric motility measurement system, the system comprising:
- a balloon catheter to obtain pressure values related to gastric motility, the balloon catheter comprising:
- a catheter, and
- one or more inflatable balloons fixedly attached to said catheter;
- wherein:
  - an external diameter of the balloon catheter, when each of said one or more inflatable balloons is deflated, is such that the balloon catheter can pass through a hole having a diameter of 23 French (about 7.7 mm) such that the balloon catheter is suitable for delivery of the one or more inflatable balloon to a stomach of a person via a nose of said person,
  - said catheter comprises at least a first lumen which is fluidly coupled to an inside of the one or more inflatable balloons via at least one first opening in the surface of the catheter;
  - the one or more inflatable balloons are adapted to have an overall non-spherical shape and have an outer diameter in the range from 4.0 to 7.0 cm and an effective length from 9.0 cm to 18.0 cm when each of the one or more inflatable balloons is inflated by a pressure of 0.20 psi in an environment of 20° C. and 1013 mbar absent a counter-pressure; and
  - the one or more inflatable balloons comprises a hardness in the range of one or more of 70 to 100 shore A, 25 to 100 shore D, or 50 to 120 rockwell R;
- a first pressure sensor fluidly connected to the first lumen for measuring a pressure of a fluid in a first balloon of the one or more inflatable balloons; and
- a control unit operatively connected to the first pressure sensor for obtaining pressure information indicative of gastric motility.

14. The system according to claim 13 further comprising a second pressure sensor fluidly connected to a third lumen for measuring a pressure of a fluid in a second balloon of the one or more inflatable balloons; wherein the control unit is operatively connected to the first and second pressure sensor for obtaining pressure information indicative of gastric motility.

15. The system according to claim 14, the system further comprising:
- a first fluid pump fluidly connected to the first lumen; and
- a second fluid pump fluidly connected to the third lumen,
  - wherein the control unit is operatively connected to the first fluid pump for inflating, deflating, or inflating and deflating the first balloon and the control unit is operatively connected to the second fluid pump for inflating, deflating, or inflating and deflating the second balloon.

16. The system according to claim 13, the system further comprising a first fluid pump fluidly connected to the first lumen,
- wherein the control unit is operatively connected to the first fluid pump for inflating, deflating, or inflating and deflating the first balloon.

17. The system according to claim 13, the system further comprising a memory operatively connected to the control unit, the control unit being further adapted for storing the obtained pressure values and/or one or more values derived therefrom, in said memory.

18. The system according to claim 13, the system further comprising a display device operatively connected to the control unit, the control unit being further adapted for visualizing the pressure values and/or gastric motility information derived therefrom, on said display device.

19. The system according to claim 13, wherein the catheter extends through a distal end of each of said one or more inflatable balloons; and wherein said catheter further comprises a second lumen that is fluidly coupled with at least one second opening arranged in the surface of the catheter outside of the balloons located at a distance less than 10 cm from the distal end of the one or more inflatable balloons;
- the system further comprising at least one food pump fluidly connected to the second lumen;
- wherein the control unit is operatively connected to the at least one food pump for providing a substance to the person via the second lumen and via the at least one second opening into the stomach.

20. The system according to claim 19, wherein the catheter further comprises a fourth lumen that is fluidly coupled with at least one fourth opening arranged in the surface of the catheter outside of the balloons located at a distance greater than 10 cm from the distal end of the one or more inflatable balloons;
- wherein the at least one food pump is fluidly connected to the fourth lumen and the control unit is operatively connected to the at least one food pump for providing the substance to the person via the fourth lumen and via the at least one fourth opening into the duodenum or small intestine of the person.

* * * * *